(12) United States Patent
Ganeshalingam et al.

(10) Patent No.: US 9,177,099 B2
(45) Date of Patent: *Nov. 3, 2015

(54) METHOD AND SYSTEMS FOR PROCESSING POLYMERIC SEQUENCE DATA AND RELATED INFORMATION

(75) Inventors: Lawrence Ganeshalingam, Dublin, CA (US); Patrick Nikita Allen, Scotts Valley, CA (US)

(73) Assignee: Annai Systems Inc., Carlsbad, CA (US)

( * ) Notice: Subject to any disclaimer, the term of this patent is extended or adjusted under 35 U.S.C. 154(b) by 83 days.

This patent is subject to a terminal disclaimer.

(21) Appl. No.: 13/223,071

(22) Filed: Aug. 31, 2011

(65) Prior Publication Data

US 2012/0089652 A1    Apr. 12, 2012

Related U.S. Application Data

(60) Provisional application No. 61/378,799, filed on Aug. 31, 2010, provisional application No. 61/406,055, filed on Oct. 22, 2010, provisional application No. 61/411,455, filed on Nov. 8, 2010.

(51) Int. Cl.
| | |
|---|---|
| G06F 19/10 | (2011.01) |
| G06F 19/00 | (2011.01) |
| G06F 17/00 | (2006.01) |
| G06F 19/22 | (2011.01) |

(52) U.S. Cl.
CPC ..................................... *G06F 19/22* (2013.01)

(58) Field of Classification Search
CPC ......... G06F 19/01; G06F 19/22; G06F 19/28; H04L 45/0088
See application file for complete search history.

(56) References Cited

U.S. PATENT DOCUMENTS

| | | | |
|---|---|---|---|
| 5,668,810 A | 9/1997 | Cannella | |
| 6,119,120 A | 9/2000 | Miller | |
| 6,582,932 B1 | 6/2003 | Fukiage et al. | |
| 6,920,396 B1 | 7/2005 | Wallace et al. | |
| 7,158,892 B2 | 1/2007 | Robson et al. | |
| 7,248,582 B2 | 7/2007 | Belgaied et al. | |
| 7,292,709 B2 | 11/2007 | Imajo | |
| 7,354,720 B2 | 4/2008 | Cuppoletti et al. | |
| 7,359,379 B2 | 4/2008 | Jarabek et al. | |
| 7,366,352 B2 | 4/2008 | Kravec et al. | |
| 7,408,957 B2 * | 8/2008 | Calvignac et al. | 370/476 |
| 7,428,554 B1 | 9/2008 | Coberley | |
| 7,467,219 B2 | 12/2008 | Hodges et al. | |
| 7,739,390 B2 | 6/2010 | Brahmbhatt et al. | |
| 7,820,378 B2 | 10/2010 | Van Den Boom et al. | |
| 7,856,317 B2 | 12/2010 | Schilling | |
| 7,885,969 B2 | 2/2011 | Natarajan et al. | |
| 7,996,876 B1 | 8/2011 | Everson et al. | |
| 8,412,462 B1 | 4/2013 | Ganeshalingam et al. | |
| 2002/0029113 A1 | 3/2002 | Wang et al. | |
| 2002/0103937 A1 | 8/2002 | Tillmann et al. | |
| 2002/0111742 A1 | 8/2002 | Rocke et al. | |
| 2003/0039362 A1 | 2/2003 | Califano et al. | |
| 2003/0055824 A1 | 3/2003 | Califano et al. | |
| 2003/0082544 A1 | 5/2003 | Fors et al. | |
| 2003/0097227 A1 | 5/2003 | Bloch et al. | |
| 2003/0113756 A1 | 6/2003 | Mertz | |
| 2003/0224419 A1 | 12/2003 | Corcoran et al. | |
| 2003/0236393 A1 | 12/2003 | Trucksis | |
| 2004/0005558 A1 | 1/2004 | Anderson et al. | |
| 2004/0006433 A1 | 1/2004 | Robson et al. | |
| 2005/0049795 A1 | 3/2005 | Fikuda et al. | |
| 2005/0053968 A1 | 3/2005 | Bharadwaj et al. | |
| 2005/0060599 A1 | 3/2005 | Inami | |
| 2005/0075794 A1 | 4/2005 | Hoffmann et al. | |
| 2005/0119535 A1 | 6/2005 | Yanagihara et al. | |
| 2005/0131649 A1 | 6/2005 | Larsen et al. | |
| 2005/0164247 A1 | 7/2005 | Brunkow et al. | |
| 2005/0181362 A1 | 8/2005 | Apolito et al. | |
| 2005/0267693 A1 | 12/2005 | Allard et al. | |
| 2005/0267971 A1 | 12/2005 | Fritz | |
| 2006/0285685 A1 | 12/2006 | Msezane | |
| 2007/0026406 A1 | 2/2007 | El Ghaoui et al. | |
| 2007/0042372 A1 | 2/2007 | Arita | |
| 2007/0101154 A1 | 5/2007 | Bardsley et al. | |
| 2007/0148658 A1 | 6/2007 | Nelson et al. | |
| 2007/0168135 A1 | 7/2007 | Agarwal et al. | |
| 2007/0190534 A1 | 8/2007 | Birch-Machin et al. | |
| 2007/0271604 A1 | 11/2007 | Webster et al. | |

(Continued)

FOREIGN PATENT DOCUMENTS

| | | |
|---|---|---|
| EP | 0429201 | 5/1991 |
| KR | 1020070115964 A | 12/2007 |

(Continued)

OTHER PUBLICATIONS

CTDP (Networking Guide, 2001, pp. I-149).*
PCT/US011/050078 International Search Report mailed Mar. 21, 2012.
U.S. Appl. No. 12/837,452 Non-Final Rejection mailed Apr. 5, 2012.
Office Action for U.S. Appl. No. 12/828,234, mailed on Mar. 13, 2013.
Office Action for U.S. Appl. No. 13/223,077, mailed on Nov. 20, 2012.
Office Action for U.S. Appl. 13/223,084, mailed on Feb. 7, 2013.
Office Action for U.S. Appl. No. 13/223,088, mailed on Jan. 2, 2013.
Office Action for U.S. Appl. No. 13/223,092, mailed Feb. 7, 2013.
Office Action for U.S. Appl. No. 13/223,097, mailed Nov. 16, 2012.
International Search Report for PCT/US2011/050078, mailed on Mar. 21, 2012.
Written Opinion for PCT/US2011/050078, mailed on Mar. 21, 2012.
International Search Report for PCT/US2012/028642, mailed on Oct. 23, 2012.

(Continued)

*Primary Examiner* — Lori A Clow
(74) *Attorney, Agent, or Firm* — Cooley LLP

(57) ABSTRACT

Methods and systems for organizing, representing and processing polymeric sequence information, including biopolymeric sequence information such as DNA sequence information and related information are disclosed herein. Polymeric sequence and associated information may be represented using a plurality of data units, each of which includes one or more headers and a payload containing a representation of a segment of the polymeric sequence. Each header may include or be linked to a portion of the associated information.

78 Claims, 32 Drawing Sheets

(56) References Cited

U.S. PATENT DOCUMENTS

| | | |
|---|---|---|
| 2007/0288172 A1 | 12/2007 | Aronow et al. |
| 2008/0016201 A1 | 1/2008 | Thompson |
| 2008/0077607 A1 | 3/2008 | Gatawood et al. |
| 2008/0255877 A1 | 10/2008 | Fernandez |
| 2008/0271053 A1 | 10/2008 | Kramer et al. |
| 2008/0281818 A1 | 11/2008 | Tenenbaum et al. |
| 2009/0203986 A1 | 8/2009 | Winnick |
| 2010/0014496 A1 | 1/2010 | Kalika et al. |
| 2010/0050253 A1 | 2/2010 | Baughman et al. |
| 2010/0161607 A1 | 6/2010 | Singh et al. |
| 2010/0169107 A1 | 7/2010 | Ahn et al. |
| 2010/0169313 A1 | 7/2010 | Kenedy et al. |
| 2010/0169338 A1 | 7/2010 | Kenedy et al. |
| 2010/0169340 A1 | 7/2010 | Kenedy et al. |
| 2010/0262718 A1 | 10/2010 | Ikeno |
| 2012/0047202 A1 | 2/2012 | Van Ackere et al. |
| 2012/0089339 A1 | 4/2012 | Ganeshalingam et al. |
| 2012/0089603 A1 | 4/2012 | Ganeshalingam et al. |
| 2012/0089607 A1 | 4/2012 | Ganeshalingam et al. |
| 2012/0089608 A1 | 4/2012 | Ganeshalingam et al. |
| 2012/0095693 A1 | 4/2012 | Ganeshalingam et al. |
| 2012/0230326 A1 | 9/2012 | Ganeshalingam et al. |
| 2012/0230338 A1 | 9/2012 | Ganeshalingam et al. |
| 2012/0230339 A1 | 9/2012 | Ganeshalingam et al. |
| 2012/0232874 A1 | 9/2012 | Ganeshalingam et al. |
| 2012/0233201 A1 | 9/2012 | Ganeshalingam et al. |
| 2012/0233202 A1 | 9/2012 | Ganeshalingam et al. |
| 2012/0236861 A1 | 9/2012 | Ganeshalingam et al. |
| 2013/0246460 A1 | 9/2013 | Maltbie et al. |
| 2014/0164515 A1 | 6/2014 | Maltbie et al. |
| 2014/0164516 A1 | 6/2014 | Maltbie et al. |

FOREIGN PATENT DOCUMENTS

| | | |
|---|---|---|
| WO | WO97/22076 | 6/1997 |
| WO | WO2004/015579 | 2/2004 |
| WO | WO2006/084391 | 8/2006 |
| WO | WO 2006/102128 | 9/2006 |

OTHER PUBLICATIONS

International Search Report for PCT/US2012/028643, mailed Sep. 3, 2012.
International Search Report for PCT/US2012/028644, mailed Sep. 3, 2012.
International Search Report for PCT/US2012/028645, mailed Sep. 3, 2012.
International Search Report for PCT/US2012/028647, mailed Sep. 26, 2012.
International Search Report for PCT/US2012/028650, mailed Sep. 27, 2012.
International Search Report for PCT/US2012/028652, mailed Oct. 23, 2012.
International Search Report for PCT/US2012/057668, mailed Jan. 17, 2013.
U.S. Appl. No. 12/828,234 Non-Final Rejection mailed May 22, 2012.
PCT/US2011/050073 International Search Report and Written Opinion mailed Apr. 25, 2012.
PCT/US2011/050075 International Search Report and Written Opinion mailed Apr. 25, 2012.
PCT/US2011/050077 International Search Report and Written Opinion mailed Apr. 27, 2012.
PCT/US2011/050078 International Search Report and Written Opinion mailed Mar. 21, 2012.
PCT/US2011/050079 International Search Report and Written Opinion mailed Apr. 9, 2012.
PCT/US2011/050080 International Search Report and Written Opinion mailed May 1, 2012.
N. Calabretta, et al., "Optical Signal Processing Based on Self-Induced Polarization Rotation in a Semiconductor Optical Amplifier"; Journal of Lightwave Technology, vol. 22, No. 2, Feb. 2004.
David M. Tanebaum, et al., "The JCVI Standard Operating Procedure for Annotating Prokaryotic Metagenmic Shotgun Sequencing Data", Standards in Genomic Sciences vol. 2, No. 2, pp. 229-237, Apr. 2010.
Office Action for U.S. Appl. No. 13/223,084, mailed May 12, 2014.
Office Action for U.S. Appl. No. 13/223,084, mailed Sep. 27, 2013.
Office Action for U.S. Appl. No. 13/223,092, mailed May 12, 2014.
Office Action for U.S. Appl. No. 13/223,092, mailed Sep. 6, 2013.
Office Action for U.S. Appl. No. 13/223,097, mailed Sep. 18, 2013.
Office Action for U.S. Appl. No. 13/290,992, mailed Sep. 13, 2013.
Office Action for U.S. Appl. No. 13/417,184, mailed Nov. 26, 2013.
Office Action for U.S. Appl. No. 13/417,188, mailed Nov. 4, 2013.
Office Action for U.S. Appl. No. 13/417,189, mailed Nov. 4, 2013.
Office Action for U.S. Appl. No. 13/417,190, mailed Nov. 29, 2013.
Office Action for U.S. Appl. No. 13/417,192, mailed Mar. 26, 2014.
Office Action for U.S. Appl. No. 13/417,192, mailed Aug. 30, 3013.
Office Action for U.S. Appl. No. 13/417,193, mailed Feb. 13, 2014.
Office Action for U.S. Appl. No. 13/417,193, mailed May 23, 2013.
International Search Report and Written Opinion for International Application No. PCT/US2013/047438, mailed Nov. 1, 2013.
Uhn Human CpG Island Microarray Database Searches [online], Retrieved from the Internet on Sep. 28, 2011 and Oct. 3, 2011, <URL: http://data.microarrays.ca/cpg/index.htm>, 16 pages.
Office Action for U.S. Appl. No. 12/828,234, mailed Sep. 8, 2014, 32 pages.
Office Action for U.S. Appl. No. 13/223,084, mailed Aug. 6, 2014, 10 pages.
Office Action for U.S. Appl. No. 13/223,092, mailed Jun. 25, 2014, 9 pages.
Office Action for U.S. App. No. 13/223,092, mailed Jan. 16, 2015, 14 pages.
Office Action for U.S. Appl. No. 13/223,097, mailed Jun. 5, 2014, 8 pages.
Office Action for U.S. Appl. No. 13/223,097, mailed Jan. 7, 2015, 14 pages.
Office Action for U.S. Appl. No. 13/290,992, mailed Aug. 29, 2014, 15 pages.
Office Action for U.S. Appl. No. 13/290,992, mailed Jan. 7, 2015, 11 pages.
Office Action for U.S. Appl. No. 13/417,184, mailed Jun. 16, 2014, 11 pages.
Office Action for U.S. Appl. No. 13/417,187, mailed May 21, 2014, 12 pages.
Office Action for U.S. Appl. No. 13/417,187, mailed Dec. 23, 2014, 13 pages.
Office Action for U.S. Appl. No. 13/417,188, mailed May 29, 2014, 9 pages.
Office Action for U.S. Appl. No. 13/417,189, mailed May 27, 2014, 9 pages.
Office Action for U.S. Appl. No. 13/417,190, mailed Aug. 29, 2014, 10 pages.
Office Action for U.S. Appl. No. 13/417,192, mailed Nov. 19, 2014, 11 pages.
Office Action for U.S. Appl. No. 13/417,193, mailed Sep. 11, 2014, 43 pages.

* cited by examiner

Example Binary Encoding of Nucleotide Bases

Sequence 1  210 → ACGCCGTAACGGGTAATTCA.... (SEQ ID NO.:3)

Memory Contents  0001100101101100 | 0001101010110000 | 1110100 ... × ~ 210M

Sequence 2  220 → AAGCCGTAACGGGTAATTCG.... (SEQ ID NO.:4)

Memory Contents  0000100101101100 | 0001101010110000 | 1110110 ... × ~ 220M

Sequence 3  230 → ACGACGTAACGGGTAATTCG.... (SEQ ID NO.:5)

Memory Contents  0001100001101100 | 0001101010110000 | 1110110 ... × ~ 230M

Sequence 4  240 → ACGACGTATCGGGTAATTCA.... (SEQ ID NO.:6)

Memory Contents  0001100001101100 | 1101101010110000 | 1110110 ... × ~ 240M

Sequence 5  250 → ACGACGTATCGGGTAATACA.... (SEQ ID NO.:7)

Memory Contents  0001100001101100 | 1101101010110000 | 1000100 ... × ~ 250M

*FIG. 2*
*Example Encoding of DNA Sequences Using Coding of FIG. 1 in Memory*

200

300

| BIOLOGICAL EVENT | DESCRIPTION | INSTRUCTION FORMAT | COMMENTS |
|---|---|---|---|
| Transition | Replace G <-> A or C <-> T | TNST dest | Destination is the sequence entry transition result |
| Transversion | Replace G/A <-> C/T | TNSV src, dest | Source is converted to destination |
| Transversion (dest. only) | Replace G/A <-> C/T | TNSV dest | Destination is the sequence entry transversion result |
| Silent Mutation | Single base mutation that DOES NOT change amino acid sequence | SMUT src, dest | Source is converted to destination |
| Mis-sense | Single base mutation that DOES change the amino acid sequence | MISS src, dest | Source is converted to destination |
| Non-sense | Nucleotide substitution that creates one of three stop codons, producing a truncated protein | NONS src, dest | Source is converted to destination |
| Deletion | A nucleotide base has been removed from the sequence | DET src | The source is missing from the nucleotide sequence |
| Deletion Short (no operand) | Same as deletion except nucleotide base is not specified | DETS | Nucleotide base removed from sequence |
| Excision | A nucleotide sequence is removed, e.g., an integrated viral sequence | EXC len, Reg/Mem | Nucleotide sequence of length len deleted, deleted sequence is in location Reg/Mem (Reg/Mem is optional) |
| Insertion Short | Single insertion of nucleotide base | INSTS dst | The dst value is inserted into the nucleotide sequence |
| Insertion Long | Insertion of a sequence | INSTS len Reg/Mem | A nucleotide sequence of length len is inserted. The contents are in Reg/Mem location |
| Conjugation | Insertion of a bacterial sequence into the genome | CONJ len Reg/Mem | A bacterial sequence of length len is inserted. The content are in Reg/Mem location |
| Crossover | Rearrangement at the chromosomal level | CROSS len, addr | A sequence of length len is stored at address addr. Addr can be absolute or relative. With negative addressing value can be negative or positive |
| Jump Absolute | A sequence of pointers is updated by the jump absolute instruction | JMA addr | Move position pointer to the value of absolute address (A_addr) |
| Jump Relative | A sequence of pointers is updated by the jump relative address | JMPR addr | Move position pointer by adding relative address. Relative address may be positive or negative |
| Jump Fixed | Sequence pointer updated by fixed amount | JMPF Reg/Mem | Move position pointer by adding address specified by Reg/Mem location. Address may be positive or negative |

FIG. 3
*Example Instruction Set*

*Example Sequence Comparison*

Example Insertion Event

Example of Chromosomal Rearrangement Event (Translocation)

Example of Alternate Splicing of mRNA

METHOD AND SYSTEMS FOR PROCESSING POLYMERIC SEQUENCE DATA AND RELATED INFORMATION

CROSS-REFERENCE TO RELATED APPLICATIONS

The present application claims the benefit of priority under 35 U.S.C. §119(e) of U.S. Provisional Patent Application Ser. No. 61/378,799 entitled METHOD AND SYSTEMS FOR PROCESSING POLYMERIC SEQUENCE DATA AND RELATED INFORMATION, filed on Aug. 31, 2010, of U.S. Provisional Patent Application Ser. No. 61/406,055 entitled SYSTEMS AND METHODS FOR ANALYSIS OF BIOLOGICAL SEQUENCES, filed on Oct. 22, 2010, and of U.S. Provisional Patent Application Ser. No. 61/411,455 entitled SYSTEMS AND METHODS FOR ANALYZING BIOLOGICAL SEQUENCES USING BIOLOGICAL PROCESSING INSTRUCTIONS, filed on Nov. 8, 2010, the content of each of which is hereby incorporated by reference herein in its entirety for all purposes. This application is related to U.S. Utility patent application Ser. No. 12/837,452, entitled METHODS AND SYSTEMS FOR PROCESSING GENOMIC DATA, filed on Jul. 15, 2010, which claims priority to U.S. Provisional Patent Application Ser. No. 61/358,854, entitled METHODS AND SYSTEMS FOR PROCESSING GENOMICS DATA, filed on Jun. 25, 2010, and to U.S. Utility patent application Ser. No. 12/828,234, entitled METHODS AND SYSTEMS FOR PROCESSING GENOMIC DATA, filed on Jun. 30, 2010, which claims priority to U.S. Provisional Patent Application Ser. No. 61/358,854, entitled METHODS AND SYSTEMS FOR PROCESSING GENOMICS DATA, filed on Jun. 25, 2010, the content of each of which is hereby incorporated by reference herein in its entirety for all purposes. This application is also related to U.S. Utility patent application Ser. No. 13/223,077, entitled METHODS AND SYSTEMS FOR PROCESSING POLYMERIC SEQUENCE DATA AND RELATED INFORMATION, filed on even date herewith, and to U.S. Utility patent application Ser. No. 13/223,084, entitled METHODS AND SYSTEMS FOR PROCESSING POLYMERIC SEQUENCE DATA AND RELATED INFORMATION, filed on even date herewith, and to U.S. Utility patent application Ser. No. 13/223,088, entitled METHODS AND SYSTEMS FOR PROCESSING POLYMERIC SEQUENCE DATA AND RELATED INFORMATION, filed on even date herewith, and to U.S. Utility patent application Ser. No. 13/223,092, entitled METHODS AND SYSTEMS FOR PROCESSING POLYMERIC SEQUENCE DATA AND RELATED INFORMATION, filed on even date herewith, and to U.S. Utility patent application Ser. No. 13/223,097, entitled METHODS AND SYSTEMS FOR PROCESSING POLYMERIC SEQUENCE DATA AND RELATED INFORMATION, filed on even date herewith, the content of each of which is hereby incorporated by reference herein in its entirety for all purposes.

DESCRIPTION OF THE TEXT FILE SUBMITTED ELECTRONICALLY

The contents of the text file submitted electronically herewith are incorporated herein by reference in their entirety: A computer readable format copy of the Sequence Listing (file-name: ANNA_003_01US_SeqList_ST25.txt, date recorded: Oct. 28, 2011, file size 18 kilobytes).

FIELD

This application is generally directed to processing polymeric sequence information, including biopolymeric sequence information such as DNA sequence information.

BACKGROUND

Deoxyribonucleic acid ("DNA") sequencing is the process of determining the ordering of nucleotide bases (adenine (A), guanine (G), cytosine (C) and thymine (T)) in molecular DNA. Knowledge of DNA sequences is invaluable in basic biological research as well as in numerous applied fields such as, but not limited to, medicine, health, agriculture, livestock, population genetics, social networking, biotechnology, forensic science, security, and other areas of biology and life sciences.

Sequencing has been done since the 1970s, when academic researchers began using laborious methods based on two-dimensional chromatography. Due to the initial difficulties in sequencing in the early 1970s, the cost and speed could be measured in scientist years per nucleotide base as researchers set out to sequence the first restriction endonuclease site containing just a handful of bases.

Thirty years later, the entire 3.2 billion bases of the human genome have been sequenced, with a first complete draft of the human genome done at a cost of about three billion dollars. Since then sequencing costs have rapidly decreased. Today, many expect the cost of sequencing the human genome to be in the hundreds of dollars or less in the near future, with the results available in minutes, much like a routine blood test.

As the cost of sequencing the human genome continues to decrease, the number of individuals having their DNA sequenced for medical, as well as other purposes, will likely significantly increase. Currently, the nucleotide base sequence data collected from DNA sequencing operations are stored in multiple different formats in a number of different databases. Such databases also contain scientific information related to the DNA sequence data including, for example, information concerning single nucleotide polymorphisms (SNPs), gene expression, copy number variations. Moreover, transcriptomic and proteomic data are also present in multiple formats in multiple databases. This renders it impractical to exchange and process the sources of DNA sequence data and related information collected in various locations, thereby hampering the potential for scientific discoveries and advancements.

Bioinformatic processing of DNA sequence data currently involves aligning lengthy strings of such sequence data and comparing them so as to identify sequence similarities. Although this process has been able to accommodate the processing of limited quantities of DNA sequence data, it is believed to be inadequate to handle the massive amounts of DNA sequence data expected to be generated in coming years using next-generation DNA sequencing machines. For example, processing of hundreds or thousands of complete human genome sequences using conventional approaches would not be practical in view of the enormous computational resources required by such approaches.

SUMMARY

This application is directed generally to organizing, representing and processing polymeric sequence information, including biopolymeric sequence information such as DNA sequence information. More particularly but not exclusively, this application describes representing a polymeric sequence and associated information using a plurality of data units, each of which includes one or more headers and a payload containing a representation of a segment of the polymeric sequence. Each header may include or be linked to a portion of the associated information.

In one aspect, the disclosure relates to a computer-readable medium for storing a data container having a data structure which facilitates processing of biological sequence data in a data processing system. The medium includes a plurality of biological data units, each of the plurality of biological data units having a payload containing segmented biological sequence data and at least one header associated with biological information relating to the segmented biological sequence data. The segmented biological sequence data may comprise segmented genomic sequence data. The data container may be accessed to facilitate packetizing of the segmented biological sequence data with the biological information for use within the data processing system.

In another aspect, the disclosure relates to a computer-readable medium for storing a data container having a data structure which facilitates processing of polymeric sequence data in a data processing system. The medium includes a plurality of polymeric data units, each of the plurality of polymeric data units having a payload containing segmented polymeric sequence data and at least one header associated with information relating to the segmented polymeric sequence data. The segmented polymeric sequence data may comprise, for example, segmented biopolymeric sequence data or synthetic biological sequence data. The data container may be accessed to facilitate packetizing of the segmented polymeric sequence data with the information for use within the data processing system.

In another aspect, the disclosure is directed to a computer-readable medium for storing a data container having a data structure which facilitates processing of biological sequence data within a data processing system. The medium includes a plurality of biological data units, each of the plurality of biological data units having a payload containing segmented biological sequence data and a set of headers associated with information relating to the segmented biological sequence data. The segmented polymeric sequence data may be, for example, segmented biopolymeric sequence data or synthetic biological sequence data. Each header included within each set of headers may be associated with one of a plurality of layers of a biological data model. In one implementation a first of the plurality of biological data units includes a first segment of biological sequence data and a first set of headers, a second of the plurality of biological data units includes a second segment of biological sequence data and a second set of headers, and at least one of the first set of headers includes first biological information relating to at least one property of the second segment of biological sequence data.

In another aspect, the disclosure is directed to a computer-readable medium for storing a data container having a data structure which facilitates processing of biological sequence data in a data processing system. The medium includes a plurality of polymeric data units, each of the plurality of polymeric data units having a payload containing a representation of at least a portion of a monomer sequence of a polymeric molecule and a set of headers associated with information relating to the at least a portion of the monomer sequence. The data container may be accessed to facilitate packetizing of the segmented biological sequence data with the biological information.

In another aspect, the disclosure relates to a computer-implemented method which includes receiving a plurality of biological sequence segments representative of biological sequence data. The computer-implemented method further includes creating a plurality of biological data units based upon the plurality of biological sequence segments, each of the biological data units having a payload comprised of one biological sequence segment of the plurality of biological sequence segments and a set of headers associated with information relating to the one biological sequence segment. The plurality of biological data units may then be stored within a data container structure. Each set of headers may contain all or part of the information associated with the corresponding one biological sequence segment and/or contain one or more pointers to memory location storing at least a portion of such information.

In another aspect, the disclosure pertains to a computer-implemented method which includes storing a first biological sequence segment in a data container structured to facilitate processing of the biological sequence segment in a data processing system. The computer-implemented method further includes storing a first plurality of headers within the data container structure, each of the first plurality of headers being associated with information relating to the first biological sequence segment. The computer-implemented method also includes defining a first biological data unit including the first biological sequence segment and a first header of the first plurality of headers.

In another aspect, the disclosure relates to a computer-readable medium for storing a data container having a data structure which facilitates processing of biological sequence data in a data processing system. The biological data unit includes a representation of a DNA sequence comprised of a plurality of binary codes arranged in a sequence corresponding to a sequence of positions in the DNA sequence. The representation is embodied such that each binary code included within a first group of the plurality of binary codes represents one of a plurality of nucleotide bases and each binary code included within a second group of the plurality of binary codes represents one of the plurality of nucleotide bases and at least one property associated with the one of the plurality of nucleotide bases.

In a further aspect, the disclosure relates to a computer-readable medium for storing a data container structured to facilitate processing of biological sequence data in a data processing system. The medium includes a first biological data unit associated with the data container wherein the first biological data unit includes first segmented biological sequence data and a first header. The first header identifies a first type of organism associated with the first biological sequence data. The medium also includes a second biological data unit associated with the data container wherein the second biological data unit includes second segmented biological sequence data and a second header. The second header identifies a second type of organism associated with the second biological sequence data wherein the first type of organism is different from the second type of organism. The first segmented biological sequence data may be packetized with at least the first header and the second segmented biological sequence data may be packetized with at least the second header for use within the data processing system.

In another aspect, the disclosure relates to a computer-readable medium for storing a data container structured to facilitate processing of a biological data unit in a data processing system. The biological data unit includes a representation of a DNA sequence comprised of a plurality of binary codes arranged in a sequence corresponding to a sequence of positions in the DNA sequence. The representation is embodied such that each binary code included within a first group of the plurality of binary codes represents one of a plurality of nucleotide bases and each binary code included within a second group of the plurality of binary codes represents a set of two or more of the plurality of nucleotide bases alternatively associated with one of the positions in the DNA sequence. The representation of the DNA sequence may be packetized with header information relating to the DNA sequence for use within the data processing system.

In another aspect, the disclosure relates to a computer-readable medium for storing a data container having a data structure which facilitates processing of a biological data unit in a data processing system. The biological data unit includes a representation of a DNA sequence comprised of a plurality of binary codes wherein at least one of the plurality of binary codes represents at least one nucleotide base and other information associated with the DNA sequence. The other information may, for example, comprise a property of the one nucleotide base. The other information may also identify an additional nucleotide base wherein the at least one nucleotide base and the additional nucleotide base are alternatively associated with a position in the DNA sequence.

The disclosure also relates to a computer-readable medium for storing a data container having a data structure which facilitates processing of biological sequence data in a data processing system. The medium includes a first biological data unit including first segmented biological sequence data and a first header, the first header identifying a first type of organism associated with the first biological sequence data. The medium also includes a second biological data unit including second segmented biological sequence data and a second header, the second header identifying a second type of organism associated with the second biological sequence data wherein the first type of organism is different from the second type of organism.

In a further aspect the disclosure relates to a computer program product for facilitating operation of a data processing system including a data container having a data structure which accommodates polymeric sequence data. The computer program product is comprised of a computer-readable medium including codes for causing a computer to receive segmented polymeric sequence data. The codes further cause the computer to generate a plurality of polymeric data units, each of the plurality of polymeric data units including a payload containing segmented polymeric sequence data and at least one header associated with information relating to the segmented polymeric sequence data. The codes also cause the computer to store the plurality of polymeric data units within the data container structure. The segmented polymeric sequence data may be packetized with the information for use within the data processing system.

The disclosure further relates to a computer program product for facilitating operation of a data processing system including a data container having a data structure which accommodates polymeric sequence data. The computer program product is comprised of a computer-readable medium including codes for causing a computer to receive DNA sequence data. The codes further cause the computer to generate a representation of the DNA sequence data comprised of a plurality of binary codes arranged in a sequence corresponding to a sequence of positions in the DNA sequence data. Each binary code included within a first group of the plurality of binary codes represents one of a plurality of nucleotide bases and each binary code included within a second group of the plurality of binary codes represents one of the plurality of nucleotide bases and at least one property associated with the one of the plurality of nucleotide bases. The codes also cause the computer to store the representation of the DNA sequence data within the data container structure. The representation of the DNA sequence data may be packetized with header information associated with the DNA sequence data for use within the data processing system.

Additional aspects of the disclosure are described below in conjunction with the appended drawings. It should be apparent that the teachings herein may be embodied in a wide variety of forms and that any specific structure, function, or both being disclosed herein is merely representative and not intended to be limiting. Based on the teachings herein one skilled in the art should appreciate that an aspect disclosed herein may be implemented independently of any other aspects and that two or more of these aspects may be combined in various ways. For example, an apparatus or system may be implemented or a method may be practiced using any number of the aspects set forth herein. In addition, such an apparatus or system may be implemented or such a method may be practiced using other structure, functionality, or structure and functionality in addition to or other than one or more of the aspects set forth herein. Furthermore, an aspect may comprise at least one element of a claim.

BRIEF DESCRIPTION OF THE DRAWINGS

The present application may be more fully appreciated in connection with the following detailed description taken in conjunction with the accompanying drawings, wherein:

FIG. 2 illustrates an example of a set of binary encoded DNA sequences stored in a memory using the binary coding of FIG. 1 (SEQ ID NO.: 1), (SEQ ID NO.: 4), (SEQ ID NO.: 5), (SEQ ID NO.: 6), (SEQ ID NO.: 7);

FIG. 3 illustrates one embodiment of an instruction set for processing biological sequences;

DETAILED DESCRIPTION

Introduction

Figure 1:
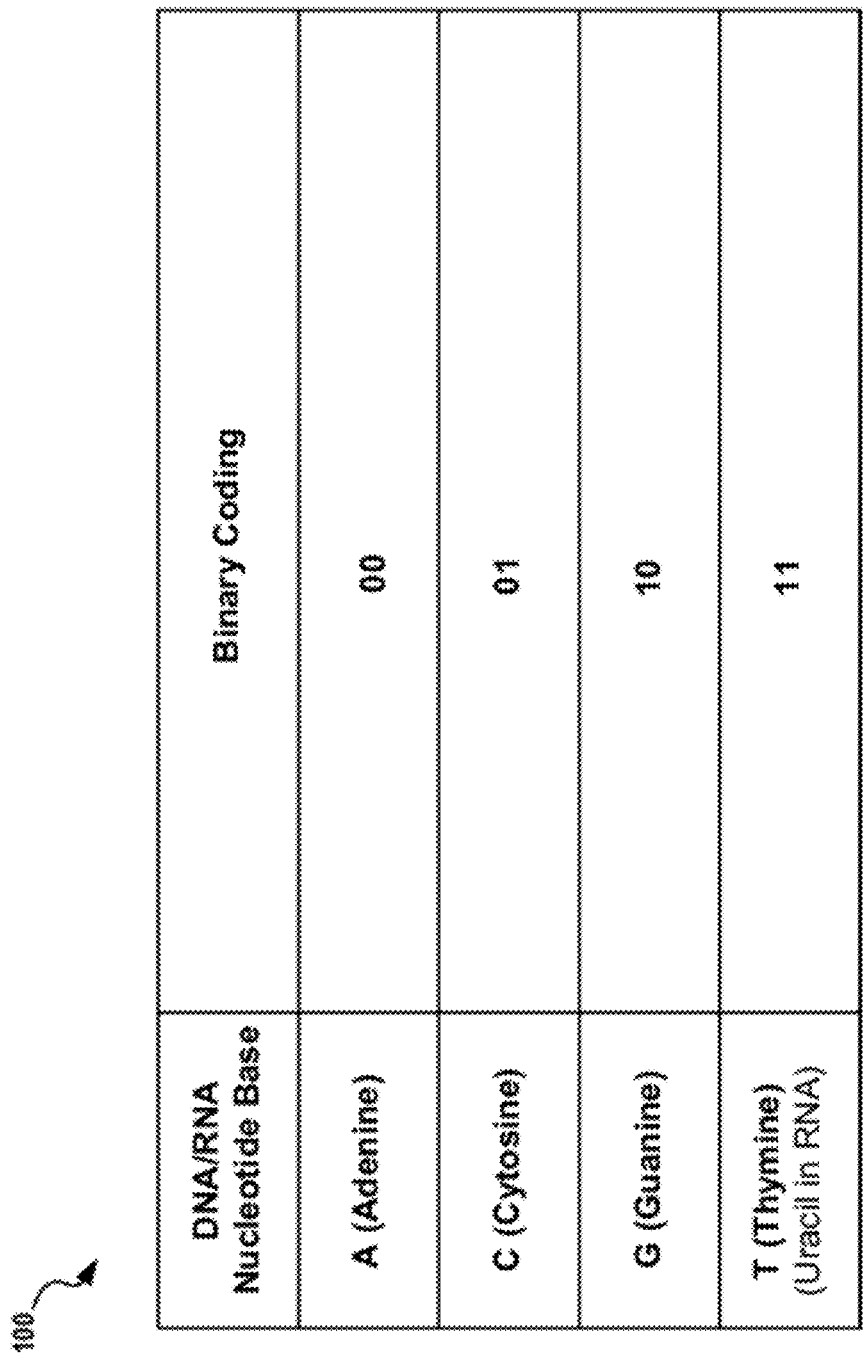
FIG. 1 illustrates details of an example binary coding scheme for base nucleotides in a DNA sequence.

This disclosure relates generally to an innovative new methodology for polymeric sequence manipulation and processing capable of efficiently handling the massive quantities of DNA sequence data and related information expected to be produced as sequencing costs continue to decrease. The disclosed approach permits such sequence data and related information to be efficiently stored in data containers provided at either a central location or distributed throughout a network, and facilitates the efficient searching, transfer, processing, management and analysis of the stored information in a manner designed to meet the demands of specific applications.

As disclosed herein, in one embodiment the innovative method involves dividing source DNA sequences into segments and creating a set of packetized biological data units based upon the resulting segmented DNA sequence data. Each biological data unit will generally be comprised of one or more BioIntelligent™ biologically-relevant headers associated with or relating to a payload containing a representation of segmented DNA sequence data or other non-sequential data of interest. The one or more BioIntelligent™ biologically-relevant headers (also referred to herein as "BI headers") may be associated with or contain information having biological relevance to the segmented DNA sequence data within the payload of the biological data unit. It should be appreciated that any information that is relevant to the payload of a biological data unit can be placed in the one or more BioIntelligent™ biologically-relevant headers of the data unit or, as is discussed below, within BioIntelligent™ biologically-relevant headers of other biolgcial data units. The BioIntelligent™ biologically-relevant headers may be arranged in any order, whether dependent upon or independent of the payload data. However, in one embodiment the BioIntelligent™ biologically-relevant headers are each respectively associated with a particular layer of a biological data model representative of the biological sequence data contained within the payloads of the biological data units with which such headers are associated.

Although the present disclosure provides specific examples of the use of BI headers in the context of a layered data structure, it should be understood that BI headers may be realized in essentially any form capable of embedding biological or non-biological information within, or associating such information with, all or part of any biological or other polymeric sequence or plurality thereof. For example, a polymeric data unit could be created by placing one or more BI headers associated with non-biological information at either end of such a polymeric sequence or within any combination thereof, in any analog or digital format. The BI headers could also be placed within a representation of associated polymeric sequence data, or could be otherwise associated with any electronic file or other electronic structure representative of molecular information.

In the case in which BioIntelligent™ biologically-relevant data is embedded within DNA or other biological sequence information, the BI headers or tags including the BioIntelligent™ biologically-relevant data may be placed in front of, behind or in any arbitrary position within any particular segmented sequence data or multiple segmented data sequences. In addition, the BioIntelligent™ biologically-relevant data may be embedded in a contiguous or randomized manner within the segmented sequence data.

This structured and layered approach will advantageously facilitate the computationally efficient and rapid analysis of, for example, the massive quantities of DNA sequence data expected to be generated by next-generation, high-throughput DNA sequencing machines. In particular, biological data units containing segmented DNA sequence data may be sorted, filtered and operated upon based on the associated information contained within the BioIntelligent™ biologically-relevant headers. This obviates the need to manipulate, transfer and otherwise transfer the segmented DNA sequence data in order to process and analyze such data.

The DNA sequence information included within the biological data units described herein may be obtained from a variety of sources. For example, DNA sequence information may be obtained "directly" from DNA sequencing apparatus, as well as from publicly accessible databases such as, for example, the GenBank database. In the case of the GenBank database, the DNA sequence entries are stored in the FASTA format, which includes annotated information concerning the sequence entries. In one embodiment certain of the information contained within the one or more BioIntelligent™ biologically-relevant headers of each biological data unit would be obtained from publicly accessible databases such as GenBank or EMBL.

Figure 15:
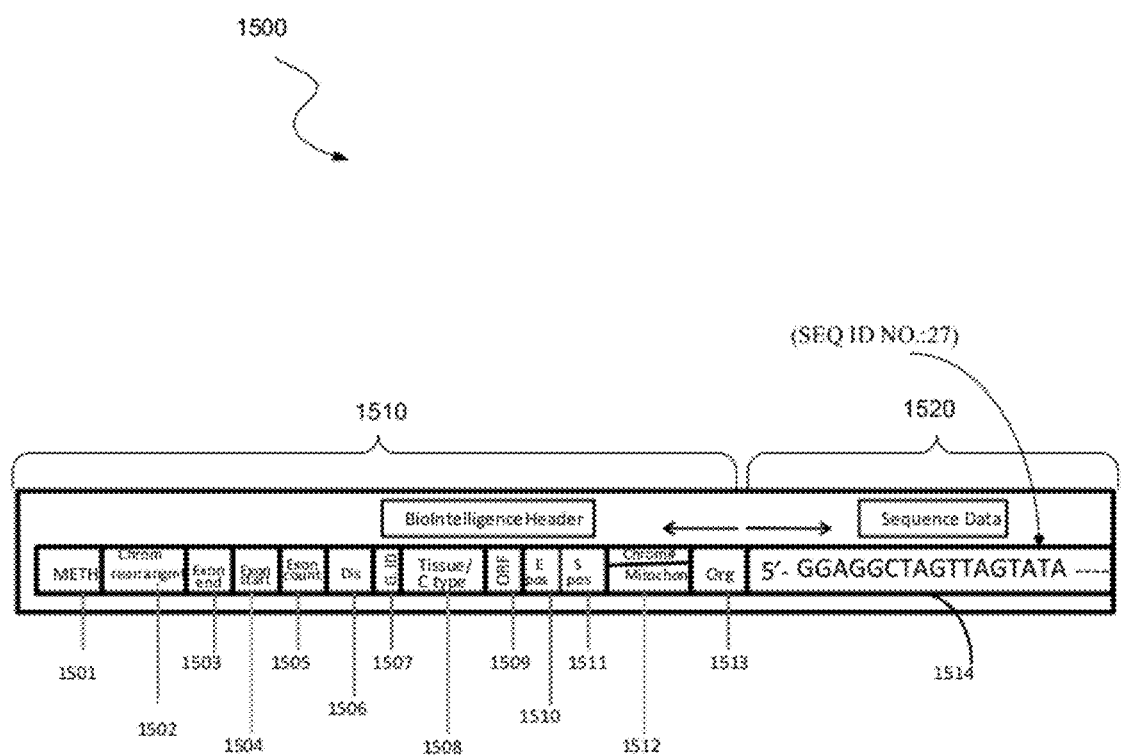
FIG. 15 illustratively represents a biological data unit comprised of a payload containing DNA sequence data and a BioIntelligent™ biologically-relevant header containing information having biological relevance to the DNA sequence data within the payload (SEQ ID NO.: 27).

Turning now to FIG. 15, a representation is provided of a biological data unit comprised of a payload containing DNA sequence data and a BioIntelligent™ biologically-relevant header containing information having biological relevance to the DNA sequence data within the payload. Furthermore, it should be appreciated that information contained in a particular BioIntelligent™ biologically-relevant header may also point or associate with sequence data not contained in the payload. For example, information that associates or relates to a microRNA or an enhancer element involved with the regulation of that gene or interaction with another gene products from a set pathway. Because in the example of FIG. 15 the payload contains DNA sequence data, the biological data unit of FIG. 15 may also be referred to herein as a DNA protocol data unit (DPDU). In one embodiment, other biological data units would be associated with the DPDU depicted in FIG. 15. For example, the RNA sequence data resulting from the DNA sequence data within the payload of the DPDU could be included within RNA protocol data unit (RPDU) comprised of a plurality of RNA-specific BioIntelligent™ biologically-relevant headers and a payload comprised of the RNA sequence data (see, e.g., FIG. 20C). Similarly, a protein protocol data unit (PPDU) comprised of peptide-specific BioIntelligent™ biologically-relevant headers and a payload containing a representation of amino acid sequence data resulting from the DNA sequence data of the DPDU of FIG. 1 could also be associated with this DPDU.

Figure 16:
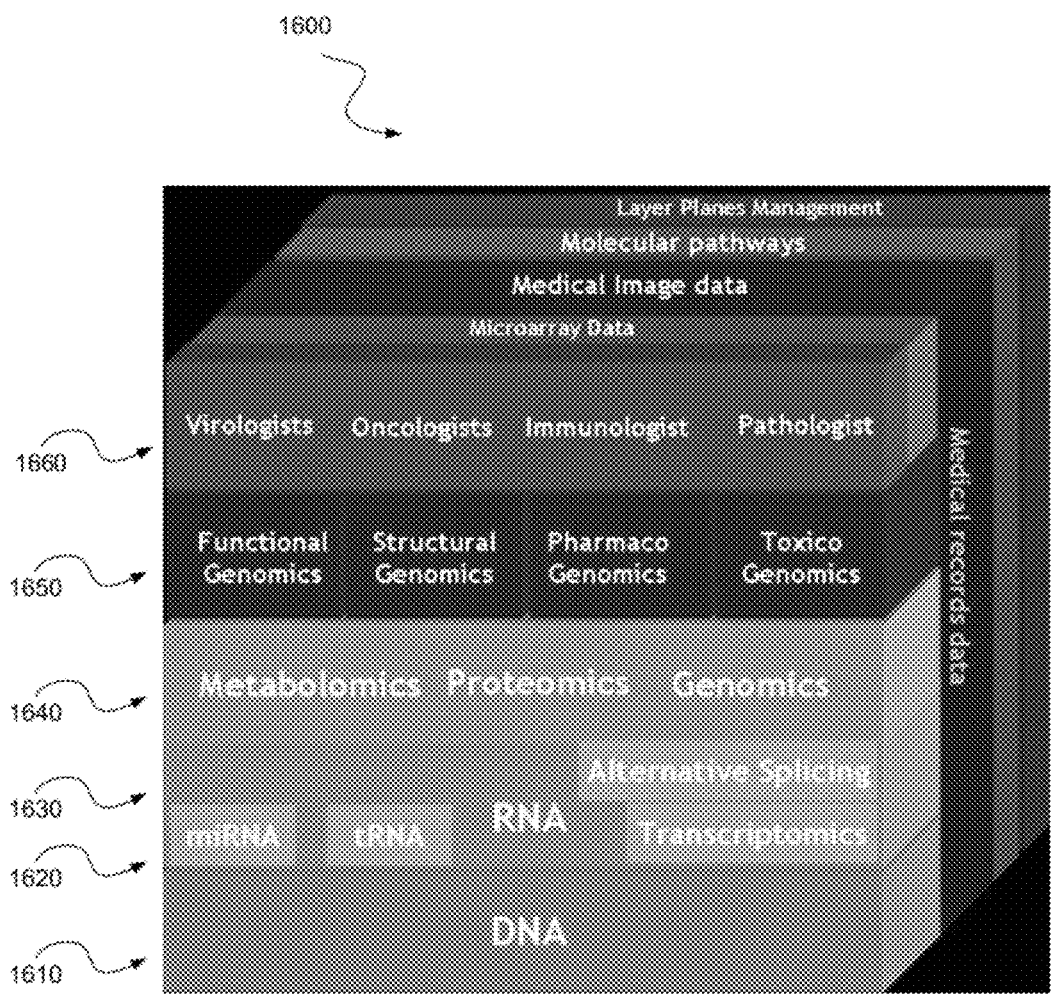
FIG. 16 illustrates a biological data model representative of an interrelationship between biological data units.

Attention is now directed to FIG. 16, which illustrates a biological data model representative of the interrelationship between the biological data units described above. In particular, the BioIntelligent™ biologically-relevant headers of the DNA-specific, RNA-specific and peptide-specific biological data units are each associated with one of the "layers" of the biological data model of FIG. 16, i.e., the DNA, RNA and peptide layers, respectively. Alternatively, a given biological data unit may comprise a payload containing a representation of biological sequence data and a plurality of BioIntelligent™ biologically-relevant headers, each of which is associated with one of the layers of the biological data model of FIG. 16. As is discussed below, although each BioIntelligent™ biologically-relevant header may be characterized as being associated with a data model layer, each may also point to or otherwise reference information in the BioIntelligent™ biologically-relevant header or payload of a separate biological data unit associated with a different layer of the biological data model.

BioIntelligent™ biologically-relevant headers may be associated with any form of intelligence or information capable of being represented as headers, tags or other parametric information which relates to the biological sequence data within the payload of a biological data unit. Alternatively or additionally, BioIntelligent™ biologically-relevant headers may point to relevant or unique (or arbitrarily assigned for the processing purpose) information of associated with the biological sequence data within the payload. A BioIntelligent™ biologically-relevant header may be associated with any information which is either known or predicted based upon scientific data, and may also serve as a placeholder for information which is currently unknown but which later may be discovered or otherwise becomes known. For example, such information may include any type of information related to the source biological sequence data including, for example, analytical or statistical information, testing-based data such as gene expression data from microarray analysis, theories or facts based on research and studies (either clinical or laboratory), or information at the community or population level based study or any such related observation from the wild or nature.

In one embodiment relevant information concerning a certain DNA sequence or biological sequence data may be considered metadata and could, for example, include clinical, pharmacological, phenotypic or environmental data capable of being embedded and stored with the sequence data as part of the payload or included within a look-up table. This advantageously enables DNA and other biological sequences to be more efficiently processed and managed. Information to be embedded or associated in DNA sequence or any other biological, chemical or synthetic polymeric sequence can be represented in the form of packet headers, but any other format or method capable of representing this information in association with the biological sequence data with a data unit payload is within the scope of the teachings presented herein.

The systems described herein are believed to be capable of facilitating real-time processing of biological sequence data and other related data such as, for example and without limitation, gene expression data, deletion analysis from comparative genomic hybridization, quantitative polymerase chain reaction, quantitative trait loci data, CpG island methylation analysis, alternative splice variants, microRNA analysis, SNP and copy number variation data as well as mass spectrometry data on related protein sequence and structure. Such real-time processing capability may enable a variety of applications including, for example, medical applications.

BI headers may be used for the embedding of information, in full or in part, in combination with any polymeric sequence or part or combination thereof, and may placed at either end of such polymeric sequence or in association within any combination of such polymeric sequences. BI headers may be in any format and may be associated with one or more segments of polymeric sequence data. In addition, BI Headers may be positioned in front of or behind (tail) the polymeric sequence data, or at any arbitrary location within the representation of the segmented sequence data. Moreover, the BI headers may comprise continuous strings of information or may be themselves segmented and the constituent segments placed (randomly or in accordance with a known pattern) among the segmented sequence data of one or more biological data units.

The use of BI headers in representing DNA sequence data in a structured format advantageously provides the capability of filtering the sequence data based any of several knowledge fields related to the sequence. This type of format allows for the sequence data to be sorted based on the descriptive information within the BI headers relating to the segmented sequence data of a specific biological data unit. For example, the DNA sequence data represented by a plurality of biological data units could be processed such that, for example, a gene on chromosome 1 could be sorted along with genes from the same or another chromosome if the corresponding gene products are associated with a particular disease or phenotype. Alternatively, a certain chromosomal rearrangement could generate a similar result when a portion of one chromosome is transferred through translocation and becomes part of another.

In the general case not all of the segments of DNA within the set of biological data units resulting from segmentation of an individual genome will directly associate with every field of the applicable BI header field. For example, a certain biological data unit may contain a DNA sequence lacking an open reading frame, in which case the exon count field of the DNA-specific BI header would not be applicable. In any case, this header field along with other header positions could be maintained as place holders for future scaling of the intelligence of the BI header. This permits biological information relating to the segmented DNA sequence data of a certain biological data unit which is not yet known to be easily added to the appropriate BI header of the data unit once the information becomes known and, in certain cases, scientifically validated.

In certain exemplary embodiments disclosed herein, the biological or other polymeric sequence data contained within the payload of a biological data unit is represented in a two-bit binary format. However, it should be appreciated that other representations are within the scope of the teachings herein. For example, the instruction set architecture described in copending application Ser. No. 12/828,234 (the "'234 application") may be employed in certain embodiments described herein to more efficiently represent and process the segmented DNA sequence data within the payload of each biological data unit. Accordingly, in order to facilitate comprehension of these certain embodiments, a description is provided below of the instruction set architecture described in the '234 application.

Overview of Instruction Set Architecture for Polymeric Sequence Processing

Set forth hereinafter are descriptions of instruction set architectures comprised of instructions for processing biological sequences, as well as descriptions of associated biological sequence processing methods and apparatus configured to implement the instructions. The instructions may be recorded upon a computer storage media, and a sequence processing system may contain the storage media and a processing apparatus configured to implement the processing defined by the instructions. In addition, a computer data storage product may contain sequence data encoded using instruction-based encoding.

Also described herein is an article of manufacture in a system for processing biopolymeric information, where the article of manufacture comprises a machine readable medium containing an instruction set architecture including a plurality of instructions for execution by a processor, each of the plurality of instructions being at least implicitly defined relative to at least one controlled sequence, and representative of a biological event affecting one or more aspects of a biopolymeric molecule.

The plurality of instructions may include an opcode corresponding to the biological event and an operand relating to at least a portion of a monomer sequence of the biopolymeric molecule. The one or more aspects may include a monomer sequence of the biopolymeric molecule. The one or more aspects may include a structure of the biopolymeric molecule. The biopolymeric molecule may comprises a DNA molecule and the monomer sequence may comprise at least a portion of a nucleotide base sequence of the DNA molecule.

The biological event may comprise a transition and the operand may comprise at least a first nucleotide base. The operand may further comprise a second nucleotide base corresponding to a result of a transition of the first nucleotide base. The biological event may comprise a deletion. The biological event may comprise a transversion and the operand may comprise at least a first nucleotide base. The operand may further comprise a second nucleotide base corresponding to a result of a transversion of the first nucleotide base.

The biological event may comprise a silent mutation and the operand may comprise a first nucleotide base and a second nucleotide base. The biological event may comprise a mis-sense and the operand may comprise at least a first nucleotide base. The operand may further comprise a second nucleotide base corresponding to a result of a mis-sense of the first nucleotide base. The biological event may comprise a non-sense and the operand may comprise at least a first nucleotide base. The operand may further comprise a second nucleotide base corresponding to a result of a non-sense of the first nucleotide base. The biological event may comprise an excision and the operand may comprise a sequence length. The biological event may comprise a cross-over and the operand may comprise at least a sequence length.

The biological event represented by a first of the plurality of instructions may comprise a transition and the biological event represented by a second of the plurality of instructions may comprise a transversion. The biological event represented by a third of the plurality of instructions may comprise a mis-sense and the biological event represented by a fourth of the plurality of instructions may be a non-sense. The biological event represented by a fifth of the plurality of instructions may comprise a silent mutation and the biological event represented by a sixth of the plurality of instructions may comprise an excision.

The biopolymeric molecule may comprise an mRNA molecule. The biological event represented by one of the plurality of instructions may comprise a constitutive or alternate splice and the operand may identify at least one intron or exon.

One or more of the plurality of instructions may be used to create a delta representation of the nucleotide base sequence relative to the controlled sequence. The delta representation may be based at least in part upon modifications of nucleotide bases in the nucleotide base sequence relative to nucleotide bases of the controlled sequence. The modifications may include one of methylation, carboxylation, formylation, deamination, and other base modifications or analogs. The delta representation may be based at least in part upon one or more structural differences between the DNA molecule and a controlled molecular structure. The one or more structural differences may relate to DNA packaging. The one or more structural differences may relate to chromatin or heterochromatin structure.

One or more of the plurality of instructions may be configured so as to facilitate additional processing. The additional processing may relate to determination of a biological characteristic or property of an organism associated with the instructions. The determination may be based on or related to the biological event.

Also described herein is an apparatus for processing biopolymeric information, the apparatus comprising a program memory for storing a plurality of instructions representative of a corresponding plurality of biological events affecting aspects of a biopolymeric molecule wherein each of the plurality of instructions is at least implicitly defined relative to a controlled sequence and a processing engine for executing ones of the plurality of instructions.

One of the plurality of instructions may include an opcode corresponding to one of the plurality of biological events and an operand relating to at least a portion of a monomer sequence of the biopolymeric molecule. The aspects may include a monomer sequence of the biopolymeric molecule and a structure of the biopolymeric molecule. The biopolymeric molecule may comprise a DNA molecule.

The biological event may comprise a transition and the operand may comprise at least a first nucleotide base. The operand may further comprise a second nucleotide base corresponding to a result of a transition of the first nucleotide base. The biological event may comprise a deletion. The biological event may comprise a transversion and the operand may comprise at least a first nucleotide base. The operand may further comprise a second nucleotide base corresponding to a result of a transversion of the first nucleotide base.

The biological event may comprise a silent mutation and the operand may comprise a first nucleotide base and a second nucleotide base. The biological event may comprise a mis-sense and the operand may comprise at least a first nucleotide base. The operand may further comprise a second nucleotide base corresponding to a result of a mis-sense of the first nucleotide base.

The biological event may comprise a non-sense and the operand may comprise at least a first nucleotide base. The operand may further comprise a second nucleotide base corresponding to a result of a non-sense of the first nucleotide base. The biological event may comprise an excision and the operand may comprise a sequence length. The biological event may comprise a cross-over and the operand may comprise at least a sequence length.

The biological event represented by a first of the plurality of instructions may comprise a transition and the biological event represented by a second of the plurality of instructions may comprise a transversion. The biological event represented by a third of the plurality of instructions may comprise a mis-sense and the biological event represented by a fourth of the plurality of instructions may comprise a non-sense. The biological event represented by a fifth of the plurality of instructions may comprise a silent mutation and the biological event represented by a sixth of the plurality of instructions may comprise an excision.

The biopolymeric molecule may comprise an mRNA molecule. The biological event represented by one of the plurality of instructions may comprise a constitutive or alternate splice event and the operand may comprise at least one intron or exon.

The one or more of the plurality of instructions may be configured to generate a delta representation of a nucleotide base sequence of the DNA molecule relative to the controlled sequence. The delta representation may be based at least in part upon modifications of nucleotide bases in the nucleotide base sequence relative to nucleotide bases of the controlled sequence. The modifications may include one of methylation, carboxylation, formylation, deamination, and/or other base modification or analogs. The delta representation may be based at least in part upon one or more structural differences between the DNA molecule and a controlled molecular structure. The one or more structural differences may relate to DNA packaging. The one or more structural differences may relate to chromatin or heterochromatin structure.

Also described herein is an apparatus for processing biopolymeric information, the apparatus comprising means for storing a plurality of instructions representative of a corresponding plurality of biological events affecting aspects of a biopolymeric molecule, wherein each of the plurality of instructions is at least implicitly defined relative to a controlled sequence, and means for executing ones of the plurality of instructions.

In implementation one or more macro instructions comprised of two or more instructions of the plurality of instructions may be defined, and the sequence of binary codes may be processed using the one or more macro instructions.

The processing may include deriving a delta representation of the biopolymeric data sequence using a reference sequence. The biopolymeric data sequence may comprise a DNA sequence. The delta representation may be based at least upon differences between a nucleotide base sequence of the biopolymeric data sequence and a reference nucleotide base sequence of the reference sequence. The delta representation may be further based upon modifications of nucleotide bases in the nucleotide base sequence of the biopolymeric data sequence relative to nucleotide bases in the reference base sequence. One or more of the plurality of instructions may be used to represent a mutation in the biopolymeric data sequence.

Also disclosed herein is a computer program product comprising a computer readable medium including codes for causing a computer to receive a sequence of binary codes representative of a biopolymeric data sequence and process the sequence of binary codes using a plurality of instructions, each of the plurality of instructions being at least implicitly defined relative to at least one controlled sequence and representative of a biological event affecting one or more aspects of a biopolymeric molecule.

Also disclosed herein is an article of manufacture in a system for processing nucleic acid sequence information, the article of manufacture comprising a machine readable medium containing an instruction set architecture including a plurality of instructions for execution by a processor, wherein at least one of the plurality of instructions is useable to program a mutation event within a nucleic acid sequence.

Also disclosed herein is an article of manufacture in a system for processing DNA sequence information, the article of manufacture comprising a machine readable medium containing an instruction set architecture including a plurality of instructions for execution by a processor wherein at least one of the plurality of instructions is useable to program a chromosome translocation event.

The one or more of the plurality of instructions may be at least implicitly defined relative to at least one controlled sequence.

Also disclosed herein is an article of manufacture in a system for processing nucleic acid sequence information, the article of manufacture comprising a machine readable medium containing an instruction set architecture including a plurality of instructions for execution by a processor wherein at least one of the plurality of instructions is useable to program a splicing event involving a nucleic acid sequence.

One or more of the plurality of instructions may represent a first alternative splicing event involving the nucleic acid sequence. An additional one or more of the plurality of instructions may represent a second alternative splicing event involving the nucleic acid sequence. One or more of the plurality of instructions may be representative of at least one of disease association, gene activation, exon expression, exon inclusion and exon skipping associated with the splicing event. One or more of the plurality of instructions may be at least implicitly defined relative to at least one controlled sequence. One or more of the instructions may include a splice instruction having an operand identifying at least one splice donor site and at least one splice acceptor site. One or more instructions may include a splice instruction that specifies a sequence of jump operations.

Also disclosed herein is an article of manufacture in a system for processing nucleic acid sequence information, the article of manufacture comprising a machine readable medium containing an instruction set architecture including a plurality of instructions for execution by a processor, wherein at least one of the plurality of instructions is useable to determine the presence of a transposable element within a nucleic acid sequence.

The transposable element may affect gene expression. The transposable element may affect gene regulation and/or expression. The transposable element may comprise a bacterial nucleic acid sequence. The transposable element may comprise a viral nucleic acid sequence.

Also disclosed herein is a computer-implemented method for processing nucleic acid sequence information comprising receiving an input binary sequence containing information representing a nucleic acid sequence and identifying a segment of the input binary sequence corresponding to a transposable element.

Also disclosed herein is a computer program product comprising a computer readable medium including codes for causing a computer to receive an input binary sequence containing information representing a nucleic acid sequence and identify a segment of the input binary sequence corresponding to a feature or a partial sequence of a transposable element.

Also disclosed herein is an article of manufacture in a system for processing nucleic acid sequence information, the article of manufacture comprising a machine readable medium containing an instruction set architecture including a plurality of instructions for execution by a processor, wherein at least one of the plurality of instructions is useable to discriminate between the insertion of a first nucleic acid sequence into a second nucleic acid sequence and a rearrangement of elements within the second nucleic acid sequence.

The first nucleic acid sequence may comprise at least a portion of a DNA sequence of a microbial agent.

Genomic Sequencing

Genomic sequences are sequences of data describing genomic characteristics of a particular organism. The term "genomic" generally refers to data that both codes (also referred to as "genetic" data) as well as data that is non-coding. The term "genome" refers to an organism's entire hereditary information. Genomic sequencing is the process of determining a particular organism's genomic sequence.

The human genome, as well as that of other organisms, is made of four chemical units called nucleotide bases (also referred to herein as "bases" for brevity). These bases are adenine(A), thymine(T), guanine(G) and cytosine(C). Double stranded sequences are made of paired nucleotide bases, where each base in one strand pairs with a base in the other strand, according to the Watson-Crick pairing rule, i.e., A pairs with T and C pairs with G (In RNA, Thymine is replaced with Uracil (U), which pairs with A).

A sequence is a series of bases, ordered as they are arranged in molecular DNA or RNA. For example, a sequence may include a series of bases arranged in a particular order, such as the following example sequence fragment: ACGCCG-TAACGGGTAATTCA. (SEQ ID NO.: 1).

The human haploid genome contains approximately 3 billion base pairs, which may be further broken down into a set of 23 chromosomes. The 23 chromosomes include about 30,000 genes. While each individual's sequence is different, there is much redundancy between individuals of a particular genome, and in many cases there is also much redundancy across similar species. For example, in the human genome the sequences of two individuals are about 99.5% equivalent, and are therefore highly redundant. Viewed in another way, the number of differences in bases in sequences of different individuals is correspondingly small. These differences may include differences in the particular nucleotide at a position in the sequence, also known as a single nucleotide polymorphism or SNP, as well as addition, subtraction, or rearrangement or repeats or any genetic or epigenetic variation of nucleotides between individuals' sequences at corresponding positions in the sequences.

Because of the enormous size of the human genome, as well as the genomes of many other organisms, storage and processing genomic sequences (which are typically separate sequences generated from a particular individual or organism, but may also be a sequence fragment, sub-sequence, sequence of a particular gene coding sequence or non-coding sequences between genes, etc.) creates problems with processing, analysis, memory storage, data transmission, and networking Consequently, it is usually beneficial to store the sequences in as little space as possible. Moreover, it is typically important that no information is lost in storage and transmission. Accordingly, processing for storage or transmission of whole or partial sequences should include removing redundant information in a sequence in a lossless fashion.

Existing sequence storage techniques use coding for the four nucleotides (A, C, G and T) which may map them to characters in a text format. This sequence information may be further mapped to binary data. For example, A may be mapped to binary 00, C may be mapped to 01, G to 10 and T to 11 as shown in FIG. 1. Obviously, other encodings may also be used. These binary codes may be stored in a computer memory as arranged in the mapped sequence (as shown in FIG. 2), or in other arrangements.

FIG. 2 illustrates an example of this mapping and memory storage, where the illustrated memory is configured with 16 bit memory locations. However, other memory sizes and configurations could also be used. Five sequences, sequences 210-250, are shown, along with associated memory mappings of the sequences in memory locations 210M-250M, which may be in a memory device such as DRAM, SRAM, Flash, CAM, etc., may be in a database such as on a hard disk drive, etc., or may be on storage media such as DVD ROM, Blu-Ray, or other storage media. In a memory or database, the information shown would require 5 times 40 bits or 200 bits. In this example the sequence size is very small, however, for typical sequences, such as a human sequence, each individual's sequence data would be approximately six billion bits long (i.e., about 6 Gb, or about 0.75 Gigabytes (GB)) if coded as shown.

Consequently, for a database having a relatively small number of sequence entries (for example, 1024 entries or 1K), the database size would approach one terabyte, which is impractical for storage, movement, processing, networking, or analysis for widespread use with current computing technologies. However, as noted previously, in genomic sequences within species (and in many cases across species) the nucleotide bases are typically very similar between individuals, normally having very small deviations (except in the case of bacteria involved with exchanging DNA fragments). This characteristic of DNA may be used, as further described subsequently herein, to effect coding for compression of sequence data as well as perform other processing and output data generation and distribution functions These may include generating genomic specific instructions, performing further processing based on the genomic specific instructions, as well as implementing associated processing software and hardware.

Variations in the DNA sequences of different individuals are a result of deviations (also known as mutations). For example, one type of mutation relates to substitutions of nucleotide bases at common or reference positions in the sequence. A base substitution (also known as a point mutation) is the result of one base in a sequence at a particular position or reference location being replaced with a different one (relative to another sequence, which may be a reference sequence from which other sequences are compared). A base substitution can be either a transition (e.g., between G and A, or C and T) or a transversion (e.g., between G and its paired base C, or A and its paired base T). For example, sequence 1 of FIG. 2 has a transition, with reference to sequence 2, at position 20 (i.e., the G of sequence 2 is replaced with an A in sequence 1).

These seemingly simple and minor mutations are not biologically equivalent and can have significant biological implications and consequences. Transition mutations are more commonly observed and generally result in less deleterious effects on cells, while transversions are generally less common and may lead to more severe phenotypic effects.

In order to express the message encoded in DNA, an RNA copy of the genetic information corresponding to a single gene is translated into the amino acid sequence of the encoded protein. The RNA copy, called a messenger RNA (mRNA) is read by the ribosome in packets of three nucleotide bases called codons. There are 64 codons, of which 61 can be translated. The remaining 3 codons are not translatable and cause the ribosome to stop and disassemble and reinitiate translation of a new message. The 61 codons code for the 20 different amino acids found in proteins. Of the 61 codons, there are 19 codons that encode 10 different amino acids that can be mutated at the first, second, or third position to render that specific codon a non-translatable stop codon with a single base substitution. Of these 19 mutant codons, only 5 (coding for 3 different amino acids) result from transitions while the other 14 are the result of transversions. Table 1 lists the set of codons for which single base substitutions can cause conversion to stop codons.

TABLE 1

| Stop Codon | Tranversions | | | Transitions |
|---|---|---|---|---|
| UAA | AAA$^{(Lys)}$ | GAA$^{(Glu)}$ | | UCG$^{(Gln)}$ |
| | UUA$^{(Leu)}$ | UCA$^{(Ser)}$ | | UGA |
| | UAU$^{(Tyr)}$ | UAC$^{(Tyr)}$ | | UAG |
| UAG | UCG$^{(Ser)}$ | AAG$^{(Lys)}$ | GAG$^{(Glu)}$ | CAG$^{(Gln)}$ |
| | UAU$^{(Tyr)}$ | UAC$^{(Tyr)}$ | UUG$^{(Leu)}$ | UGG$^{(Trp)}$ |
| | | | | UAA |
| UGA | AGA$^{(Arg)}$ | UUA$^{(Leu)}$ | UGC$^{(Cys)}$ | CGA$^{(Arg)}$ |
| | GGA$^{(Gly)}$ | UCA$^{(Ser)}$ | UGU$^{(Cys)}$ | UAA |
| | | | | UGG$^{(Trp)}$ |

From Table 1, it may be observed that single base substitutions resulting in termination of translation are caused primarily by transversions. Thus transition mutations leading to a truncated protein product with negative effects are far less likely. An alternative way to consider this is that translation stop codons are important in defining the correct mature C-terminal end of proteins. However, stop codons can also be mutated to a codon that codes for an amino acid giving rise to a longer than intended polypeptide that will result in a reduced, null function or toxic product. Any base change of the type known as transversion at an existing stop codon will result a codon that encodes an amino acid; this will allow read-through, since the codon becomes translatable (see Table 1). The only base changes to an existing stop codon that result in preserving a stop codon at that position are transition mutations.

There are various types of substitutions. For example, one base at a particular position may be replaced by one of the other bases, e.g., Transition (G<->A or C<->T) and/or Transversion (G/A<->C/T). In a reversion, the mutation reverts to the original base (at the same or a second site, and the function may be regained). In a silent mutation, a single base substitution results in no change in the corresponding amino acid sequence in the protein being expressed. In a mis-sense mutation, a base substitution causes a change at a single amino acid in a protein sequence. In a non-sense mutation, a base substitution that changes a codon specifying an amino acid to one of the three stop codons (UAA, UGA or UAG) thus producing a truncated protein.

In addition to substitutions, mutations may include insertions and deletions. It is noted, however, that other conditions, in addition to substitutions, insertions and deletions, can generate disease conditions. For example, re-arrangement of base sequences, addition of foreign sequences, triplet expansions, copy number variation, and other sequence variations and ordering manipulations may also occur and may result in expressed or unexpressed biological variations, disease conditions, and/or other abnormalities. Each of these types of DNA mutations can be acquired and manifested in different ways and may exert their effects in different or similar fashions.

As with substitutions, there are different types of insertions and deletions. Deletions may include single or multiple base deletions, which are generally randomly distributed in a DNA sequence and are a common replication error, which may result in frame-shift mutation if they are not a multiple of three bases. Excision deletions are larger deletions such as the case with removal of a transposable element. They may be integrated viral sequences or other repeat sequences. Excision deletions are generally precise events that are site directed and can lead to fusion proteins.

Insertions may be simple insertions, where single or multiple bases are inserted, usually at DNA replication. These are typically random events. Transformation insertions are insertions of any foreign DNA sequence in to a cell. In particular, conjugation is an integral part of insertions of bacterial DNA sequences into a host genome, and transduction insertions are insertion of viral sequences. Transposition insertions are insertions of a transposable element into a genome, which are capable of amplifying many copies throughout the genome. These are typically not random. Transposition may also include retrotransposons. Alu family insertions are a 300 base repeat sequence found in various numbers of copies in the human genome and account for about 10 percent of the genome. Insertions in Alu can result in colorectal and breast cancer, hemophilia, and other disease conditions. Cross Over insertions are rearrangements at the chromosomal level. These recombinant events can occur between different chromosomes or within pairs. Inversions are recombination events resulting in reversed polarity in a section of the inverted sequence. Splice site mutations can result in an alternative splicing event of the mRNA processing. Repeat sequences are base sequences repeated throughout the genome. For example, the CA sequence repeats in humans. These may be used in genotyping. SINEs are short interspersed repetitive elements that are non-reverse transcriptase coded and that may amplify bases of mobile elements. Both SINE and LINE are non-LTR (long term repeat) transposable elements. While both types of transposon are duplicated via an RNA intermediate, only LINE encode an enzyme that reverse transcribes the RNA transcript to give a DNA copy that is integrated in the host genome. SINE consists typically of less than 500 bases and, in the case of the Alu family, consists of Alu1 restriction endonuclease recognition sequences. LINEs are long interspersed repetitive elements that encode reverse transcriptase (e.g., RNA reverse transcriptase to DNA). Copy number variations are deletions or duplications of genes that may be associated with particular diseases. Aneuploidy is a sequence having an abnormal number of chromosomes. This may be associated with diseases such as Down's Syndrome. These define mutation events based on DNA (genomic or mitochondrial) or RNA or proteins.

Applications of Genomic-Based Instructions

In one aspect, the above-described biological events, as well as others, may be represented in an instruction format with instructions associated with biological events, as well as other events or processing controls. In some embodiments, hardware, firmware and/or software may be used to perform associated functions. For example, a processor or other instruction processing device may be configured to perform processing using instructions such as are further described below. Likewise, memory or other data storage architectures or storage media may be used to store the instructions and provide them to processors or other processing devices. Encoded instructions may be stored in a computer product, such as a file or database on a computer storage medium. The encoded instructions may be further used to perform additional processing, such as for determination of characteristics or properties of organisms associated with the instructions or underlying sequence data.

One example instruction set includes instructions associated with the following biological events: transition, transversion, silent mutation, mis-sense, non-sense, deletion, excision, insertion, conjugation, crossover, and jump actions. Additional details of an example instruction set 300 for implementing these functions is shown in FIG. 3. It is noted that instruction set 300 of FIG. 3 is provided for purposes of illustration, not limitation, and other instructions sets including more or fewer instructions, instruction configurations, and other additions or variations may also be used in various implementations. For example, other instructions may include additional biological processing instructions and/or other processing instructions. In one implementation, the location within the nucleotide sequence may be implied based on the position of the instruction in the sequence (as explained further subsequently herein). Other instructions can obviously be added to those shown in FIG. 3, such as, for example additional insertion instructions, other manipulation instructions (for example, pointer movements), conditional related instructions (IF and FOR loops), and/or other instructions. In some implementations, instruction set processing as described herein can be combined with compression processing, such as is described in related U.S. patent application Ser. No. 12/828,234, incorporated herein by reference.

Some example applications of instruction sets are further described below.

Example Application 1

Encoding Single Nucleotide Sequence

An example of use of instructions for encoding a single nucleotide sequence representation is provided below. If it is assumed that information is understood for the specified nucleotide sequence, e.g., at a position 15 in the sequence there is a known single nucleotide polymorphism (SNP), the sequence can then be encoded with an instruction set which contains the biologically relative information in an instruction format.

Consider the example nucleotide sequence shown below (denoted as Sequence 1):

```
                                              (SEQ ID NO.: 2)
    CCGGT_CCAGG_GGACG_CGACC_AAAAA_GCCCA
    (Sequence 1)
```

Assuming in Sequence 1 that there is a transition at location 3 and a crossover event where the AAAAA should have been at location 11 (relative to a defined reference sequence), Sequence 1 can be represented by the following instruction set (denoted as Instructions 1, based on the instructions as defined in Table 300 of FIG. 3);
JMPA 2;
TRANS G; (Instructions 1)
JMPR 7;
CROSS 5, 10

Conversely, from these instructions it can be determined that the sequence, if there were no mutations or modifications, would have been:

```
                                              (SEQ ID NO.: 3)
    CCAGT_CCAGG_AAAAA_CGACG_CGACC_GCCCA
    (Sequence 2)
```

This describes that at position three in Sequence 1 there should have been an "A," and the five nucleotide sequence "AAAAA" at position 21 should be at position 11.

Example Application 2

Comparing Nucleotide Sequences

Figure 4:
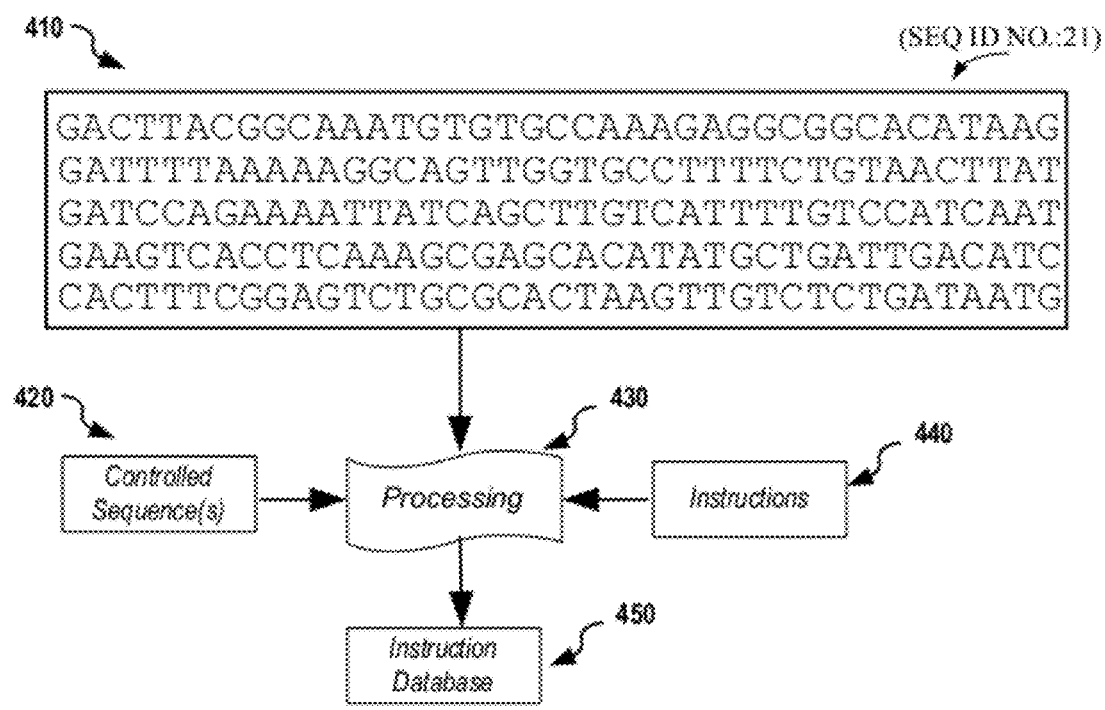
FIG. 4 illustrates one embodiment of a process for coding biological sequences using an instruction set such as is shown in FIG. 3 (SEQ ID NO.: 21)

There are a number of applications where users may wish to compare a nucleotide sequence against other sequences. An example of this is shown in FIG. 4, where sets of sequences 410 may be processed in processing module 430 using a set of instructions 440, such as those shown previously in FIG. 3. By using a set of instructions, as shown in FIG. 4, the sequence may be encoded in an instruction-encoded format which may be stored in a database, such as database 450, a memory, and/or a computer storage media or other data storage device or apparatus.

In particular, as shown in FIG. 4, one or more controlled or reference sequences 420 may be created or selected, which may be stored in a memory or database. The reference sequences may be created or selected as is described in, for example, U.S. patent application Ser. No. 12/828,234.

Figure 13:
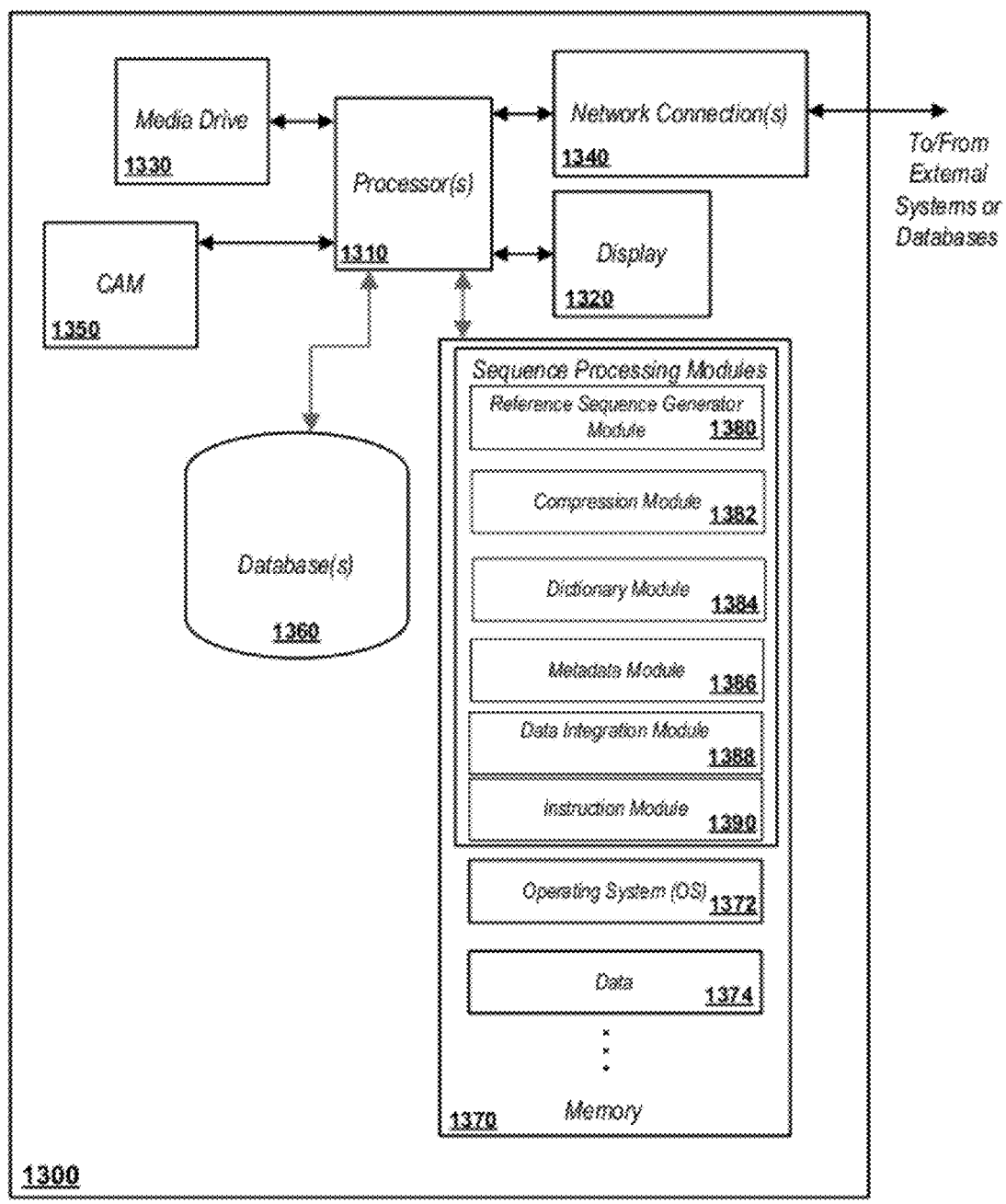
FIG. 13 illustrates an embodiment of a system for processing biological sequence data.

The database sequences 410 may be encoded based on the created or selected reference sequence(s) in processing module 430. This module may be part of a processing system such as shown in FIG. 13. An instruction set 440, which may be the same as or similar to the instruction set shown in Table 300 of FIG. 3, may be used for the encoding. The resulting instruction-encoded sequences may be stored in database 450, which may be the same database the original sequences 410 are stored, or may be another database. The instruction-encoded database may then be used for genomic processing, analysis, networking, data transmission, or other purposes.

Figure 5:
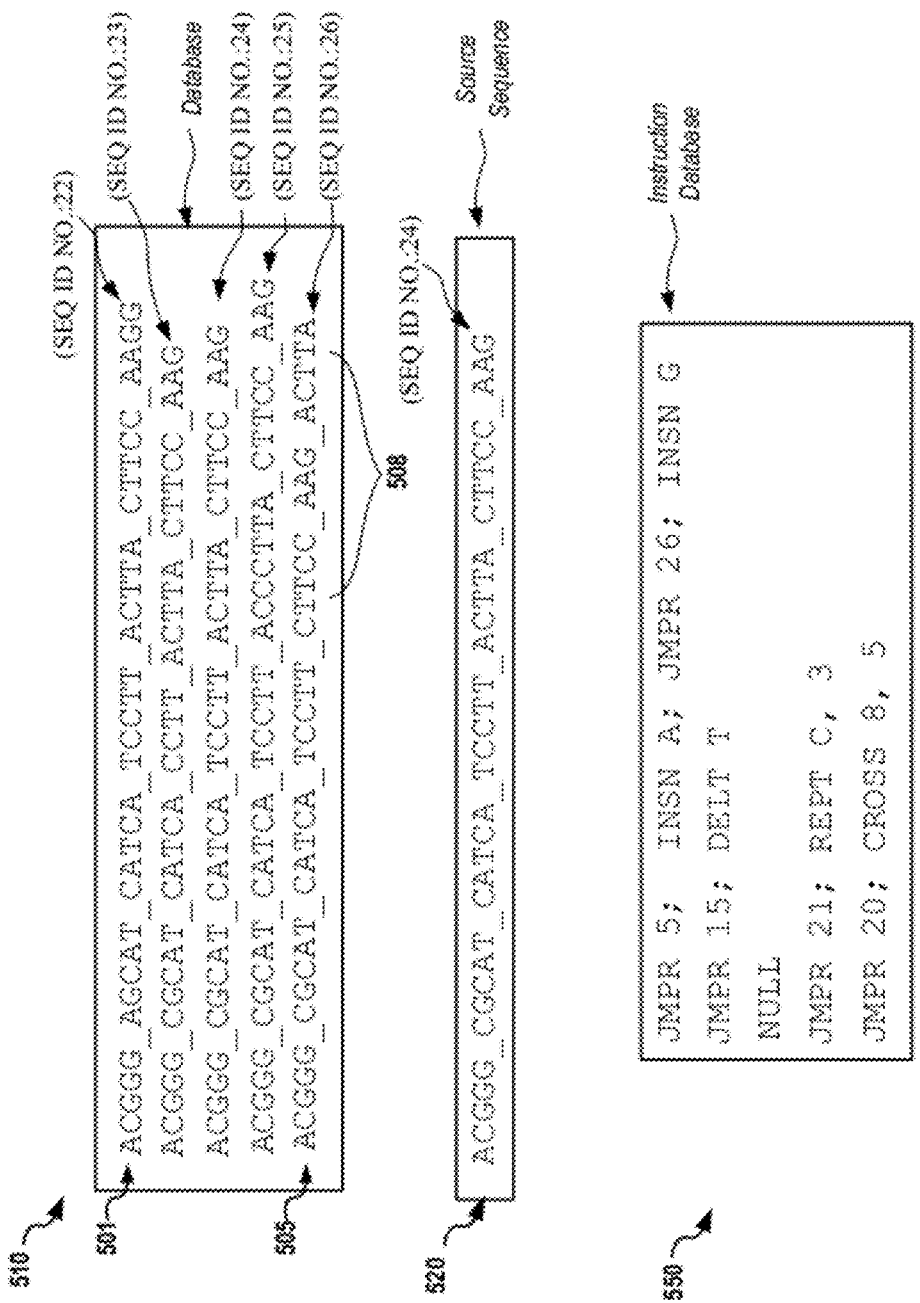
FIG. 5 illustrates an example encoding based on the process of FIG. 4 (SEQ ID NO.: 22), (SEQ ID NO.: 23), (SEQ ID NO.: 24), (SEQ ID NO.: 25), (SEQ ID NO.: 26)

FIG. 5 illustrates an example of data coding consistent with this approach.

As shown in FIG. 5, five nucleotide sequences 510 may be stored in a source sequence database. For purposes of explanation, it is assumed that the middle entry is used for encoding (shown as source or reference sequence 520). Generating instructions may include determining differences between sequence 520 and the entries 510 of the database. The differences between sequence 520 and the other entries in 510 are minimal and can be readily seen in this example. Specifically, entry 501 has an insertion at position 6 and position 27. Entry 505 is equivalent to entry three, with the difference being a crossover event at the locations 508. In various embodiments, controlled, source or reference sequences may be generated in different ways, such as those described below and/or in U.S. patent application Ser. No. 12/828,234.

Example Application 3

Selecting a Controlled/Reference Sequence

In order to minimize the biological differences between the controlled, source or reference sequence and the database, it may be important to select an appropriate controlled/source sequence. One embodiment of reference sequence selection is shown in process 600 of FIG. 6. At stage 605, a source sequence database 680 is selected or accessed. Entries in the database are typically from the same species, however, in some cases entries may be from multiple species. One or more sequences from the database (typically a set of some or all sequences in the database) are then selected for processing. A reference sequence or sequences may be selected (or updated on subsequent iterations) at stage 610. The reference sequence may be selected or determined from entries in the database 680 or may be chosen from other sequences. In an exemplary embodiment, one entry from the database is initially selected and in subsequent iterations of the process, the reference sequence may be adjusted or updated, which may be subsequent to dictionary processing.

At stage 615, the database sequences may be compressed using an instruction set 690. Instruction based encoding may be implemented as described elsewhere herein, and the encoding may be based on the selected reference sequence or sequences.

Figure 6:
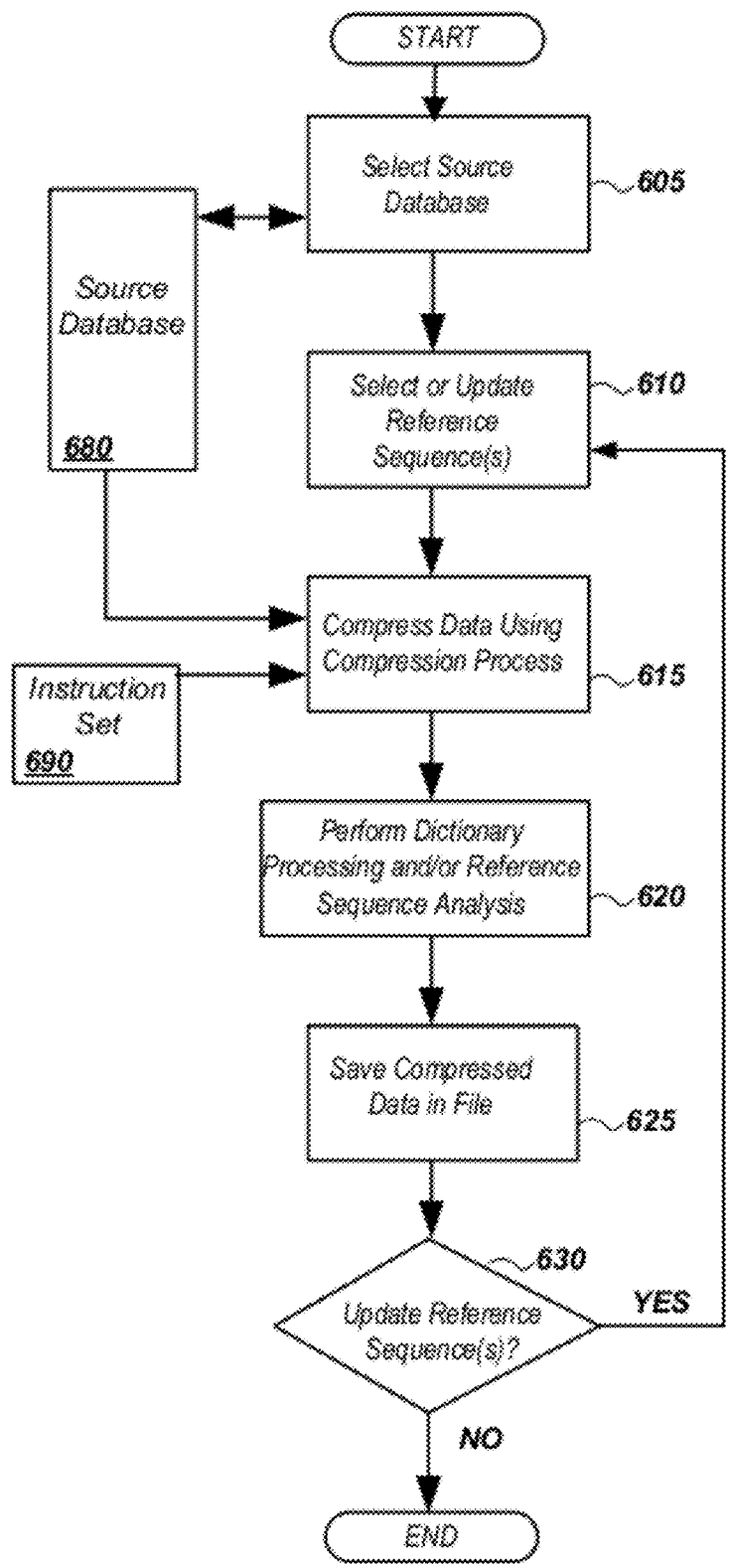
FIG. 6 illustrates an example process for coding biological sequences using instruction set coding.

The instruction set may then be analyzed at stage 620 to perform dictionary processing and/or determine whether the reference sequence(s) should be changed, such as if further size reduction can be achieved. This may be done, for example, based on an analysis on a resulting encoded database to determine if the majority of the entries have the same instruction. For example, the controlled sequence may have a nucleotide base of "A" at location three, but the majority of the entries may have a "G" at location three. The resulting instruction database would then contain the transition instruction at location three. If this is the case, execution may be returned to stage 610 to update the controlled/reference sequence, such as, for example, by replacing the position three value of "A" with a value of "G." After updating on the controlled sequence the compression processing may be repeated. This may be done until there is no further need to update the controlled sequence, such as if a desired level of compression is achieved. This process may essentially reduce the controlled sequence with minimal mutations or deviations. In addition, metadata may optionally be added to the instructions. The metadata may related to clinical and/or pharmacological characteristics or information associated with the instructions and/or underlying sequences. The encoded instructions and any associated metadata or other information may be stored in a database, memory or other storage medium at stage 625. Process 600 may include a decision stage 630, where a decision may be made as to whether the reference sequence or sequences should be updated. This may be based on, for example, a count of dictionary entries determined at stage 620. Process execution may then return to stage 610 as shown in FIG. 6 for subsequence iteration.

In some implementations, there may be more than one source/controlled sequence. In this case, the particular sequence used may be specified in the instruction database entry. For example, if two controlled/source sequences are used, entry one may refer to controlled sequence #1 while entry two may refer to controlled sequence #2. The first instruction in each entry may be in the form: Controlled Sequence, Num, where number (Num) represents the controlled sequence number.

Selection of Instructions

In various embodiments, the number of instructions in the instruction set may vary. In addition, the importance of the instructions used may be highly dependent on the application. In order to manage the instruction set so as to make sure the instruction database does not become unmanageable or inefficient, in some implementations a user may be provided an option to select which subset of instructions (from a larger set) are of interest. In these implementations, only the selected instructions may be used for encoding.

Certain biological events can be represented in one of several ways in a typical instruction set. For example, a substitution can be represented by a SNP or a transition instruction. If these two instructions were selected, there may be an ambiguity or redundancy in the instruction encoding. One way to address this is to use a priority selection. For example, the instructions may be assigned a priority, and if an event can be represented by multiple instructions, the instruction with highest priority may be used. Typically, the highest priority will be the instruction that contains more biological information or is more compact or otherwise more efficient.

Compression Example

One potential benefit of use of an instruction set for compression is being able to represent the database with a smaller footprint. In a simplified example as shown below, a basic instruction set may be assumed, i.e., an instruction set including transition, transversion, and deletion. It is apparent that other instructions and instructions sets may be used in various other implementations.

In a typical database, the genomic sequence would be represented as follows. Since there are four possible values a nucleotide base can have, each of these bases would be stored as a two-bit (binary) value. For example, the four bases may be represented as:

A=>00
C=>01
G=>10
T=>11

Other binary or non-binary configurations could alternately be used. If the database consists of the following five entries, a memory or other storage device would hold the binary sequence listed below:

```
Entry 1:
                                              (SEQ. ID NO. 1)
ACGCCGTAACGGGTAATTCA
or 00.01.10.01.01.10.11.00.00.01.10.10.10.11.00.00.
11.11.01.00

Entry2:
                                              (SEQ. ID NO. 4)
AAGCCGTAACGGGTAATTCG
or 00.00.10.01.01.10.11.00.00.01.10.10.10.11.00.00.
11.11.01.10

Entry3:
                                              (SEQ. ID NO. 5)
ACGACGTAACGGGTAATTCG or 00.01.10.00.01.10.11.00.00.01.10.10.10.11.00.00.
11.11.01.10

Entry4:
                                              (SEQ. ID NO. 6)
ACGACGTATCGGGTAATTCA
or 00.01.10.00.01.10.11.00.11.01.10.10.10.11.00.00.
11.11.01.10

Entry5:
                                              (SEQ. ID NO. 7)
ACGACGTATCGGGTAATACA
or 00.01.10.00.01.10.11.00.11.01.10.10.10.11.00.00.
11.00.01.10
```

For the five entries, the database size would 5*40 or 200 bits. In this example the database is small, but for a typical animal database, such as a human genome database, each entry would be approximately six billion bits long (~6 Gb or ~0.75 GB). If there were only 1024 (1K) entries, the database size approaches one terabyte of data. With current data storage and processing systems, this is generally too much data to store, move, process, network, transmit and/or analyze.

Accordingly, to address this problem, certain characteristics of genetic data may be utilized. For example, for a typical animal, such as a human, the difference between two sequences is on the order of $10^{-3}$ (i.e., 1 difference in 1000 bases). One approach involves establishing a minimum sequence for comparative biological referencing. One form of optimal minimum sequence may be established by first looking at sequences available in a database (i.e., entries) and choosing one that has a minimum average distance from other sequences in the database. Based on the data in the database it may make sense to have more than one minimum sequence template, so to generalize, N reference sequences may be considered. In some cases, the N reference sequences may be taken from entries in the database, but they may also be other previously identified or generated reference sequences. Examples of this are described in U.S. patent application Ser. No. 12/828,234. Having selected a reference sequence or sequences, instead of storing the corresponding full sequence information for every entry in the database, the index of the ideal minimum sequence and the instruction set from that reference sequence may instead be stored.

For example, using the example from FIG. 4 having five database entries, a difference vector for each entry may be calculated. The difference vector may be determined by the number of nucleotide bases at a given position that are different, as well as the value lost for deletions and insertions. The simple example below includes biological sequence database entries 1 and 2:

Entry 1:
(SEQ. ID NO. 1)
ACGCCGTAACGGGTAATTCA
or

00.01.10.01.01.10.11.00.00.01.10.10.10.11.00.00.
11.11.01.00

Entry2:
(SEQ. ID NO. 4)
AAGCCGTAACGGGTAATTCG
or

00.00.10.01.01.10.11.00.00.01.10.10.10.11.00.00.
11.11.01.10

In this example, the nucleotide base in positions two and twenty are different (as shown in BOLD above), but all the bases at every other position are the same. The difference value in this example would therefore be two. Performing this calculation for all the entry combinations, the result is:

Entry 1 difference vector would be=>0, 2, 2, 2, 3 or an average of 1.8
Entry 2 difference vector would be=>2, 0, 2, 4, 4 or an average of 2.4
Entry 3 difference vector would be=>2, 2, 0, 2, 3 or an average of 1.8
Entry 4 difference vector would be=>2, 4, 2, 0, 1 or an average of 1.8
Entry 5 difference vector would be=>3, 4, 3, 1, 0 or an average of 2.2

From this we can see that entries 1, 3, or 4 would yield optimal sequences for biological referencing based on average score. To decide which of the three to utilize, we may choose the one that minimizes the maximum difference. For example, the maximum difference with entry 1 and entry 3 is three, while with entry 4 it is four. Entry 3 may be selected for further explanation as the initial reference sequence (but entry 1 may also be used).

At this stage, two additional steps may be taken. The first step may be used to insure that an ideal minimum sequence is used for referencing, and the second may be the development of a biologically relevant programming language that can be utilized for optimal high-fidelity organization and storage of the data. This approach focuses on biological instructions that can be used to operate on each entry of the database.

Other implementations may use simple scripts to show replacement, addition or removal of bases at certain positions in the entry. This is a simple and inefficient method when representing highly complex molecular biological events that often times result in major structural rearrangements. For example, there are several types of single base substitutions, deletions, and insertions and each of these different types can have very profound biological effects on a cell and or the organism.

To establish one ideal minimum sequence to be used for referencing, a multipronged iterative process, such as is shown in FIG. 6, may be used. Applying this approach, The database would look as follows:

(SEQ. ID NO. 5)
Reference sequence => ACGACGTAACGGGTAATTCG
or 00.01.10.00.01.10.11.00.00.01.10.10.10.11.00.00.
11.11.01.10

Entry 1: JMPR 3; transversion C; JMPR 15; transition A
Entry 2: JMPR1; transversion A; JMPR 2; transversion C
Entry 3: Null
Entry 4: JMPR 8; transversion T, JMPR 10; transition A
Entry 5: JMPR 8; transversion T, JMPR 8; transversion A, JMPR 1; transition A Converting this database to a three bit instruction opcode, a four bit address (addr) value and a two bit base, the database would be nine JMP and nine substitution instructions, which can be represented as 40+9*7+9*5 or 48 bits. Even though, in this example, the reduction is only approximately 25%, with a real genomic database the reduction would be much higher for several reasons, including: 1) in this example, the difference on average is 2 base positions out of 20. This means 90% similar between the sequences. The human genome sequence, however, is closer to 99.9% similar; the source sequence accounts for a large percentage of the total number of bits. This is because the number of entries in this example is five. If the number of entries was one million, then number of bits of the source sequence is insignificant; 2) an optimal source sequence or sequences can be generated as described herein. In some implementations, multiple source sequences may be used; 3) additional biological instructions, e.g., crossover, etc., may also be used; 4) address mapping may be used to reduce the address space further, i.e., the addresses may be mapped from one domain to another.

Using this approach, all original sequence data may be retained, including the reading frame, which allows for processing and analyzing the proposed organization of the data.

Below is an example showing the effect of source/reference sequence selection. The sequence used to calibrate the data does not have to be one of the entries in a source database. It could simply be generated or initially assigned by looking at the common entry for each of the positions. For example in position two every entry has a C except the second entry, which contains an A. In order to develop a minimum sequence a C could be added. This is an example of recursive purification of the ideal sequence used for referencing. Doing this for every position may result in an ideal minimum sequence, and the corresponding compressed database as shown below:

```
Biological referencing sequence:
ACGACGTAACGGGTAATTCA        (SEQ. ID NO. 8)
```

Entry 1: =>JMPR 3; transversion C

Entry 2: =>JMPR 1; transversion A; JMPR 1; transversion C JMPR 15; transition G

Entry 3: =>JMPR 8; transition G

Entry 4: =>JMPR 8; transversion T

Entry 5: =>JMPR 8; transversion T; JMPR 9; transversion A

The instructions database now contains eight JMPR and eight point mutation type instructions. This simple step reduces the database by a factor of ten percent (10%). Taking this approach one step further, addresses can be remapped. For example, there are only six unique addresses represented. These can be remapped to unique values. The instructions of the JMP could also be remapped to include the distance into the opcode. The substitution instruction may also be remapped to include the nucleotide base. Other remappings may also be done based on common or redundant data or information.

In the previous compression example, it is assumed that all the sequences are of the same length. Unfortunately, in general, actual biological sequences, such as DNA sequences, are not all the same sizes (i.e., don't have the same base length). In addition to nucleotides being changed at a particular position, there may also be many different types of inserted or deleted sequence elements with various biological relevance and disease associations.

For example, integration of HIV virus sequence information into the human genome may be considered as analogous to an insertion event in one of the entries in the database. In this case, the specific insertion may be managed and represented in the following manner.

Figure 7:
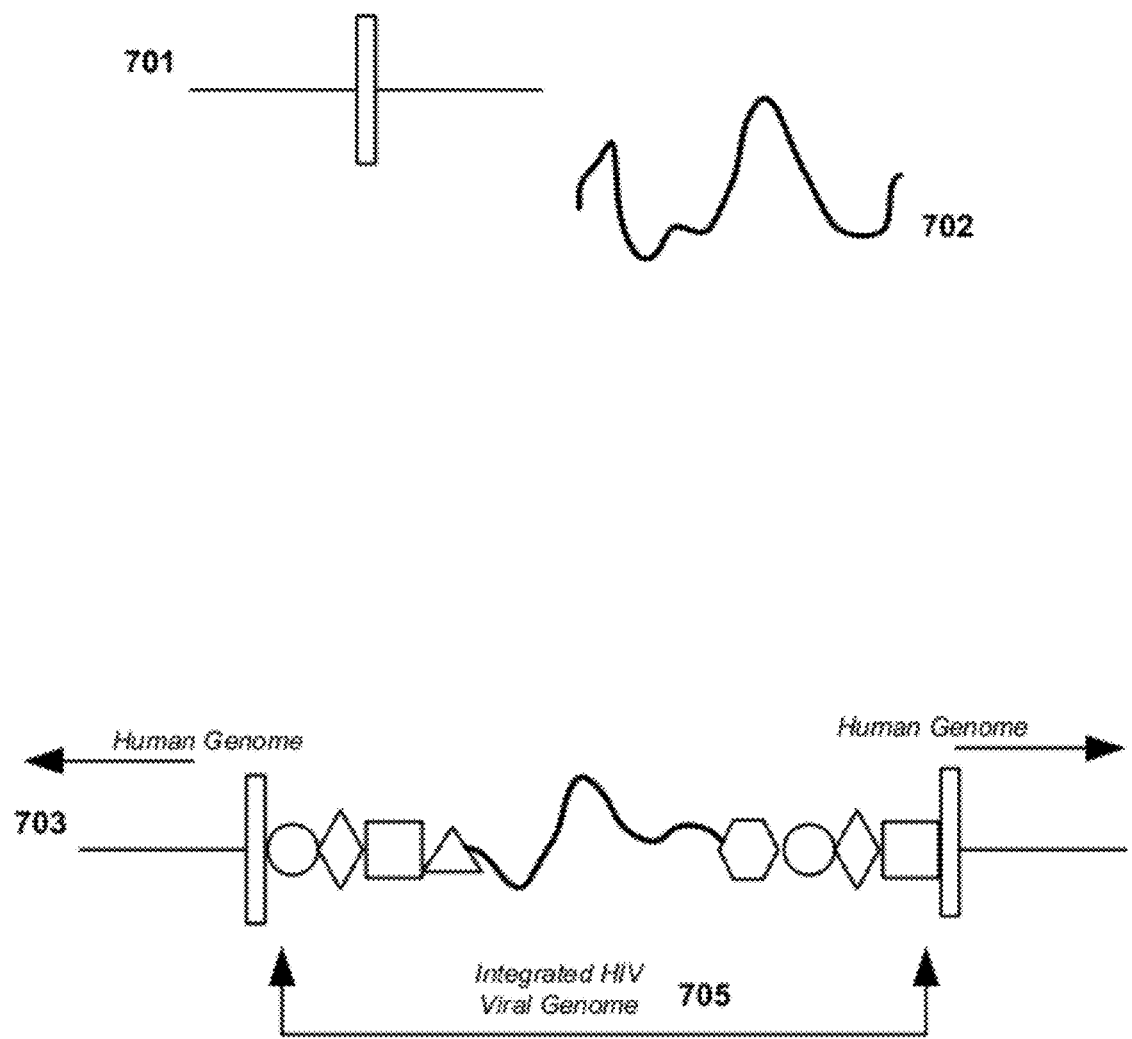
FIG. 7 illustrates details of an example insertion.

Since the viral genome sequence is almost $10^4$ bases, a typical script for insertion at each viral base position would be an inefficient means to represent this type of insertion event. Using the example approach described below, at the insertion site the current positions would align with the controlled source sequence, but as soon as the HIV sequence is encountered it would be apparent that the particular entry no longer aligns with the source. This is shown in FIG. 7.

Upon encountering a stretch of non-aligning sequence, an instruction can be used to jump a specific number of bases, for example a hundred bases, and start alignment again. If the inserted sequence is still unable to align with the controlled then the jump may be made for a larger number, such as several hundreds or thousands of bases until alignment is achieved. The specifically selected jump instruction can then be used to identify the nature of the insertion. For example, if after a 300 base pair jump the entry is able to realign with the reference then it is unlikely to be an HIV viral integration. The jump length, in effect, provides information about the nature of the insertion, such as a possible type of insertion. In this case different addresses may be looked up for short interspersed repetitive elements (SINE). For example, the insert may be a retrotransposon, like the Alu Family, which is about 300 bases long. This information, such as the jump length, may be further used in subsequent processing using the encoded instruction set.

However, if after the instruction to jump several thousand bases there still exists an inability to align with the ideal sequence used for referencing, then the inserted sequence can be probed for sequence elements that have viral association for this example. Alternatively, the inserted sequence may be a result of a crossover event, which would indicate that this inserted sequence is a human genome sequence from a different region of the same chromosome or a different chromosome, and could be present in a 5' to 3' orientation or a reverse polarity (3' to 5') in the case of an inversion. Other events and associated matching may also be determined and used.

As one example, the U3 and U5 regions of the HIV genome are unique sequences that can be used as markers to identify this inserted element as a virus sequence and these viral genome sequences can be held in a memory or other storage element with a specific address. Using instructions it may then be possible to look up the address and determine if this sequence belongs to the suspected HIV genome (or other genomes) as well as, in addition, specifically which strain.

Additionally, the viral repeat sequence (which is normally referred to as R and indicated by diamonds in FIG. 7), the primer binding site, and the polypurine tract are all sequence recognition elements that may be used to determine if the insert is an HIV viral genome (see, e.g., FIG. 7).

Chromosomal rearrangements are a component of major recombination events that may be encoded by a biological sequence programming language and associated instructions. These rearrangements can result in, for example, a deletion, inversion, and/or a translocation. All of these events involve DNA sequence information being moved from one location to another. Even though there might not necessarily be a net loss of genetic information in the case of inversion or translocation, the outcome can often be very similar in mutational effect to a deletion.

For example, consider a gene that is located at the site of the inversion or translocation. As we move from the 5' end towards the 3' end we will arrive at a position where the gene sequence is disrupted. This disruption of a certain gene can contribute to development of some types of cancer.

Chromosomal rearrangement events that result in the deletion, inversion or translocation could influence the integrity and expression of a gene at the site of this type of recombination. For example, if the event is a deletion of the 3' end of a gene then the resulting polypeptide produced will have a truncation at the carboxyl terminal end. This type of event is commonly known to have negative effects on the activity of the gene product, reduced activity or a null. An inversion at that site of the gene would generate a polypeptide where the amino terminus (N-terminus) appears to be normal in the sequence of amino acids up to the site of the inversion then the following series of amino acids from that point to the C-terminus would be random.

Returning to FIG. 7, additional details of the insertion event are illustrated. In this example, integration of HIV viral genome into the human genome sequence is shown as an insertion in an entry in the database. Item 701 is a graphical representation of one entry sequence in a sequence database, such as database 1380 of FIG. 13. In this block, the vertical bar is an indication of the site that will be the insertion site. Since the insertion event has not yet taken place, the DNA sequence is entirely human genome sequence in this region of DNA. Item 702 shows an example of the entire HIV genome sequence. This is a double stranded DNA copy of the HIV viral RNA genome sequence prior to integration into human genome. All the sequence elements that are indicated by special symbols in Item 703 are present in this representation of the complete HIV genome Block 702 (symbols are not shown for clarity). In Item 703, a DNA copy of viral genome has been integrated into human genome target sequence. The vertical bars on either end flanking the viral DNA are human sequences that have been duplicated as a result of the integration process. These bars represent a two base duplication of the original insertion site. The circles represent a region of viral DNA sequence that is called U3. U3 is a region of unique 3' end sequence that is used as a promoter for viral gene expression. The region generally referred to as R indicated by diamonds in this figure is viral repeat sequences. U5 is represented by two squares is the 5' unique sequences that is recognized by the viral protein integrase which is involved in the formation of a pre-integration complex. The triangle shape represents a region known as PB which is the primer binding site where the human tRNA is recruited to prime the reverse transcription of the RNA viral genome. The hexagon is a region known as PP or the polypurine tract and it serves as the initiation site for second strand synthesis. The curved line 720 is a representation of the remainder of the HIV viral genome that encodes all the required viral proteins for completing the life cycle of the virus including glycoproteins for packaging and maturation of viral particles.

For a translocation event, the same is essentially true except in the case where the fragment of DNA that has been translocated to that site belongs to the 3' end of another gene. This type of rearrangement will typically generate an oncogene fusion protein in the case of these chromosomal aberrations and is generally associated with cancer (see, e.g. FIG. 8, which illustrates an example).

Figure 8:
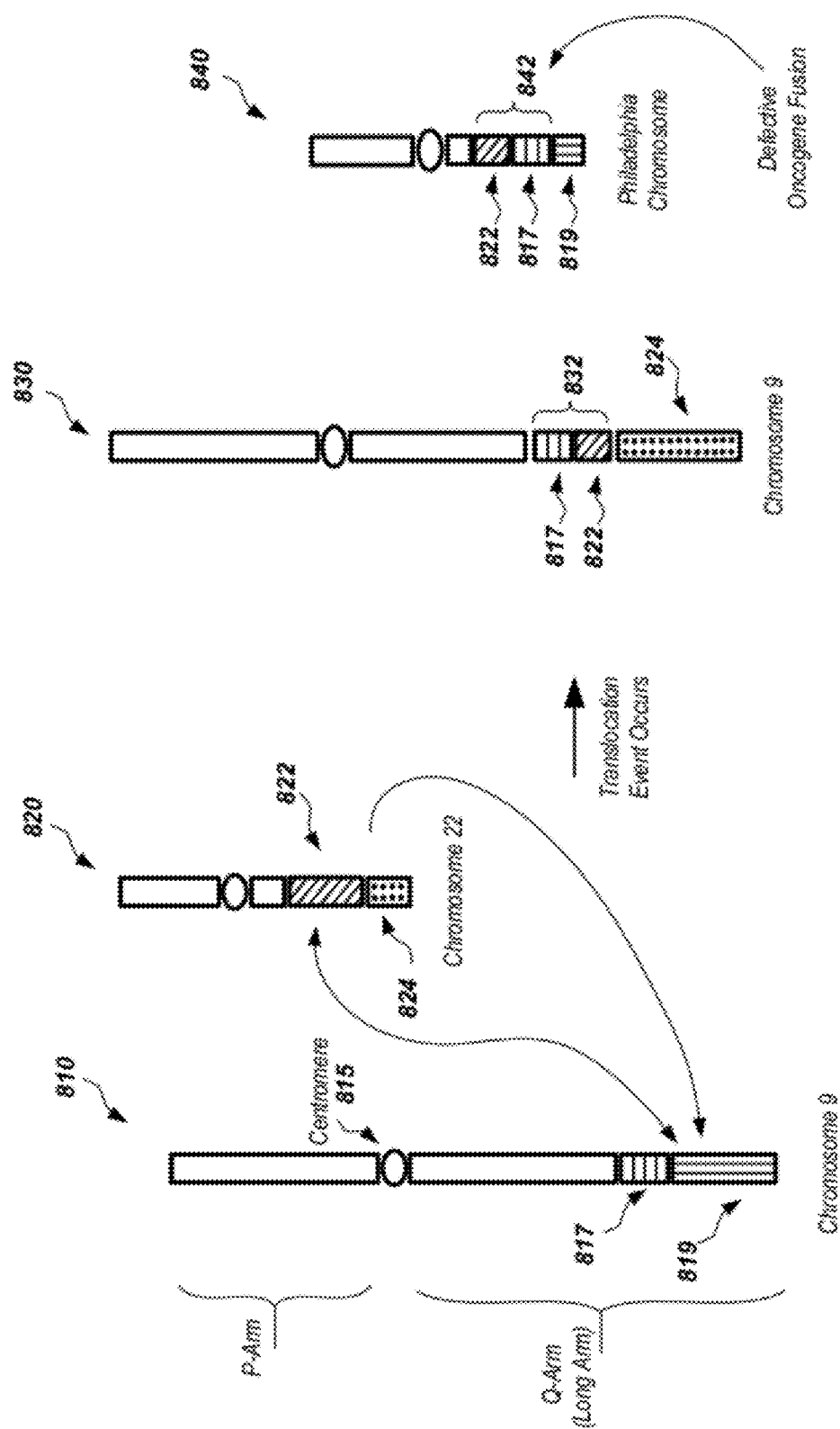
FIG. 8 illustrates details of an example chromosome rearrangement.

In some embodiments, instructions for programming the features for deletions may be a useful instrument for discovery and evaluation of these defects, as, for example, may be seen in cri du chat which will result from deletion of the p arm of chromosome 5, or in the case of chromosomal rearrangement between chromosome 9 and chromosome 22 for Philadelphia chromosome, as shown in FIG. 8.

Turning to FIG. 8, details of an example of a particular chromosomal rearrangement event, commonly known as a translocation, are illustrated. This is only one example of the type of event that comprise a descriptive DNA mutation event that may be used in an instructional programming language in accordance with the present invention, and the invention is not limited to this or any other particular chromosomal defects.

In a translocation, parts of different nonhomologous chromosomes are rearranged and joined or fused. FIG. 8 depicts four chromosomes as shown in panels 810, 820, 830 and 840. Each chromosome includes a short arm or p arm, a centromere, and a long arm or q arm. Centromeres, which are depicted as ovals in FIG. 8, join the long arm to the short arm. In panel 810, an example diagram of chromosome 9 is shown, with the chromosome having a target gene indicated by region 817 on the long arm of the chromosome. Centromere 815 separates the p arm from the q arm. A translocation site is located somewhere in 817. Region 819, at the tip of the q arm, represents the remainder of the chromosome and is also translocated in this example along with a fraction of the 3' end of the target gene in region 817.

Panel 820 illustrates a second chromosome (i.e., chromosome 22) involved in this particular translocation event. As with panel 810, the centromere is indicated by an oval. The target site for translocation is a gene indicated by region 822 of the q arm of chromosome 22 as shown in panel 820. Region 824, which represents the remainder of the chromosome, is located at the tip of the q arm (22q), and this region of DNA is also involved in the translocation event. This is the normal state of chromosome 22 prior to the translocation event.

Following occurrence of a recombination event, the two chromosomes exchange all or part of the illustrated regions of the respective chromosomes. In this example, the 5' end of the original target gene 817 in chromosome 9 is joined with the 3' end of gene 822 from chromosome 22. This results in region 832 shown in panel 830. In addition, the balance of the q arm of chromosome 22 (i.e., region 824) is translocated along with the 3' end of the target gene. The post translocation region 832 remains covalently linked as a contiguous part of chromosome 9 and the gaps shown in panel 830 are included for clarity.

In panel 840, the resulting defective form of chromosome 22 following rearrangement is shown (this is commonly known as Philadelphia translocation or Philadelphia chromosome). A sizable portion of the 5' end of the original gene from region 822 along with the 3' end of the gene from region 817 are fused in gene 842.

Several additional descriptive examples are provided below. In the first example, a single sequence of DNA from a database such as the Genbank at the National Center for Biotechnology Information (NCBI) is considered. Each sequence of DNA entry in such database will have, in addition to the actual sequence, additional information that is known or can be determined about the sequence. At NCBI, acquiring a certain entry sequence from the database will generally provide, at the minimum the base sequence and the size of the molecule, as well as how many bases are contained in this sequence. In addition, some additional information in the form of annotations or metadata may be provided.

Using a set of instruction such as those described above, which may grow and evolve in various embodiments, DNA may be programmed in such a manner that some or all elemental features would be descriptive. For example, whatever can be described in the characterization of a sequence of DNA, a biological instruction set of this language along with proper operation codes may be able to articulate any feature or element or structure or function or genetic component which is known or can be predicted or can be learned about a sequence of DNA (or other biological sequences).

For example, if the entry sequence taken from the database is known to be ten thousand nucleotide bases long and it is known that it codes for a protein, then we may know the actual sequence of bases in this entry, and knowing that it is a gene that encodes a protein it would be expected that some other fundamental information will be available. The source organism will generally be known which will give some indication of the likelihood of the existence of introns, for example. Some or all of the features may be known, such as, but not limited to, sequence elements such as promoter region, start and stop codons, transcription start, restrictions sites, ribosome binding sequence, polyA signal, splice junctions if eukaryotic source, synthetically assigned unique sequences, in addition to other common elements of a gene, that will express a protein product.

When using instruction-encoded sequences to compare the sequence elements present in one database entry versus another, the instruction set may expand to include more advanced operations and become increasingly diverse with regards to the details of the programming for that comparison of DNA sequence. This may be as a result of a learned or iterative process. For example, when two sequence entries are compared with each other users may have an opportunity to take advantage of how they relate to each other to improve the program functionality. Two entry sequences that are compared may have similarities and differences that become intimately involved in programming DNA sequence data. For example, in this case one sequence as relates to the other may allow for one entry to serve as the control sequence, which then provides an opportunity to use a biological programming language to compress DNA sequences based on the relative differences using biological instructions, such as described previously.

Where two sequences share sequence similarity, their differences usually have meaningful biological implications. In this case, a biological programming language may provide a unique advantage by using instructional operations relating to these changes in one sequence in comparison to the next. For example, the comparative analysis of two sequence entries with a specific set of biological instructions provides a way to organize these DNA sequences in a manner that is completely flexible and based on scientific knowledge.

A rearrangement of one region of the sequence with respect to another may be programmed based on the biological relevance. An insertion in one entry versus the next may have very different biological implications when the DNA recombination is as a result of a viral integration or a translocation event among chromosomal DNA. In this way, a biological programming language may allow a user to take advantage of scientific knowledge about the sequences that are being programmed. This may allow the language to be used as an analytical tool that, instead of comparing based purely on primary sequence information, alone allows further functional analysis. In this regard a biological programming language may use specific instruction sets that organize the DNA sequence data using scientific knowledge and biological relevance in combination with comparative sequence analysis.

The programming of two sequences as they relate to each other may become more powerful as a result of implementations of the processing and encoding described herein. By using biological knowledge to organize and relate two sequences, the capability to give biological intelligence to the data set may be provided.

Below are provided some additional examples for using an instructional approach to comparative analysis and description of two DNA sequences. This approach is not limited to DNA and RNA sequences but instead can be used to program lipids, polysaccharides, polypeptides and any other chemical or biological polymer. In the specific case of DNA, commonalities and differences in the biological sequence elements may be used to develop and enhance the scientific organization of the data for specialized processing. If the two sequences are identical, then the length and primary nucleotide base sequence of one need only be known, with the sequence of the other then known as well, and no instruction would be necessary.

In the case where two sequences are the same except for a single mutation event the second sequence can then be represented by a single instruction since the first sequence is known. This instruction, along with knowledge of the initial sequence, provides a scheme for a scientific description and compression of the two sequences. For example, the sequences may be:

Seq. #1.
(SEQ. ID NO. 9)
GGGGG GGGGG GGGGG GGGGG GGGGG GGGGG

Seq. #2.
(SEQ. ID NO. 10)
GGGGG GGGGG GGGGT GGGGG GGGGG GGGGG

Sequence 1 may be a polyG oligonucleotide that is 30 bases long while the second sequence is essentially the same with a single base change at position 15 (shown in BOLD above). Knowing the sequence and length of the first sequence, the second sequence can be represented with one simple instruction, such as:

Seq. #2. Transversion 15T

Accordingly, using one biological instruction it is known that there is a transversion at position 15 when compared with the first sequence (or a source or reference sequence). This also describes that all other positions are identical. We also know that position 15 was substituted with a T since the instruction is a transversion to a T and the source controlled sequence is a polyG oligo.

Now consider a third sequence (Sequence 3) that is 3,000 bases long:

Seq. #3
(SEQ. ID. NO. 11)

SEQ. ID NO.
21-2990
GGGGG GGGGG GGGGT GGGGG ------------ GGGGG GGGGG.

Here, the segment of Sequence 3 represented by the dashed line is a known sequence that belongs to a particular strain of the influenza virus (e.g., H1N1). When compared to the first sequence a second instruction may be used to represent the viral integration, such as:

Seq. #3. Try 15; Intgr 21 H1N1

If a comparison is made between Sequence 2 and 3, then Sequence 3 can be represented as:

Seq. #3. Intgr 21 H1N1

If the specific influenza strain is known, the entire nucleotide base sequence of Sequence 3 may be reconstructed from this instruction-based version.

Implementations of a genomic programming language can be used, for example, with a specific instruction set for description and in analysis with unique DNA sequence elements involved or associated with certain diseases. For example, the sex chromosome common to both males and females is the X chromosome. There is a gene on the long arm of the X chromosome where a CGG tandem repeat sequence in excess of a certain number can be a marker for a carrier of or diagnosis of a Fragile X Syndrome. Fragile X causes mental retardation with increasing severity proportionate with the increase in the number of tandem CGG repeats in the FMR1 gene. An example is shown below:

(SEQ. ID. NO. 12)

5'----------CGG CGG $(CGG)_{200}$ CGG CGG-----------3'

By using genomic programming language instructions for other features up to the Fragile X Mental Retardation 1 gene additional expansion instruction may be used for the triplet expansion, such as shown below.

Position relative; expn 200

Here, the dashes are indicative of the DNA sequence of the FMR1 gene upstream and downstream of the CGG expansion site in this gene. That is to say, when compared to the controlled or biological reference sequence this particular entity would use the instructions to describe features of this sequence on either side of the expansion region. Within the expansion site an expansion instruction would be invoked, such as:

Position relative; EXPN CGG 200 or

Repeat Triplet 200 (if, for example in this case 4 CGG was a normal condition).

In a second example of application specific DNA programming instruction sets and associated processing, splices may be considered. The mRNA transcripts of most human genes usually have introns that are spliced out in order to join the correct set of exons together. Sequence elements at splice donor and splice acceptor ends and highly conserved base sequence features of the introns are involved with splicing. During mRNA processing, the molecular environment regulates the splicing of the different exons in different tissues. Alternative splicing and expression of multiple combinations of exons is a way to build several variations of function sets from one gene. A DNA sequence may be programmed based on alternative splicing and the splicing code.

Defects in the alternative splicing process have been associated when comparing normal tissue exon expression and tissue from colon, bladder, prostate, and breast cancer, i.e., defects in the alternate splicing are indicators of these cancers. Using a set of instructional operations for splicing, the various alternative splice events may be accounted for. For example, highly conserved splice donor sequences for the expressed exon and splice acceptor end sequence may apply a jump instruction across introns and exons that are spliced out of the message, as shown in the example below:

Instruction for splice event #1
Splice 1, 2, 3
For splice event #2
Splice 1; Alt splice 2 (or splice jump exon 3)

Figure 9:
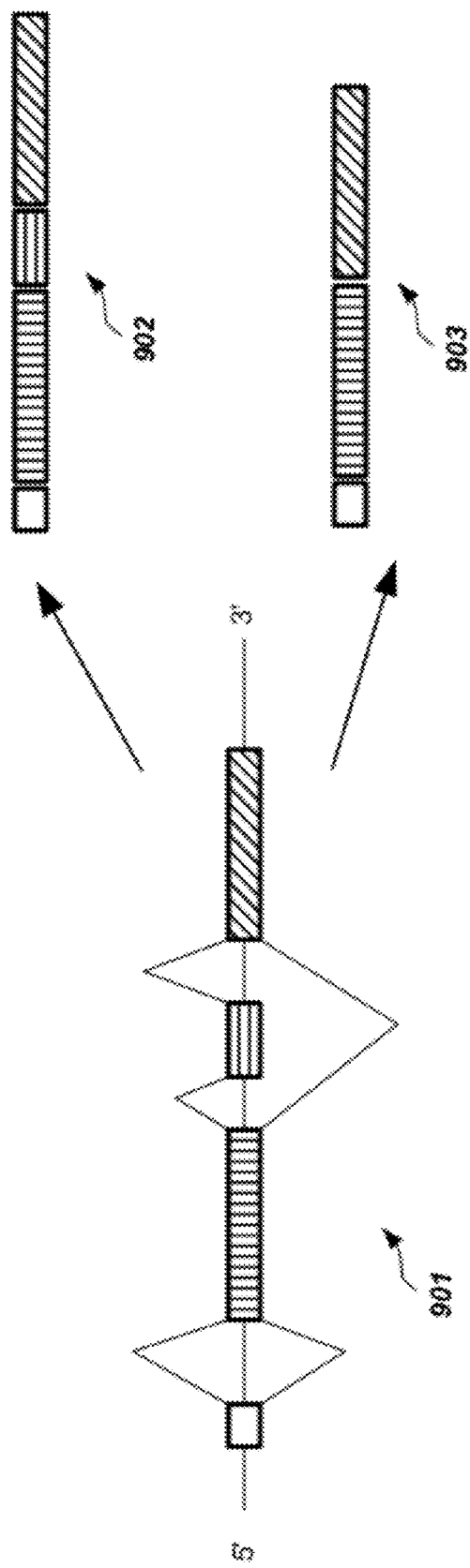
FIG. 9 illustrates details of example alternate splicing of mRNA.
Figure 10:
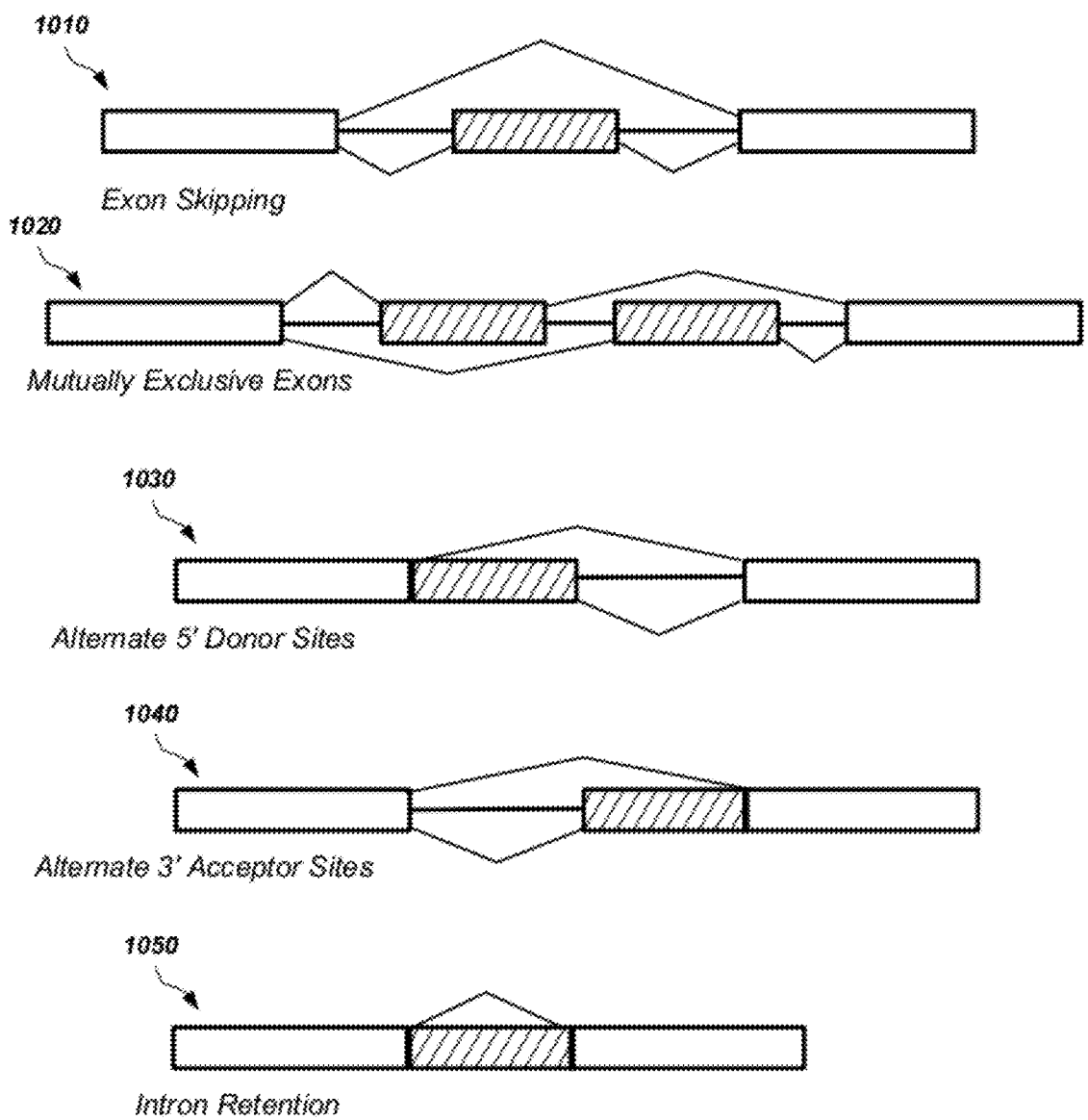
FIG. 10 illustrates details of examples of recombination.

Splice site donor is a highly conserved dinucleotide of sequence GC or GT. However the splice site donor GYNGYN is found across phylogenetic spectrum (where Y is C or T and N is any base). In addition to skipping exons, splice donors can occur within exons. A separate instruction may be used for this type of alt splice, in place of or in addition to the others. Examples are shown in FIG. 9 and FIG. 10, which are described in additional detail subsequently herein.

For example, looking at entry 6 and 7 below, it can be seen that besides position 3 changing from a G to a C, the third G in position 8 (highlighted in Entry 6) has been deleted in Entry 7.

```
Entry 6:
ACGTAGGGCATTGCA          (SEQ. ID. NO. 13)

Entry 7:
ACCTAGGCATTGCA           (SEQ. ID. NO. 14)
```

Figure 11:
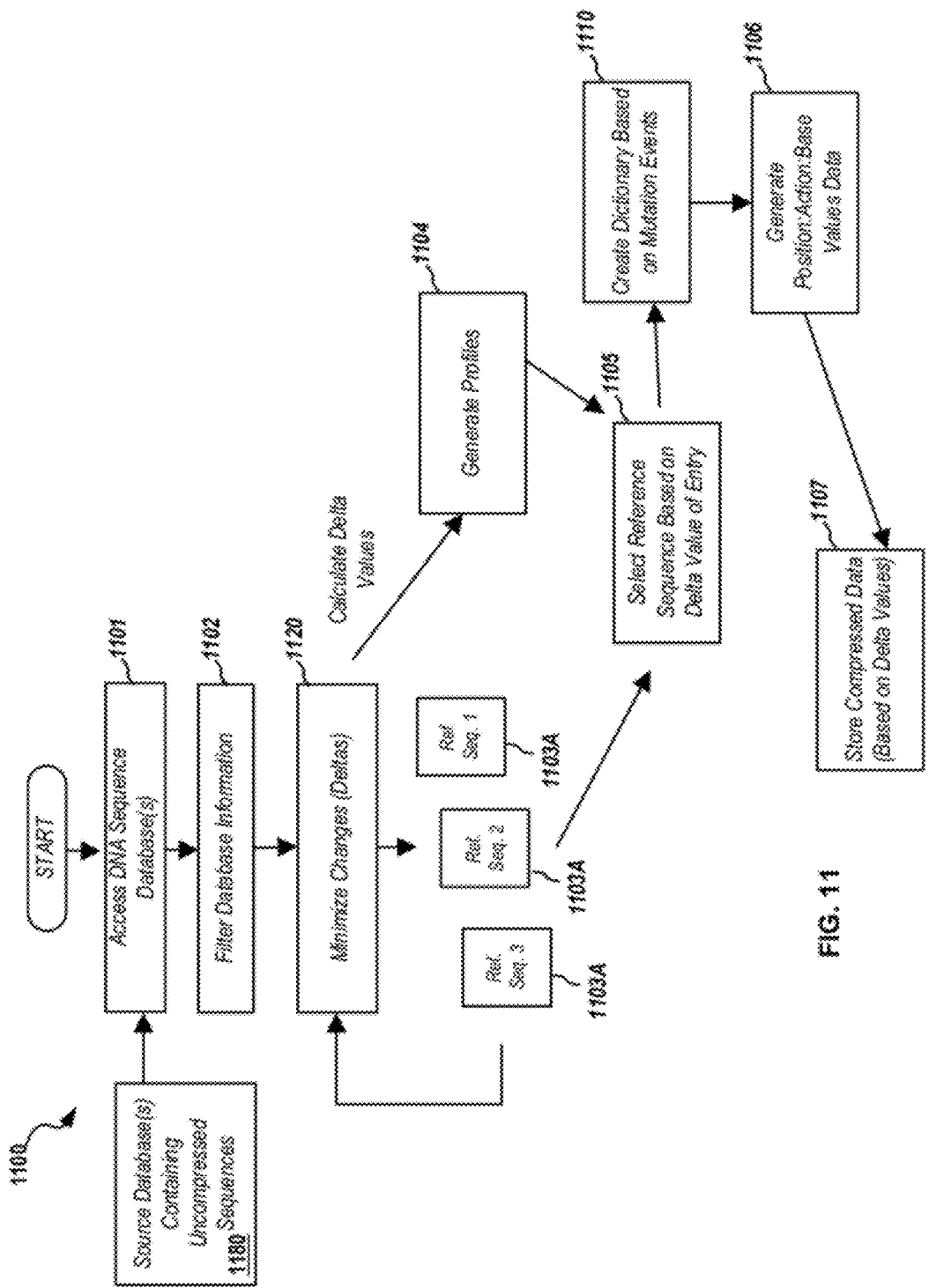
FIG. 11 illustrates an embodiment of a process for compressing of biological sequences.

The same procedure as described previously can be used, but additional information may also be added. For example, instead of having <position.value> being the delta information stored, <position.action.value> can alternately be stored. As an example, in one embodiment action may take the following values:
00->No operation/not used
01->Substitute the base value at the position address
10->Delete the base value at the position address
11->Insert the base value at the position address
100->Repeat the same nucleotide sequence starting at position up to value
101->Repeat and then invert the same nucleotide sequence starting at position up to value
110->Repeat the nucleotide base at position for value times
111->Reserved Attention is now directed to FIG. 11, which illustrates details of an embodiment of a process 1100 for compressing and storing sequence data using a delta database, such as database 1180. At stage 1101 a DNA sequence database contains data from an individual species; i.e. human genome DNA sequence. At stage 1102, the sequence entries in the source database may undergo a quick pre-processing procedure to determine two things: 1) Does this dataset fit the user's criteria for coding DNA based on threshold of similarity in the dataset? An example of a user defined criteria for DNA sequence instruction programming might be a predetermined maximum value for the highest variation value allowed for any one entry in the database against a selected minimum source sequence. Another example of the type of criteria that could be set by a user would be where the user is interested in operating on bacterial and viral DNA sequences only, in which case no entry in the database would be expected to be greater than the order of $10^7$ bases. 2) What are the most suitable minimum sequences that can be used for referencing based on these biological instructions? An experiment approach may be used to determine a best choice of a controlled source sequence. One approach to find a sequence for use in biological referencing is to run an alignment algorithm to determine which sequences have best correlation with the other sequences. For example, the sequences may be compared against each other and a Basic Local Alignment Search Tool (BLAST)-like algorithm may be run to determine the best average e-value. A BLAST algorithm finds regions of local similarity between sequences by comparing nucleotide or protein sequences to sequence databases and calculating the statistical significance of matches. A simple approach is to pick any sequence as the reference, run an algorithm to compress, and based on the results then make adjustments to the sequence, taking an iterative approach to the controlled source sequence refinement and purification.

It is expected that knowledge of the type of data contained within the database will be useful for determining suitability and efficacy of the instruction set format with regards to data structure. The degree of relative compression that can be achieved using this instructional approach may be directly related to the relatedness of sequence entries in the database. Therefore, for a database with a million entries of influenza virus or a particular human gene (BRCA1 for example) a known sequence for biological referencing could be selected. The minimum delta values for this may determine that a choice of sequence is suboptimal for a compressed organization of the dataset. Alternatively, a more suitable sequence can be generated or assigned as the source database is pre-processed. Using CAM allows fast and efficient parsing of databases with million deep entries.

It may be difficult to determine the number of sequences in a database that might serve as suitable sequences that can be used for referencing. In any case, any sequence that minimizes the minimum value could serve as a reference to compress, whether or not this sequence is an entry in the database. In addition, using databases with a million deep entries, depending on homology, multiple reference sequences may be used in programming for optimized organization of the dataset. As the data from the source database is streamed into a processing module, sequences may be aligned using a content addressable memory approach in the high speed data plane. This search and align routine may be useful for pre-processing and performing delta value calculations, and can be implemented in a single clock cycle in CAM.

At stage 1103A, a source or reference sequence for compression can be selected or assigned or generated based on maximum homology calculations or other calculations. This may be the same minimum difference value as a sequence of one entry in said database or a consensus of all the sequences or generated or assigned by an algorithm such as was described previously herein. Additional reference sequences may also be generated, such as in an iterative process. For example, at stage 1103B, a second biological reference sequence for the database may be generated or assigned based on a combination of the calculated difference values and biological relevance of the dataset for more suitable compression. For example, the data can first be preprocessed to determine if a certain SNP or change in RFLP (restriction enzyme fragment length polymorphism) or a set profile (variation) might be present in a large portion of the entries from said dataset. In this case the procedure may include returning to the original source sequence and making appropriate changes to accommodate variations.

At stage 1103C, yet another reference sequence for the database might be generated or assigned or selected in an application specific manner. If, for example, the source database contained tens of thousands or millions of complete human genomes, a controlled source might be selected based on the delta value within a certain region with known disease association where we can apply refined optimization techniques, while using the general purpose reference sequence for the rest of the genome. The use of more than one reference sequence for instruction-based compression processing may be dependent on how much sequence variation there is between initial reference sequence selected and the entries from the database with a high difference value. In addition, the cost of having a new reference sequence as a part of the instruction database may be a determinant of using multiple biological referencing sequences for compressing a single database.

At stage 1104, delta value determinations, along with the type of database may be used to profile the references. For example, if the database contains biomarker data from breast cancer patients only, then other genes that are expected, or predicted, or yet unknown, as well as those that are known to be associated with different forms of breast cancers in addition to BRCA1 would be present. The coding language use to program the database may seamlessly include large deletions and truncations and alternative splicing in BRCA1 (or other genes) that are known, predicted, expected or yet not known to be associated with early disease onset like massive tumors before age 30, or alternatively maybe these disease symptoms are known to be associated with hormonal changes that occur after first child as well. In this case, the deletion or truncation can be applied to the selected minimum controlled sequence as an updated version for more enhanced compression. Truncations are deletions at the 3' end of the gene, or in other words a premature termination codon (PTC) in the middle of the coding sequence resulting in a protein or polypeptide product with a shortened carboxyl terminus which usually does not function normally. This information may be saved for later use at stage 1106.

At stage 1105, a specific controlled source sequence may be used based on minimum delta values generated in a dictionary from the dataset, for example, for known mutation events in BRCA1 (not limited to any one gene) correlated with known clinical and/pharmacological effects. Each mutation event within each entry that results in a phenotypic effect, as well as silent mutations that are common in several entries, can be placed in a dictionary using this approach for further compression of the sequence data. As a result, processing may take advantage of specific difference values from the references that are common to multiple entries. Examples are shown below in Table 2.

TABLE 2

Hypothetical Example of BRCA Mutations With Clinical and Pharmacological Associations

| BRCA1 Mutations | Clinical Results | Pharmacological Effects |
| --- | --- | --- |
| G to A at Position 1286 | Multiple Small Tumors | Chemical X Inhibits Tumor Growth |

TABLE 2-continued

Hypothetical Example of BRCA Mutations With Clinical and Pharmacological Associations

| BRCA1 Mutations | Clinical Results | Pharmacological Effects |
| --- | --- | --- |
| Single Base Deletion at Position 932 | Positive Mammogram Result Before Age 25 | Chemical X not Effective, Highly Toxic Chemical A Low Toxicity, Low Efficacy |
| Alternative Splice Junction in the $3^{rd}$ Intron | Highly Aggressive | Chemical A Combined with Chemical Z Is Very Effective |
| Any Frame Shift Mutation Resulting in a Stop Codon Upstream of Position 1250 | Delayed Disease Onset | Chemical B is Most Effective Treatment |
| A to C at Position 547 | Most Common in Male Patients; Mild, Slow | Chemical M Effective and Nontoxic |

At stage 1106, a correlation table may be used. At this stage clinical and/or other pertinent data may be embedded in the position:instruction:destination value. Embedding data here may provide application specific compression. For example, mutation events with specific disease association or other phenotype can be coded, embedded and compressed along with the difference values in the database. At stage 1107, compressed DNA data may be stored based on selected controlled source sequence, inverse homology value, dictionary code, and other embedded data.

In addition, dictionary processing may be used, such as described previously herein. This may be based on, for example, common addresses, sized, distances or other redundancies in instruction data. Mutation events may be used as a basis in some implementations.

Figure 12:
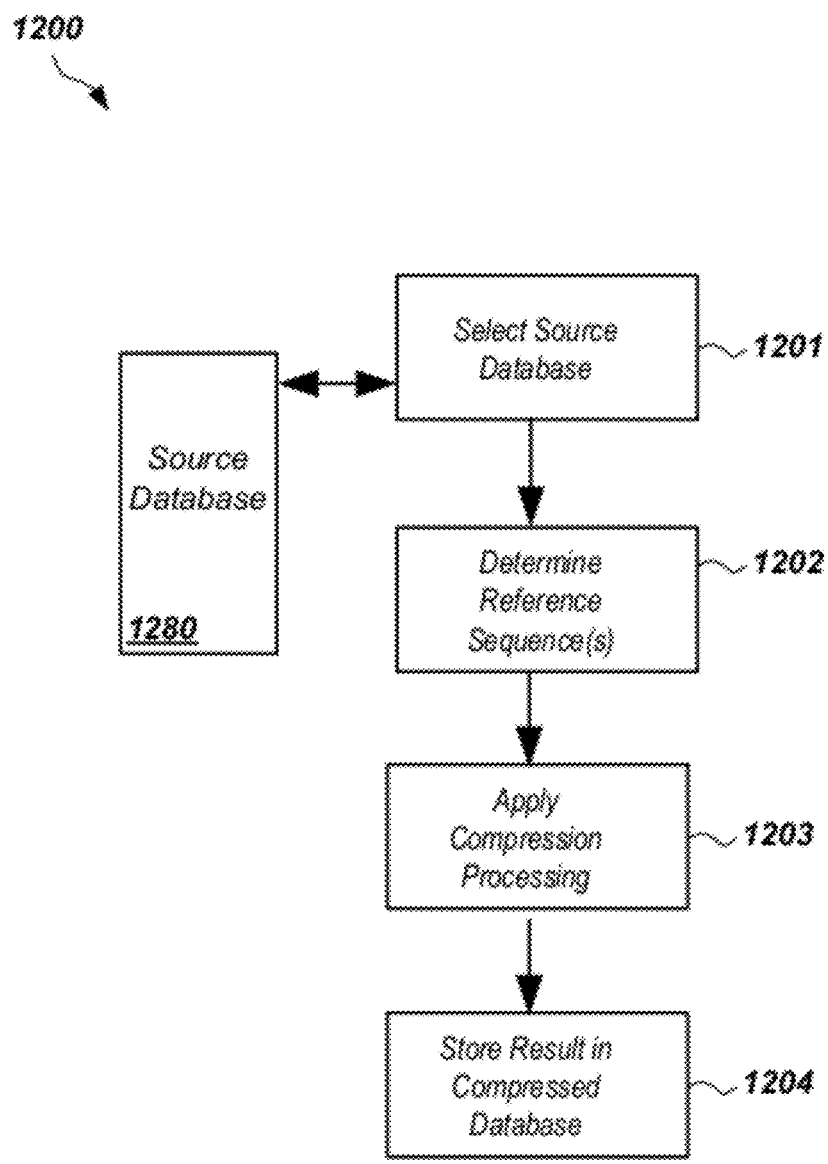
FIG. 12 illustrates an embodiment of a process for compressing of biological sequences.

Attention is now directed to FIG. 12, which illustrates details of one embodiment of a process 1200 in accordance with aspects of the present invention. At stage 1201, a database of DNA sequence data may be obtained or accessed. As an example, a large DNA sequence database may contain data from canine cancers, horse breeder data, or other animal sources. The method is not limited to any certain type of DNA data, however, the approach may be particularly effective for large database of a single species or high homology sequences. The source database may be accessed, with the data screened to meet the criteria for similarity. This preprocessing may include matching and aligning sequences in the source database. In addition, calculations for difference values and tracking of position and actions may be carried out here.

At stage 1202, a minimum reference sequence determination may be made using the delta value and other related data. At stage 1203, instruction-based compression processing, such as described previously herein, may be applied. The compression processing may take the standard DNA sequence data and converts it to a language format that is useable by a chip or other processing mechanism, which may be based on an instruction set as described previously. At stage 1204, the data stored in the compressed form retains all the information form the original sequence, and may also include other information, such as metadata. In some embodiments, this compressed format may be visible or usable only by a processing chip and/or other processing hardware, and may not be made readily available to a user.

In various embodiments, aspects of the present invention may be implemented on a computer system or systems, or may be implemented in specific semiconductor devices such as chips or chipsets or on other devices such as ASICS, programmable devices such as FPGA, or in other configurations.

Attention is now directed to FIG. 13, which illustrates one example embodiment of a computer system 1300 configured to perform biological sequence processing as described herein. System 1300 includes one or more processors 1310, along with a memory space 1370, which may include one or more physical memory devices, and may include peripherals such as a display 1320, user input output, such as mice, keyboards, etc (not shown), one or more media drives 1330, as well as other devices used in conjunction with computer systems (not shown for purposes of clarity).

System 1300 may further include a CAM memory device 1350, which is configured for very high speed data location by accessing content in the memory rather than addresses as is done in traditional memories. In addition, one or more databases 1360 may be included to store data such as compressed or uncompressed biological sequences, dictionary information, metadata, or other data or information, such as computer files. In an exemplary embodiment one or more of the databases 1360 store data containers structured to contain and facilitate the processing of biological data units. Databases 1360 may be implemented in whole or in part in CAM memory 1350 or may be in one or more separate physical memory devices.

System 1300 may also include one or more network connections 1340 configured to send or receive biological data, sequences, instruction sets, or other data or information from other databases or computer systems. The network connection 1340 may allow users to receive uncompressed or compressed biological sequences from others as well as send uncompressed or compressed sequences. Network connection 1340 may include wired or wireless networks, such as Etherlan networks, T1 networks, 802.11 or 802.15 networks, cellular, LTE or other wireless networks, or other networking technologies are known or developed in the art.

Memory space 1370 may be configured to store data as well as instructions for execution on processor(s) 1310 to implement the methods described herein. In particular, memory space 1370 may include a set of biological sequence processing modules including modules for performing processing functions including reference sequence generation, in module 1380, instruction generation and instruction-based sequence compression, in modules 1382 and 1390, dictionary processing, in module 1384, metadata receipt, processing, and transmission, in module 1386, data integration, in module 1388, as well as other functions in associated modules (not shown). Instruction module 1390 may be included to provide specific functionality associated with instruction selection and processing as described previously herein.

The various modules shown in system 1300 may include hardware, software, firmware or combinations of these to perform the associated functions. Further, the various modules may be combined or integrated, in whole or in part, in various implementations. In some implementations, the functionality shown in FIG. 13 may be incorporated, in whole or in part, in one or more special purpose processor chips or other integrated circuit devices.

Figure 14:
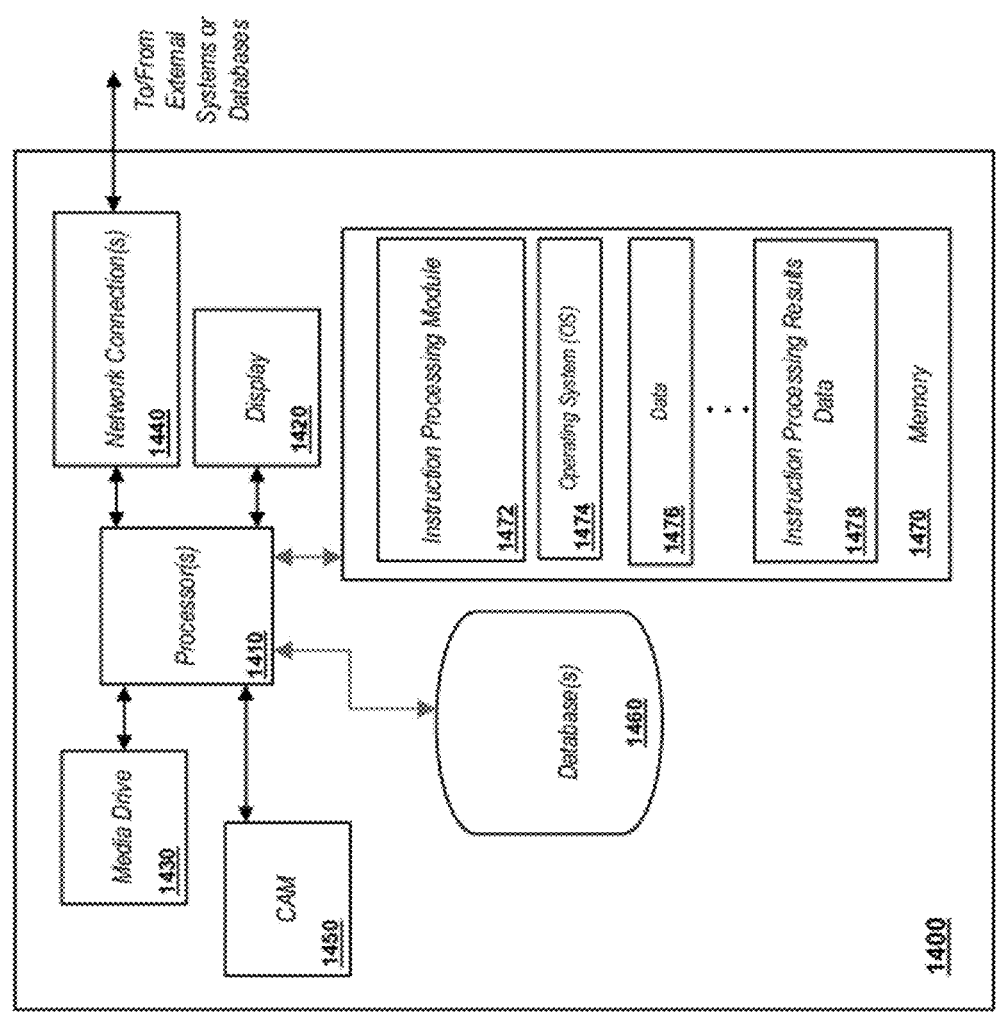
FIG. 14 illustrates an embodiment of a system for processing biological sequence data.

Attention is now directed to FIG. 14, which illustrates an example embodiment of a computer system 1400 configured to perform biological sequence processing using instructions as described herein. System 1400 may, for example, be used to implement a method for processing biopolymeric information, the method comprising receiving a sequence of binary codes representative of a biopolymeric data sequence and processing the sequence of binary codes using a plurality of instructions, each of the plurality of instructions being at least implicitly defined relative to at least one controlled sequence and representative of a biological event affecting one or more aspects of a biopolymeric molecule.

System 1400 includes one or more processors 1410, along with a memory space 1470, which may include one or more physical memory devices, and may include peripherals such as a display 1420, user input output, such as mice, keyboards, etc (not shown), one or more media drives 1430, as well as other devices used in conjunction with computer systems (not shown for purposes of clarity).

System 1400 may further include a CAM memory device 1450, which is configured for very high speed data location by accessing content in the memory rather than addresses as is done in traditional memories. In addition, one or more databases 1460 may be included to store data such as compressed or uncompressed biological sequences, dictionary information, metadata or other data or information, such as computer files. In an exemplary embodiment one or more of the databases 1460 store data containers structured to contain and facilitate the processing of biological data units. Database 1460 may be implemented in whole or in part in CAM memory 1450 or may be in one or more separate physical memory devices.

System 1400 may also include one or more network connections 1440 configured to send or receive biological data, sequences, instruction sets, or other data or information from other databases or computer systems. The network connection 1340 may allow users to receive biological data units and/or uncompressed or compressed biological sequences from others as well as send biological data units and/or uncompressed or compressed sequences. Network connection 1340 may include wired or wireless networks, such as Etherlan networks, T1 networks, 802.11 or 802.15 networks, cellular, LTE or other wireless networks, or other networking technologies are known or developed in the art.

Memory space 1470 may be configured to store data as well as instructions for execution on processor(s) 1410 to implement the methods described herein. In particular, memory space 1470 may include a set of biological sequence processing modules including modules for performing instruction-based processing functions as described herein. Instruction module 1490 may be included to provide specific functionality associated with instruction selection and processing including receiving a set of data including instruction set coding and providing information associated with the instruction set codes. The information may be based on comparing the instruction-set encoded information with other instruction-set encoded information or non-encoded sequence data or other data or information. The various modules shown in system 1400 may include hardware, software, firmware or combinations of these to perform the associated functions. Further, the various modules may be combined or integrated, in whole or in part, in various implementations. In some implementations, the functionality shown in FIG. 14 may be incorporated, in whole or in part, in one or more special purpose processor chips or other integrated circuit devices.

Additional Details of Embodiments of DNA Sequence Compression Architectures

In one implementation, compressed biological sequences include embedded metadata along with mutation events that are compressed with the sequence. In one embodiment, a method for compression includes a step where DNA sequence data is acquired from a source database in a standard format, such as the FASTA format, and is converted to a binary format and coded using biological instructions.

This approach may allow for streaming of the DNA data as it is converted from the standard format to a binary format. As the data streams in, the entries may be aligned and searched and processed in a CAM using the following approach. Initially, a source database may be selected where the entries are from the same species or have high sequence homology. Initially one entry from the source database or elsewhere may be selected. In other implementations, the reference sequence may be adjusted or additional reference sequences added after a dictionary analysis stage.

Once a reference sequence or sequences is selected, instruction-based compression may be applied as described herein against sequences in the source database. Based on results from initial compression processing, which may include difference values and the commonality of deltas among individual entries, a dictionary algorithm may be applied to further compress the database and also to determine if further compression may be achieved by updating or replacing the minimum controlled sequence. Finally, monitor the count of reference to dictionary entries may be monitored to determine if the reference sequence(s) should be updated. This may be done in an iterative fashion of reference sequence refinement that may be used to optimize the degree of compression.

Various embodiments may include one or more of the below described features, which may be inter-combined in various ways. Typical embodiments include machine language-like instruction with opcodes associated directly with biological sequences for the purpose of, but not limited to processing, transporting and classifying of biological sequences. A machine language is defined by, but not limited to, a set of instruction set (i.e. ISA—Instruction Set Architecture) that defines a part of the computer architecture related to programming. This may be defined for a specialized processor configured to optimally process biological instructions as described herein. The instruction set may include of group instructions including, but not limited to, biological relevance instructions of operations performed directly or indirectly on to the biological sequences in addition to, but not limited to native, operative and constructive data types, registers and its manipulations instructions, various addressing modes instructions including but not limited to absolute mode (i.e., direct, indexed, base plus indexed etc.), simple mode (i.e. register based, based plus offset, immediate, implicit and PC-relative), register indirect and sequential mode, interrupt and exception handling instructions and external I/O instructions. Macro instructions that consist of combinations of two or more instructions as described above to perform additional processing of biological sequences may also be used. Macro instructions may be used to create high level languages similar but not limited to C, C++ languages as well as object and service oriented languages tailored to processing of biological sequences.

Embodiments may include a micro-instruction set that is specifically designed for, but not limited to, semiconductor chip architecture including System-on Chip (SoC). Microinstructions (and/or microcode) are a set of instruction code layered between machine language code and application specific architecture of the chip. These instructions may allow to manipulation of biological sequences to provide optimal processing power based on internal chip architecture that typically includes, but is not limited to, memory architecture, register architecture, I/O and other hard coded algorithmic processing elements.

Some embodiments may use multiple optimized reference sequences to derive a difference value to be used to store a plurality of related sequences as a delta of the reference. This may include combining minimum sequence and delta values with a second set of data containing clinical, pharmacological and/or disease association data. Difference values and biological programming instruction values may be stored as a source catalog to be used for processing/parsing/sorting and compression of sequence data. Reference sequences may be updated based on iterative refinement and optimization of reference sequences using biological instructions based on mutation events that are common or otherwise related to a large portion of entries in a source database. Some embodiments may use application specific instructional programming for sequence compression and processing based in biology for known, unknown and predicted mutation and disease association.

Some embodiments may relate to programming of DNA sequence data based in biological instructions and any delta value in addition to nucleotide based on differences between entries and minimum sequences such as but not limited to, for example, base modifications (i.e. methylation, carboxylation, formylation, deamination, base analogs, etc) or structural deltas (i.e. DNA packaging; chromatin structure, heterochromatin structure, etc) or charge of partial dipolar moment or any other way to measure the difference and or homology between two entries. A programming DNA language may address mutational events in nucleic acid sequences (DNA and RNA) and amino acid sequences in protein and other polymeric molecules. Programming instructional coding may be used to address chromosomal rearrangement such as but not limited to large deletions, insertions, gene duplications, inversions and any other such related type of translocation events. Instructional operations may be used to articulate changes between and or within nucleic acid sequences including but not limited to triplet expansions in disease associations.

A biological instruction coding architecture and instruction set may be used to articulate changes between and or within nucleic acid sequences included but not limited to alternative or constitutive splicing and any known, unknown or predicted alteration in any cis-acting and or trans-acting nucleic acid or protein sequence element in disease association. Biological instruction coding may be used to articulate changes between and/or within and among nucleic acid sequences, including, but not limited to, alternative or constitutive splicing and any known, unknown, yet to be determined, or predicted alteration in any cis-acting and/or trans-acting nucleic acid or protein sequence element in gene activation, exon expression, inclusion or skipping and or disease association.

Some embodiments may include a nucleic acid programming language that can be utilized for determination of insertion element origins as related to sequences such as extraneous bacterial and or viral sequences and other such transposable elements relates to gene expression and regulation. The programming language may be configured to discriminate nucleic acid sequence insertions between DNA from microbial agents from disease causing or non disease causing origins and rearranged or shuffled genomic sequences. Some embodiments may include a biological instruction set that can enable a comparative description between two functionally or structurally related or unrelated sequences. Biological instructions may be used to operate on nucleic acid sequence data that can be used as a source of comparative analysis of sequences that are related and similar or unrelated and share little or no similarity. A programming language may use a set of instructions such as described herein, but not limited to those described herein, and to include a biological, structural, chemical or any other type of relevant or irrelevant nucleic acid sequence element for purposes of comparison, alignment, assemble, analysis, or any other related or unrelated sequence analysis and or processing. An instructional programming language may be used with any sequential element whether biologically relevant or arbitrary sequence elements used for processing and/or analysis of related or unrelated sequences.

Representation of Polymeric Sequence Data Using Biological Data Units

In one aspect the present disclosure describes an innovative methodology for biological sequence manipulation well-suited to address the difficulties relating to the processing of large quantities of DNA sequence data. The disclosed methodology enables packetized representations of such sequence data to be efficiently stored (either locally or in a distributed fashion), searched, moved, processed, managed and analyzed in an optimal manner in light of the demands of specific applications.

The disclosed method involves breaking DNA sequence entries into fragments and packetizing the fragments using BioIntelligent™ biologically-relevant header information to form biological data units. In one embodiment much of the BioIntelligent™ biologically-relevant header information would be obtained from public databases such as, for example, GenBank or EMBL. The DNA sequence entries within many public databases are stored in a FASTA format, which accommodates the inclusions of annotated information concerning the sequence. For example, an entry for a DNA sequence recorded in the FASTA format could include annotated information identifying the name of the organism from which the DNA was isolated and the gene or genes contained in the specific sequence entry. In addition, information concerning from which chromosome the DNA was obtained and the starting and ending base positions of the sequence would also typically be available. Furthermore, other databases include information relating to, for example, the location of human CpG islands and their methylation, as well as the genes with which such islands are associated (see, e.g., http://data.microarrays.ca/cpg/index.htm).

Database entries identified as being associated with RefSeqGene, a project within NCBI's Reference Sequence (RefSeq) project, provide another potential source of BioIntelligent™ biologically-relevant header information. RefSeqGene defines genomic sequences of well-characterized genes to be used as reference standards. In particular, sequences labeled with the keyword RefSeqGene serve as a stable foundation for reporting mutations, for establishing conventions for numbering exons and introns, and for defining the coordinates of other biologically significant variation. DNA sequence entries in the RefSeqGene set will be well-supported, exist in nature, and, to the extent for which it is possible, represent a prevalent, 'normal' allele.

It should be appreciated that there may be different schemas for packetizing sequence entries. For example, in the case in which it is suitable to fragment sequence entries into packets of genes or, alternatively, into introns and exons, relevant data is available for placement into the BioIntelligent™ biologically-relevant headers of the biological data units containing such sequence fragments.

Biological Data Units Including BioIntelligent™ Biologically-Relevant Headers

Referring again to FIG. 15, the BioIntelligent™ biologically-relevant header 1510 is seen to include a number of fields containing information of biological relevance to the DNA sequence data within the payload 1520 of the biological data unit 1500. It should be appreciated that FIG. 15 provides only an exemplary representation of the type of biologically relevant information which may be included within a BioIntelligent™ biologically-relevant header. Accordingly, including other types of information within a BioIntelligent™ biologically-relevant header or the equivalent, however represented, is believed to be within the scope of the present disclosure. In addition, although the following generally describes information as being contained or included within various sections of the BioIntelligent™ biologically-relevant header 1510, it should be understood that in various embodiments such headers may contain pointers or links to other structures or memory locations storing the associated header information. Similarly, the payload 1520 may contain a representation of the segmented DNA sequence data of interest, or may include one or more pointers or links to other structures or locations containing a representation of such sequence data.

A first section 1501 of the BioIntelligent™ biologically-relevant header 1510 provides information concerning CpG methylation levels and positions in and at various positions in the DNA sequence segment included within the payload 1520 of the biological data unit 1500. Identification of these CpG islands and the level of methylation pattern will likely play an important role in understanding regulation of the associated genes and any involvement with diseases.

The header 1510 also includes a chromosome banding pattern section 1502 containing information concerning any chromosomal rearrangement known, yet unknown and or predicted to be involved with any disease onset. These types of cytogenetic abnormalities are often associated with severe phenotypic effects.

Header sections 1503 and 1504 provide information identifying the beginning and ending positions for the exons that are contained in the DNA sequence segment included within the payload 1520. Since exon selection has tissue or cell type specificity, these position may be different in the various cell types resulting form a splice variant or alternative splicing. Along with this DNA coding information for individual exons, header section 1505 contains a count of the number of exons contained in the DNA sequence segment included within the payload 1520.

Header section 1506 will represent DNA sequence fragments within payload 1520 having some association with a disease will be represented by the information in section 1506. Information on molecular pathways or systems that may involve other genes or gene products would also described within this section of the BI header. Alternatively, since mutation of a certain gene could be involved in several diseases, such information would also generally be contained within header section 1506.

To the extent the DNA sequence segment in the payload 1520 contains a gene or plurality of genes, then header section 1507 provides information concerning the applicable gene name or gene ID. Header section 1508 specifies the tissue or cell type relevant to the expression of the various exons described in section 1505.

Header section 1509 will provide information concerning all open reading frames present within the segmented DNA sequence data within the payload 1502. Header section 1510 and 1511 specify the start and end positions of the DNA sequence segment represented with the payload 1502. Section 1512 indicates if the segmented DNA sequence data within the payload 1502 chromosomal or mitochondrial. Furthermore, section 1513 provides information concerning the genus and species of the origin of the DNA sequence segment represented with the payload 1502.

The header 1510 will generally contain information relating to other aspects of the DNA sequence as it is sorted, filtered and processed. This packetized structure of the DNA sequence data represented in bits and encapsulated with BioIntelligent™ biologically-relevant headers and other relevant information advantageously facilitates processing by network elements operative in accordance with layered or stacked protocol architectures.

Figure 17:
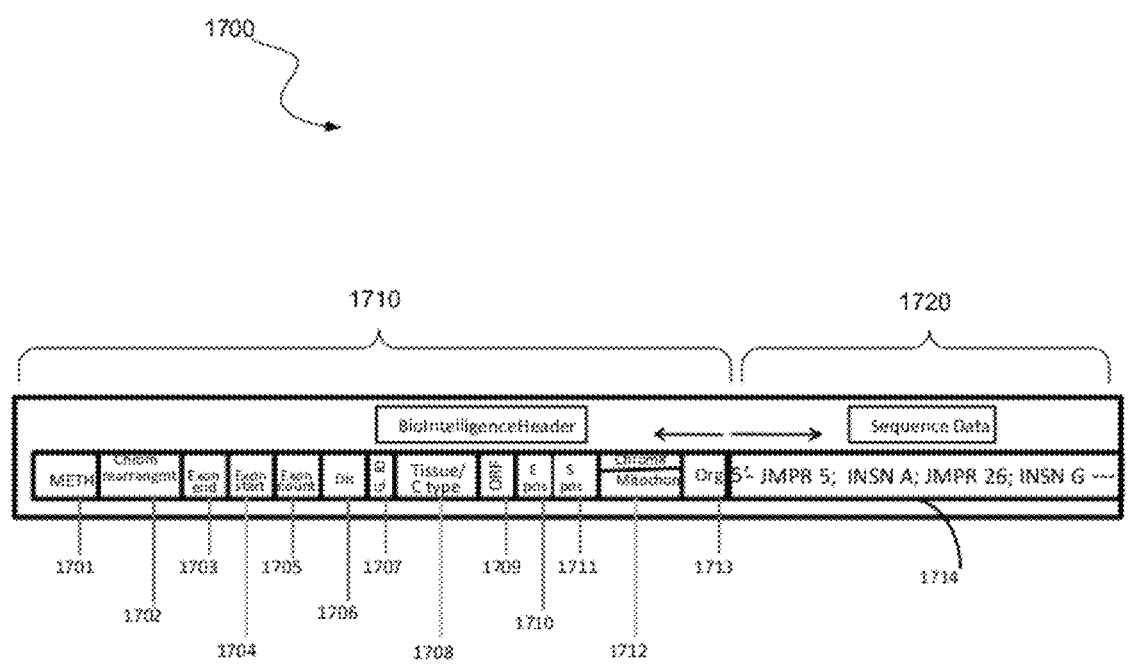
FIG. 17 depicts a biological data unit having a BioIntelligent™ biologically-relevant header and a payload containing an instruction-based representation of segmented DNA sequence data.

Attention is now directed to FIG. 17, which depicts a biological data unit 1700 having a BioIntelligent™ biologically-relevant header 1710 a payload 1720 containing an instruction-based representation of segmented DNA sequence data. Such an instruction-based representation is discussed above and in the copending '234 application. Although the content and representations of the payloads 1510 and 1710 differ, the same type of information is included within the BioIntelligent™ biologically-relevant headers 1510 and 1710 of the biological data units 1500 and 1700, respectively.

The packetizing of segmented DNA sequence data and the embedding of biologically relevant information in biological data units will enable development a networked processing architecture within which such data may be organized and arranged in a layered format. Such an architecture is believed suitable for effecting rapid analysis of large amounts of data of this type.

In one approach, the headers of such biological data units are used to qualify or characterize the fragmented or otherwise segmented DNA sequence data included within the payloads of such data units. In so doing, biological data units containing segmented DNA sequence data or other sequence data may now be sorted, filtered and operated upon based on the associated information contained within the headers of the data units. For example, a database containing biological data units incorporating segmented DNA sequence data and header information similar to that associated with the header 1510 of FIG. 15 may be quickly and efficiently sorted in accordance with parameters defined by an application. In other words, the same segment of DNA may be sorted and analyzed in several different ways by using the header information associated with, or otherwise directly or indirectly linked to, the payload representation of the segment.

It is anticipated that it would be beneficial to arrange and represent the genomic sequence information from many different organisms, e.g., from bacteria to humans, in accordance with the layered data architecture illustrated in FIG. 16. For example, consider the case in which a single segment of a DNA sequence data of interest is included within the payload of a biological data unit inside of a data container which includes biological data units associated with DNA sequence data of other organisms. Consider further that if, for example, the DNA sequence data of interest was a particular variant of a human gene associated with breast cancer, such as BRCA1, then such data could be extracted from the container by filtering the contents of the data container for biological data units associated with DNA sequence data from the organism *homo sapiens*. The data unit(s) containing the specific BRCA1 variant along with all other DNA data packets containing human DNA sequence data would be extracted. However, sorting human DNA sequence data from the DNA sequence data from other organisms may be insufficient in view of the requirements of certain applications. Accordingly, further processing could be performed in which biological data units containing sequence data from human chromosome 17 would be extracted from the data container.

Biological data units having payloads containing DNA sequence fragments from chromosome 17 may provide a reasonable level of filtering. However, in order to efficiently analyze the gene most notably associated with breast cancer, further processing, sorting and filtering may be necessary. This may be achieved by calling for the specific start and end positions on the chromosome (S pos and E pos) or the gene ID (GID) or by disease, breast cancer. However, if the biological data unit being sorted contains sequence data associated with an alternately-spliced variant of BRCA1, then this information may be contained in the header information containing the total exon count (see, e.g., header section 1505 of FIG. 15), in addition to within the header sections including start exon and end exon information sections (see, e.g., header sections 1503 and 1504). Furthermore, additional information from concerning tissue or cell type may need to be provided in order to extract biological data units associated with a specific BRCA1 variant.

The packetized structure of the disclosed biological data units further enable representation of layered data models such as that depicted in FIG. 16. In particular, each header forming part of or linked to a particular biological data unit may be associated with a specific layer of the model. One advantage of using a layered data model is that data from the various layers may interrelate during processing of the header information included within the set of biological data units being evaluated or otherwise analyzed. For example, in the exemplary case described above, information from the RNA-specific model layer relating to the splicing of introns from pre-mRNA was used to identify BRCA splice variants, thereby correctly facilitating determination of exon start and end positions.

The use of BioIntelligent™ biologically-relevant headers consistent with a layered data architecture also advantageously enables substantial changes made to the information associated with one layer of the model without necessitating that corresponding modifications be made to other layers of the model. For example, mutations at splice donor and splice acceptor sites may change the splicing pattern and mRNA size, protein structure, and function, and these changes may be accommodated and mapped back to the DNA layer without requiring that corresponding changes be made to BioIntelligent™ biologically-relevant header information associated with the DNA layer.

DNA Sequence Data for Data Unit Payloads

Figure 18A:
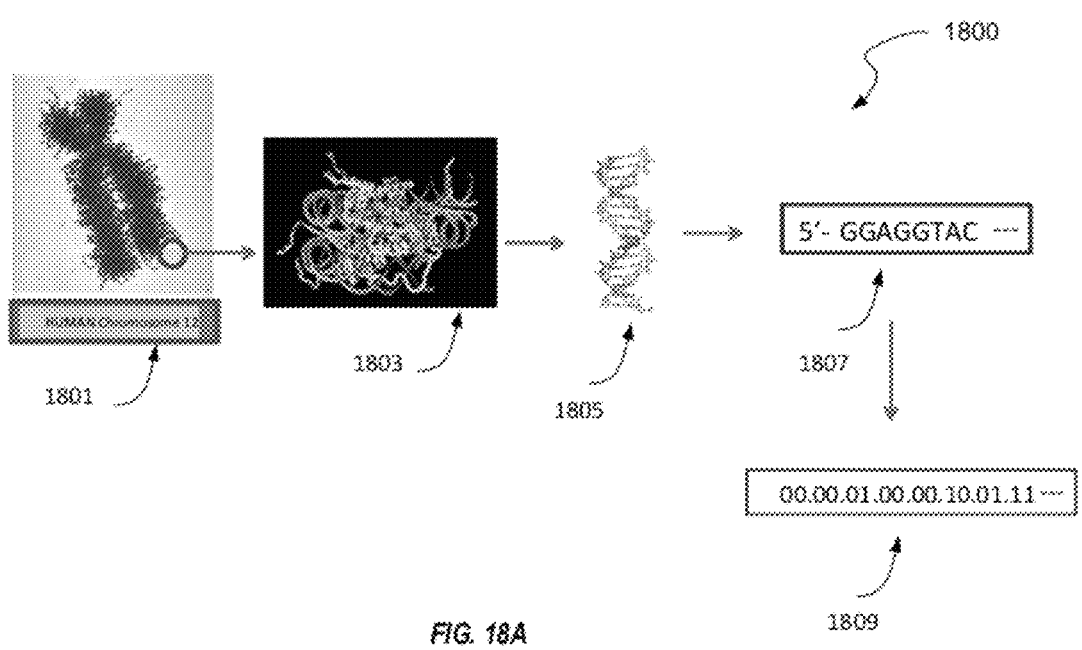
FIG. 18A depicts a representation of source DNA sequence data capable of being segmented in the manner described herein to provide segmented DNA sequence data for inclusion within biological data units.

Attention is now directed to FIG. 18A, which illustratively depicts a representation of source DNA sequence data capable of being segmented in the manner described herein to provide segmented DNA sequence data for inclusion within biological data units. As shown in pane 1801, the billions of base pairs of the human genome are arranged in segments as 23 sets of chromosomes. This organizational state is somewhat dynamic and involves the possibility of major chromosomal rearrangements as well as deletions, insertions and duplications. However, the use of chromosome number as a reference for packetizing manageable fragments of DNA sequence data for analysis will be a useful and suitable source of information for the BI header.

Pane 1801 provides a picture of an electron micrograph of a human chromosome 12 with the double stranded DNA. The double stranded DNA is organized in a higher order structure that involves DNA binding proteins called histone proteins in units known as chromatins, as is graphically represented in pane 1803. Chemical modification of these and other DNA binding proteins such as methylation and acetylation play a critical role in expression of the genes in these regions of the chromosome.

Attention is now directed to pane 1805, which shows the unbound double-stranded DNA. As is known, DNA can be isolated and represented as a sequence of the nucleotide bases G, A, T and C. Such a representation of a DNA sequence in the FASTA format is provided in pane 1807. In particular, pane 1807 illustrates the sequential relationship of the four bases from the 5' to the 3' end.

Processing consistent with the teachings herein may be facilitated by transforming the DNA sequence data represented in the FASTA format into a binary representation (e.g., a 2-bit representation) as shown in pane 1809; that is, each nucleotide base is uniquely represented by a 2-bit binary number. In one implementation, all or a portion of this 2-bit sequence representation comprises the payload of a biological data unit encapsulated with one or more BioIntelligent™ biologically-relevant headers. Using this novel method, the FASTA sequence format is converted to a bit-encoded format and knowledge fields or annotations or metadata are added as headers.

In order to provide a reference for the type of scientific information capable of being used to define BioIntelligent™ biologically-relevant headers, set forth below is an example of a nucleic acid sequence entry previously from the GenBank at NCBI. It should be understood that the exemplary entry below in no way limits the scope or type of data which may be included within the BioIntelligent™ biologically-relevant headers of a biological data unit, nor the source of such data. The exemplary sequence entry relates to the gene BRCA1, which is known to be associated with early onset breast cancer in humans.

```
                       EXEMPLARY SEQUENCE ENTRY
Homo sapiens clone mck43_A neighbor of BRCA1 gene 1 (NBR1) gene, partial cds; and
hypothetical protein LOC10230 (NBR2) and breast cancer 1 early onset (BRCA1) genes,
complete cds GenBank: DQ190454.1
LOCUS       DQ190454      150582 bp   DNA   linear   PRI 24-SEP-2005

DEFINITION Homo sapiens clone mck43_A neighbor of BRCA1 gene 1 (NBR1) gene, partial cds; and
hypothetical protein
LOC10230 (NBR2) and breast
     cancer 1 early onset (BRCA1) genes, complete cds.
ACCESSION   DQ190454
VERSION     DQ190454.1 GI:75874870
KEYWORDS    .
SOURCE      Homo sapiens (human)
ORGANISM    0
             Eukaryota; Metazoa; Chordata; Craniata; Vertebrata; Euteleostomi;
             Mammalia; Eutheria; Euarchontoglires; Primates; Haplorrhini;
         Catarrhini; Hominidae; Homo.
REFERENCE  1 (bases 1 to 150582)
AUTHORS    Raymond,C.K., Paddock,M., Subramanian,S., Deodato,C., Zhou,Y.,
           Haugen,E., Kaul,R. and Olson,M.V.
TITLE      Direct Submission
JOURNAL    Submitted (01-SEP-2005) Genome Center, Department of Medicine,
           University of Washington, Box 352145, Seattle, WA 98195, USA
FEATURES             Location/Qualifiers
     source          1..150582
                     /organism="Homo sapiens"
                     /mol_type="genomic DNA"
                     /db_xref="taxon:9606"
                     /chromosome="17"
                     /clone="mck43_A"
     gene            complement(<259..>14273)
                     /gene="NBR1"
     mRNA            complement(join(<259..473,942..1019,3617..3811,
                     9250..9272,10655..10673,12069..12131,14172..>14273))
                     /gene="NBR1"
                     /product="neighbor of BRCA1 gene 1"
     CDS             complement(join(<259..473,942..1019,3617..3811,
                     9250..9272,10655..10673,12069..12131,14172..14273))
                     /gene="NBR1"
                     /codon_start=1
                     /product="neighbor of BRCA1 gene 1"
                     /protein_id="ABA29222.1"
                     /db_xref="GI:75874873"
                     /translation="MEPQVTLNVTFKNEIQSFLVSDPENTTWADIEAMVKVSFDLNTI
                     QIKYLDEENEEVSINSQGEYEEALKMAVKQGNQLQMQVHEGHHVVDEAPPPVVGAKRL
                     AARAGKKPLAHYSSLVRVLGSDMKTPEDPAVQSFPLVPCDTDQPQDKPPDWFTSYLET
                     FREQVVNETVEKLEQKLHEKLVLQNPSLGSCPSEVSMPTSEETLFLPENQFSWHIACN
                     NCQRRIVGVRYQC"
                     (SEQ. ID NO. 15)
     gene            complement(<50107..>51338)
                     /gene="NBR2"
     mRNA            complement(join(<50107..50262,51156..>51338))
                     /gene="NBR2"
                     /product="hypothetical protein LOC10230"
```

EXEMPLARY SEQUENCE ENTRY

```
CDS       complement(join(50107..50262,51156..51338))
          /gene="NBR2"
          /note="neighbor of BRCA1 gene 2"
          /codon_start=1
          /product="hypothetical protein LOC10230"
          /protein_id="ABA29221.1"
          /db_xref="GI:75874872"
          /translation="MWKGGRSHPFLPCSSRRAGSGGQLDSILPHQSPAWGPWGCKDLS
          SGVPSFLTSSILWKSAVFAEDNGLKIHLCSYKRDDLVLFYDCTSFVLTFGPSPWFLTQ
          GFLNPLEFSA"
          (SEQ. ID NO. 16)
gene      <65982..>144405
          /gene="BRCA1"
mRNA      join(<65982..66061,74300..74353,83548..83625,
          85125..85213,85820..85959,90198..90303,92789..92834,
          94157..94233,95219..98644,99047..99135,107504..107675,
          113466..113592,115559..115749,118842..119152,
          122387..122474,126131..126208,126709..126749,
          132947..133030,138965..139019,140888..140961,
          142379..142439,144281..>144405)
          /gene="BRCA1"
          /product="breast cancer 1 early onset"
CDS       join(65982..66061,74300..74353,83548..83625,85125..85213,
          85820..85959,90198..90303,92789..92834,94157..94233,
          95219..98644,99047..99135,107504..107675,113466..113592,
          115559..115749,118842..119152,122387..122474,
          126131..126208,126709..126749,132947..133030,
          138965..139019,140888..140961,142379..142439,
          144281..144405)
          /gene="BRCA1"
          /codon_start=1
          /product="breast cancer 1 early onset"
          /protein_id="ABA29220.1"
          /db_xref="GI:75874871"
          /translation="MDLSALRVEEVQNVINAMQKILECPICLELIKEPVSTKCDHIFC
          KFCMLKLLNQKKGPSQCPLCKNDITKRSLQESTRFSQLVEELLKIICAFQLDTGLEYA
          NSYNFAKKENNSPEHLKDEVSIIQSMGYRNRAKRLLQSEPENPSLQETSLSVQLSNLG
          (SEQ. ID NO. 17)

MOST OF THE AMINO ACID SEQUENCE FROM THIS BRCA1 GENE WAS DELETED FROM THIS
SECTION FOR SIMPLICITY
          LPRQDLEGTPYLESGISLFSDDPESDPSEDRAPESARVGNIPSSTSALKVPQLKVAES
AQSPAAAHTTDTAGYNAMEESVSREKPELTASTERVNKRMSMVVSGLTPEEFMLVYKF
ARKHHITLTNLITEETTHVVMKTDAEFVCERTLKYFLGIAGGKWVVSYFWVTQSIKER
KMLNEHDFEVRGDVVNGRNHQGPKRARESQDRKIFRGLEICCYGPFTNMPTDQLEWMV
QLCGASVVKELSSFTLGTGVHPIVVVQPDAWTEDNGFHAIGQMCEAPVVTREWVLDSV
ALYQCQELDTYLIPQIPHSHY"
(SEQ. ID NO. 18)

ORIGIN 1 gatctaattt tgtccgttca ggggaacata attttgcctg gctttgctaa tccaaatgca
       61 catttgaaca caacaatctg aatagttaca acatacaaag catgtgggtg aagagtagct
          (SEQ. ID NO. 19)

THE NUCLEOTIDE BASE SEQUENCE BETWEEN POSITION 120 AND POSITION 150420 FOR THIS
ENTRY WAS DELETED FOR SIMPLICITY-
150421 tacatatctc tgaccctttg tccccatcca atctccccag accttccatc ccaagcccaa
150481 acacaacctt acctgctgct cctttcagg caccctggcc accaaatata ggaacccata
150541 aattttgctc atactctatg ttctactagg caagtcctga tc
```

The input file associated with the above exemplary sequence entry would provide information relating to, for example:

Origin of DNA sequence entry—organism; *homo sapiens* (human)
Size of fragment—150582 base pairs
Accession number is a unique identifier of this specific sequence within the data containers of NCBI, EMBL and DDBJ
Authors, submission date, source etc
Chromosome 17
Sequence from genomic DNA
Three gene products associated with the sequence entry
  NBR1 (mck43_A)—259 ... 14273
  LOC10230 (NBR2)—50107 ... 51338
  BRCA1—65982 ... 144405

As is described further below, databases containing DNA sequence data may be accessed and the sequence entries of such databases fragmented and packetized using BioIntelligent™ biologically-relevant headers containing other information included within such databases. In particular, DNA sequence entries and the annotations from the above databases may be mapped and normalized consistent with a biological data model, thereby providing users the capability to access sequence data from normalized versions of inconsistently-formatted databases.

In one embodiment data obtained using the UCSC Genome Browser provides an additional source of sequenced data used for construction of packetized DNA sequence data. In the present example of Appendix I, sequence positions from the entry shown can be mapped to chromosome 17 on the UCSC Genome Browser, and additional mapped positions on intron/exon positions, methylation sites and SNPs can be mapped for these genes. Information concerning the start and end positions of exons can also be extracted from the mRNA and coding sequence (CDS) set forth in Appendix I. A biological data unit within the output file would then contain a bit-encoded sequence payload ecapsulated with mapped header information obtained from annotation data within the relevant database. In one implementation the sequence data associated with a data unit payload might also comprise a portion of a table, tag or pointer system used in relation to a second sequence database. Appendix I provides additional information concerning features of the genes and gene products identified therein.

It should be understood that representations of biological sequences using other than a 2-bit format is also within the scope of the present disclosure. For example, in other cases 3 or 4 bits may be necessary to represent the different base cases. For example, there will be cases where a position in a DNA sequence can be represented by either purine (a G or an A represented by R) but not by neither pyrimidine (a C or a T represented by Y). In another case, it may be necessary or desirable to represent modified or substituted purines and tautomers using a 16, 32 or 64 bits to represent each possible base case. Furthermore, an 8-bit scheme would generally be sufficient for representing base methylation at CpG islands that are associated with regulation and transcriptional control of the relative genes, and in such cases a higher-bit representation could be required.

Figure 18B:
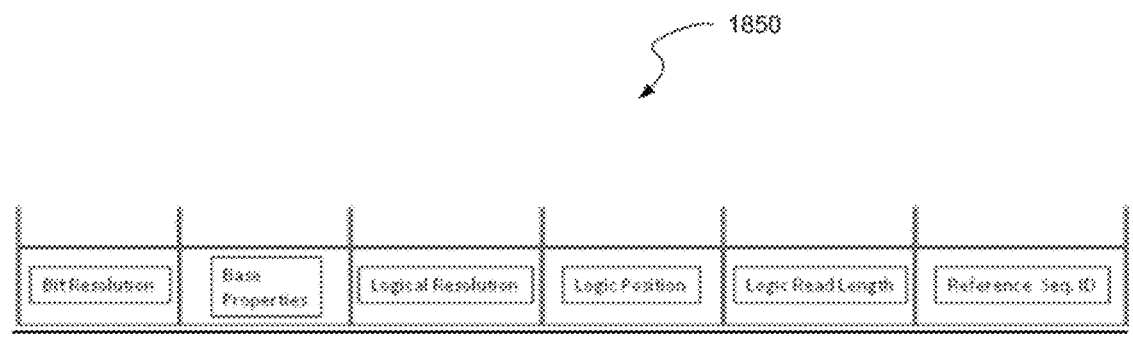
FIG. 18B depicts a BioIntelligent™ biologically-relevant header schema including a plurality of fields containing information defining aspects of the representation of biological sequence data within an associated payload.

Attention is now directed to FIG. 18B, which depicts a BioIntelligent™ biologically-relevant header schema 1850 which includes a plurality of fields containing information defining aspects of the representation of biological sequence data within an associated payload. The header schema 1850 may form a part of the BioIntelligent™ biologically-relevant header of a biological data unit, and enables a multi-bit representation of biological sequence data to be included within the payload of such a data unit. For example, a Bit Resolution field of the header schema 1850 may include information indicative of the number of bits (i.e., 2, 3, 4 or 8) used within the associated payload to represent each nucleotide base or other element within the biological sequence of interest. A description of the definitional information included within each of the fields of the header schema 1850 is set forth below.

| 0-1 Bit Resolution | |
|---|---|
| 00 | 2 bit representation |
| 01 | 3 bit resolution |
| 10 | 4 bit resolution |
| 11 | 8 bit resolution |

| 2-5 Base Properties | |
|---|---|
| 0000 | Primary bases (unmodified) |
| 0001 | Methylated C (5hmC; 5-hydroxymethyl Cystine; C''') |
| 0010 | Methylated C (5mC; 5 methyl Cystine; C') |
| 0010 | Hypoxanthine (modified A; A') |
| 0100 | Xanthine (modified G; G') |
| 0101 | Modified C in CpG islands (C') |
| 0110 | Modified C in CpG islands (C'') |
| 0111 | Modified bases in coding regions |
| 1000 | Ribose (sugar) modification |

| 2-5 Base Properties | |
|---|---|
| 1001 | |
| 1010 | |
| 1011 | |

| 6-9 Logical Resolution | |
|---|---|
| 0000 | A (adenine) |
| 0001 | C (cytosine) |
| 0010 | G (guanine) |
| 0011 | T (thymine) |
| 0100 | M (amino; A or C) |
| 0101 | R (purine; A or G) |
| 0110 | W (A or T) |
| 0111 | S (C or G) |
| 1000 | Y (pyrimidine; C or t) |
| 1001 | K (keto; G or T) |
| 1010 | V (not T; A or C or G) |
| 1011 | H (not G; A or T or C) |
| 1100 | D (not C; G or A or T) |
| 1101 | B (not A; G or T or C) |
| 1110 | N (G or A or T or C) |
| 1111 | (reserved) |

| 10-11 Logic Position | |
|---|---|
| 00 | Absolute; from chromosome start |
| 01 | Relative; from first regulatory base |
| 10 | Relative; transcription start position |
| 11 | Relative; A in start codon (translation start; AUG) |

| 12-13 Logic Read Length | |
|---|---|
| 00 | Number of bases |
| 01 | Number of codons |
| 10 | Element/feature size |
| 11 | User defined |

| 14-15 Reference Sequence ID | |
|---|---|
| 00 | Reference #1 |
| 01 | Reference #2 |
| 10 | Reference #3 |
| 11 | Reference N |

Assumptions:
1. Only 4-bit resolution is employed
2. Additional base properties may be discovered
3. Only 16 logical resolutions
4. Limited number of reference sequences (used to define an instruction-based representation of the payload)

Multi-Layered, Multi-Dimensional Biological Data Model

Referring again to FIG. 16, representation of biological sequence data such as, for example, the DNA sequence data depicted in FIG. 18, using biological data units having header information corresponding to the layers of the biological data model 1600 is expected to facilitate efficient processing of such sequence data. For example, in cases in which it is desired to query a data container containing a large number of biological data units, the multi-layered representation of FIG. 16 enables queries to be structured to be processed using only the information within the headers of the biological data units and without directly examining the sequence data within the payload of such data units. As a consequence, data from different databases can be processed in real time, and access to various types of data allows for more sophisticated analysis of biological, medical, clinical and other related datasets. This is believed to represent a significant advance relative to conventional database-centric processing techniques, which typically rely upon evaluation of the entirety of the sequence information stored within a database. It should be appreciated that the multi-layered, multi-dimensional data architecture represented by FIG. 16 provides but one example of the many different architectures capable of being implemented using biological data units containing BioIntelligent™ biologically-relevant headers.

As shown in FIG. 16, the biological data model 1600 includes a DNA layer 1610, an RNA layer 1620, a protein layer 1630, a biological systems layer 1640, an application layer 1650, a top-level layer 1660, a medical data layer 1670, a molecular pathways layer 1680 and a management layer 1690. In various embodiments the information associated with each of these layers may be included within the header and/or payload of biological data units structured consistent with the data model 1600.

The DNA layer 1610 will generally contain information, data and knowledge associated with DNA found in public and private databases, as well as information published or generally accepted by the scientific community to be acknowledged. For example and without limitation, the information included within the DNA layer 1610 may comprise: 1) the actual nucleotide sequence of DNA fragment, 2) chromosome position or location, 3) nucleotide start and end positions, 4) name of the gene, 5) information on promoter region, 6) open reading frame, 7) transcription start site, 8) intron and exons, 9) known mutations, 10) types of mutations, 11) any phenotypic effects, 12) any metadata or annotation or knowledge or possible predictions on any sequence of DNA found in any other database.

The RNA layer 1620 is positioned adjacent the DNA layer 1610. The information included within this pair of layers is highly interrelated. The RNA layer 1620 contains information that is related to or pertaining to RNA sequence, function and structure. In certain embodiments this layer may contain information relating to various types of RNA including, for example, mRNA, tRNA, rRNA, miRNA, siRNA, and other non-coding RNAs. The layer 1620 may also include information concerning snRNA involved with splicing and guiding RNA in telomerase. Examples of specific information which may be included within the RNA layer 1620 include, without limitation: 1) the sequence of the pre-mRNA and mature mRNA sequence, 2) information on ribosome binding site, 3) initiation site of protein synthesis or translation start codon, 4) processing of mRNA, 5) splice junctions, 6) alternative splicing data, 7) polyA tail data, 8) microRNA data, 9) expression data from microarray, 10) and essentially any other data concerning RNA contained within any other database.

In the exemplary representation of FIG. 16, the protein layer 1630 resides directly on top of the RNA layer 1620. In this configuration, BioIntelligent™ biologically-relevant information flows up from the RNA layer 1620 to the protein layer 1630 and can interrelate with information from the DNA layer 1610 through the RNA layer 1620. This means, for example, that data from the protein layer 1630 can be processed along with DNA data. The following types of information may, for example and without limitation, be included within this layer: 1) amino acid sequence of a protein, 2) any post-translational modifications of a protein, 3) any data on activity of a protein or related polypeptides, 4) crystal structure data, 5) NMR data, 6) mass spectrometry data, 7) any protein-protein interaction, 8) any protein-nucleic acid interactions, 9) any pathway involvement data, 10) other data concerning any protein, polypeptide or nascent peptide published or present within any other database.

The biological systems layer 1640 may include information relating to, for example and without limitation, transcriptomics, genomics, epigenomics, proteomics, metabolomics and other biological-system-related data. As the field of bioinformatics advances further, this layer may be scaled to accommodate other systems-level information, e.g., interactomics, immunomics, chromosomomics, and the like. This layer biological systems layer 1640 is preferably situated between the protein layer 1630 and the application layer 1650.

The application layer 1650 serves to facilitate user-definable interaction with the normalized data included within lower layers of the data model 1600. BioIntelligent™ biologically-relevant in the application layer 1650 may use application-specific header filtering to deliver query, analysis and processing results in real time.

The top-level layer 1660 uses data from microarray gene expression analysis, mass spectrometry data on proteomics, copy-number variation data, single nucleotide polymorphisms and/or other data related to disease conditions, phenotypic expression, behavior, pharmacogenetics, epigenetic markers to run applications relating to processing, transport, analysis, compression, retrieval, storage and any other such operation capable of being applied to biological sequence data. In the embodiment of FIG. 16, the layer 1660 resides on top of the cubical data model 1600 along with the application layer 1650, and is adjacent the medical data layer 1670.

The medical data layer 1670 may contain, without limitation, clinical data, personal health history and record data, medication data, lab test result data, image data (mammograms, x-ray, MRI, CAT scan, ultrasound, etc.), any other relevant, related, co-related or associated data.

The molecular pathways layer 1680 will generally include BioIntelligent™ biologically-relevant information concerning pathways and systems. This layer may contain information on differential expression of genes at the level of organs, systems and pathways as related to pertinent data found in related layers. The BioIntelligent™ biologically-relevant information within the layer 1680 may focus upon, for example and without limitation, protein-protein interactions, protein-nucleic acid interactions, as we as protein-metabolite interactions. This type of data may aid in elucidating key biological pathways, and thus indentify important drug targets. The information at this layer may also include, for example, sequence data and annotations in databases such as Reactome, IntAct and Rhea at EBI.

The management layer 1690 sits atop the z-dimension of layers within the data model 1600 and controls and manages the flow of data across its cubical structure.

Representation of Multi-Layered, Multi-Dimensional Biological Data Model Using BioIntelligent™ Biologically-Relevant Headers Attention is now directed to FIG. 19, which depicts a flow 1900 of inheritable genetic information from the level of DNA to RNA to protein. The information available in each of these levels constitutes biologically relevant data of the type which may be included within BioIntelligent™ biologically-relevant headers corresponding to layers of the data model 1600. As is discussed below, FIG. 19A illustrates the interrelationships between and among the biological information represented by biological data units associated with several layers of the data model 1600. FIG. 19B illustrates an exemplary protein protocol data unit (PPDU) including an amino acid payload and a header containing various types of information relevant to the payload. Finally, FIG. 19C provides a graphical representation of the types of dynamic interactions possible between BioIntelligent™ biologically-relevant headers within a layer of the data model 1600, as well as between two or more layers of the model 1600.

Figure 19A:
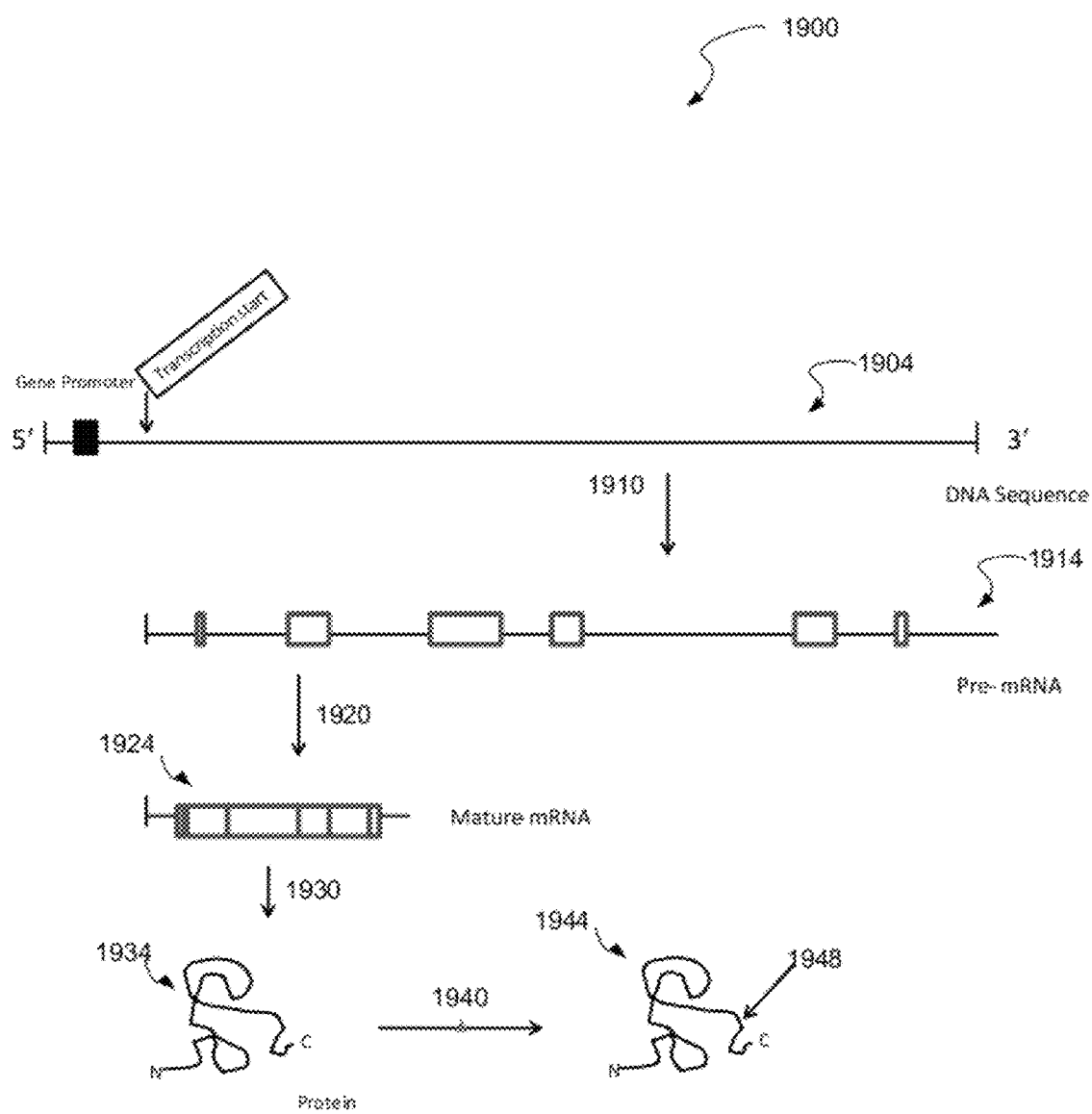
FIG. 19 depicts a flow of inheritable genetic information from the level of DNA to RNA, and RNA to protein. SEQ ID NO.: 28), (SEQ ID NO.: 29), (SEQ ID NO.: 30), (SEQ ID NO.: 31).

Turning to FIG. 19A, there is shown a representation of DNA information 1904 associated with a segment of a DNA sequence. For example, the sequence information 1904 will be in the 5' to 3' position indicated. The segment of DNA could be of variable length. The thick black bar within the DNA information 1904 represents a promoter region which is meant or referred to in this case in general as the regulatory region of the gene of interest. In such case this region could include transcription factor binding sites and other promoter sequence elements. This is the type of information included within at least a DNA-layer BioIntelligent™ biologically-relevant header of a biological data unit containing DNA sequence data within its payload. In addition, there may be information available on other cis or trans acting regulatory elements that are associated with the gene. For example, enhancer elements that can have profound effects on expression of this gene, which in some cases could be located at a considerable distance from the gene.

Referring to FIG. 19A, the process 1910 comprises the conversion of a DNA sequence into RNA, i.e., transcription. Pursuant to this process a gene included within the DNA sequence may code for a protein or for an RNA gene product. In some cases, transcription starts at a specific site located in a certain range of bases (generally between 10 and 50) downstream of the promoter. As shown, pre-mRNA 1914 (precursor messenger RNA) comprises the sequence of the RNA as it is transcribed. In the example of FIG. 19A, the pre-mRNA 1914 includes 6 exons and 5 introns. The transcription process results in an RNA molecule that starts at the start site indicated in the DNA layer. Depending on the cell or tissue type, the pre-mRNA 1914 is alternatively spliced in process 1920 to generate mature mRNA 1924. Process 1920 is generally referred to as RNA processing, and involves activity by the spliceosome. At this stage, before splicing of the introns occurs the position of the bases in the pre-mRNA 1914 will correlate in a positional manner to the base positions in the DNA information 1904 relative to the start of transcription. Here, mapping of the positions and coordination between the DNA and RNA layers could be straightforwardly achieved using the BioIntelligent™ biologically-relevant header structure disclosed herein.

Following the processing of pre-messenger RNA 1914, the mature transcript 1924 with a capped 5' end and poly adenylated tail is added to the tissue-specific spliced ordered exons. Typically, the mature mRNA 1924 is significantly shorter than the pre-mRNA 1914. Accordingly, the relative positional mapping of sites or sequence elements between the mature mRNA 1924 and the DNA sequence information 1904 is not proportionate. For example, after splicing, sequences that were separated by a significant number of bases are now juxtaposition to each other. The processing of the pre-mRNA 1914 changes the positional relatedness in the RNA with respect to the DNA base sequence. However, the spice junctions and other features of the mature transcript 1924 can be located or mapped back to positions in the DNA information 1904 using a series of pointers from the BI headers in both layers.

In a translation process 1930, the mature mRNA 1924 is used as a template by a ribosome in connection with creation of a protein 1934 comprised of a sequence of amino acids. Using three bases at a time (codon) and in a specific frame, the ribosome uses a transfer RNA (tRNA) with specific amino acid attached at one end and an anti-codon that is complementary to the condon in mRNA to incorporate the correct amino acid in the growing polypeptide chain. Since only mature mRNA with a special 5' cap structure, spliced exons, and polyA tail provide templates for translation, only exons (by definition and not introns) are expressed as proteins. However, in different tissue types what is considered an intronic sequence can be alternatively spliced and be a part of an exon coding region in the mature mRNA. This information may be captured within a BioIntelligent™ biologically-relevant header.

In a post-translational modification process 1940 various groups are used to mark the protein 1934, thereby resulting in a mature functional protein 1944. This modification process 1940 can be important for enzyme activation, protein trafficking and other biological functions of the protein. At this stage, the polypeptides can be modified using groups such as, but not limited to, phosphate, acetate, lipids, sugars and other such modifications. In addition, disulfide bridges can be formed, peptides can be cleaved by proteolysis and/or residues removed from the ends to produce the mature functional protein 1944. Protein modification data can be derived from, for example, mass spectrometry or Eastern blotting data.

In the representation of protein 1934 and mature functional protein 1944, the "N" and the "C" refer to the amino and carboxyl termini, respectively. For example, the N terminus is the end of the protein from which translation progresses, and corresponds to the 5' end of the mRNA. Conversely, the C terminus corresponds to the 3' end of the mRNA. Each amino acid in the peptide represents 3 bases in the mature mRNA. In the specific embodiment of FIG. 19A, the location 1948 represents a specific position on the protein where a certain modification is normally made. If, for example, a base substitution at the DNA level caused an amino acid substitution at position 1948 and this substitution affects a modification for enzymatic activity of the protein, an undesired phenotypic expression might result. To better understand the nature of an aberrant protein modification, a researcher may choose to study the corresponding DNA mutation. The present system advantageously enables the position associated with the modification to be mapped back to the DNA layer by including information relating to the modification within BioIntelligent™ biologically-relevant header of the protein protocol data unit (PPDU) for the protein.

The usefulness of the establishment of relationships within and between the biological data units exemplified by FIG. 19A may be further appreciated by considering a scenario in which a protein enzyme is used in an assay to determine whether or not it is active, thereby indicating the presence or absence of a disease condition. For example, consider a biological data unit in which an amino acid sequence (i.e., a protein protocol data unit, or "PPDU") comprises the payload and the specific modification of the particular amino acid residue that is associated with the disease is known. In this case for example the data from mass spectrometry and Eastern blotting is used to determine modification site. This information may be included within the protein layer header of the biological data and advantageously can be related and mapped back to the DNA genomic sequence data layer through headers associated with other layers. For example, phosphorylation is the addition of a PO₄ to an amino acid side chain, generally on serine, threonine and tyrosine residues. In this example, the modification is a phosphorylation of a serine residue, which is one of several potential modifications. This certain modification (phosphorylation) described in the exemplary scenario may be of particular significance. That is to say that a mutation of the DNA that causes a substitution of this specific serine in the protein in this example would confer a certain disease condition. For example, a clinical assay of this enzyme activity might be useful in diagnosing a disease.

Figure 19B:
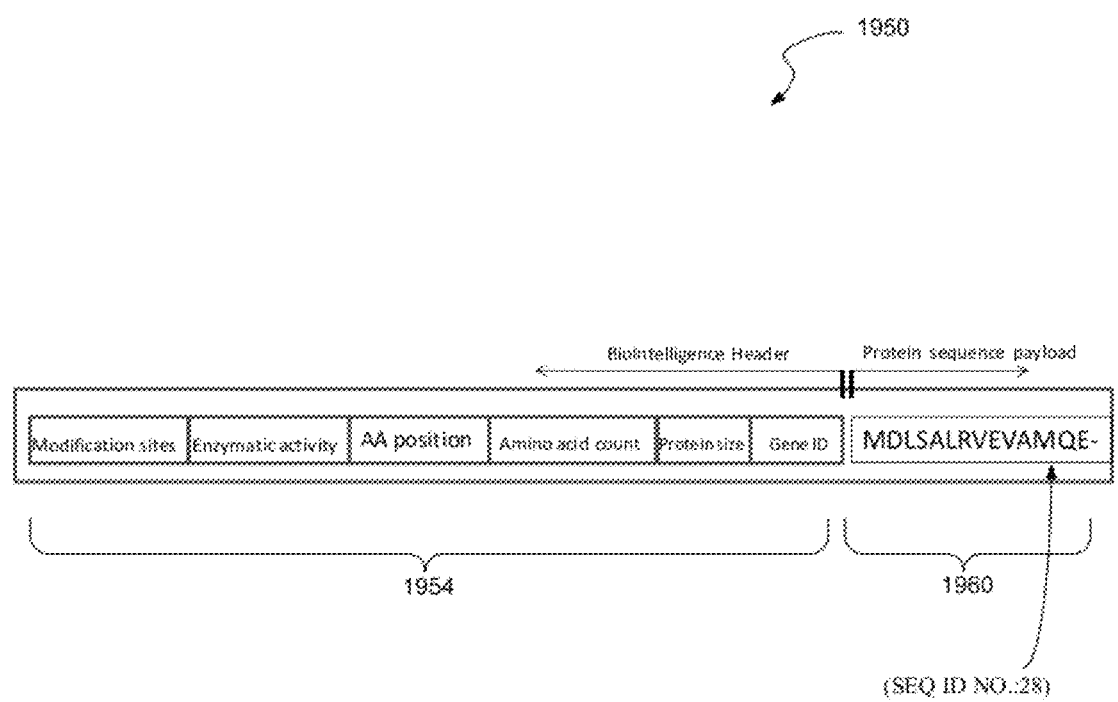

Attention is now directed to FIG. 19B, which illustrates an exemplary PPDU 1950 containing a BioIntelligent™ biologically-relevant header 1954 and an amino acid sequence payload 1960. The information contained in the BioIntelligent™ biologically-relevant header 1954 is specific to the protein corresponding to the amino acid sequence represented in the payload 1960 and is not limited to the type of information depicted in FIG. 19B. Since there exist 20 different amino acids and the side chain of each may be modified, in one embodiment a representation scheme utilizing 8 bits per amino acid is employed. Such an approach allows for representation of a minimum of 10 different modification or logical states per amino acid residue, with bits being arranged based upon the particular property of the residue being represented. Amino acids are usually classified by the properties of their side chain into four groups (i.e., acidic, basic, polar, or nonpolar). That is, the side chain of an amino acid can make it a weak acid or a weak base, and a hydrophile if the side chain is polar or a hydrophobe if it is nonpolar.

The following provides an exemplary arrangement of 8-bit representations of the 20 amino acids into a set of four groups.

| 0000 0000 | F | Phenylanaline |
| 0000 0001 | L | Leucine |
| 0000 0010 | I | Isoleucine |
| 0000 0011 | M | Methionine |
| 0000 0100 | V | Valine |
| 0000 0101 | P | Proline |
| 0000 0110 | A | Alanine |
| 0000 0111 | G | Gylcine |
| 0000 1000 | W | Tryptophan |
| 0000 1001 | S | Serine |
| 0000 1010 | T | Threonine |
| 0000 1011 | Y | Tyrosine |
| 0000 1100 | Q | Glutamine |
| 0000 1101 | N | Asparagine |
| 0000 1110 | C | Cysteine |
| 0000 1111 | H | Histidine |
| 0001 0000 | K | Lysine |
| 0001 0001 | R | Arginine |
| 0001 0010 | D | Aspartic acid |
| 0001 0011 | E | Glutamic acid |
| 0010 0000 | | |
| 0010 0001 | | |
| 0010 0010 | | |
| 0010 0011 | | |

Figure 19C:
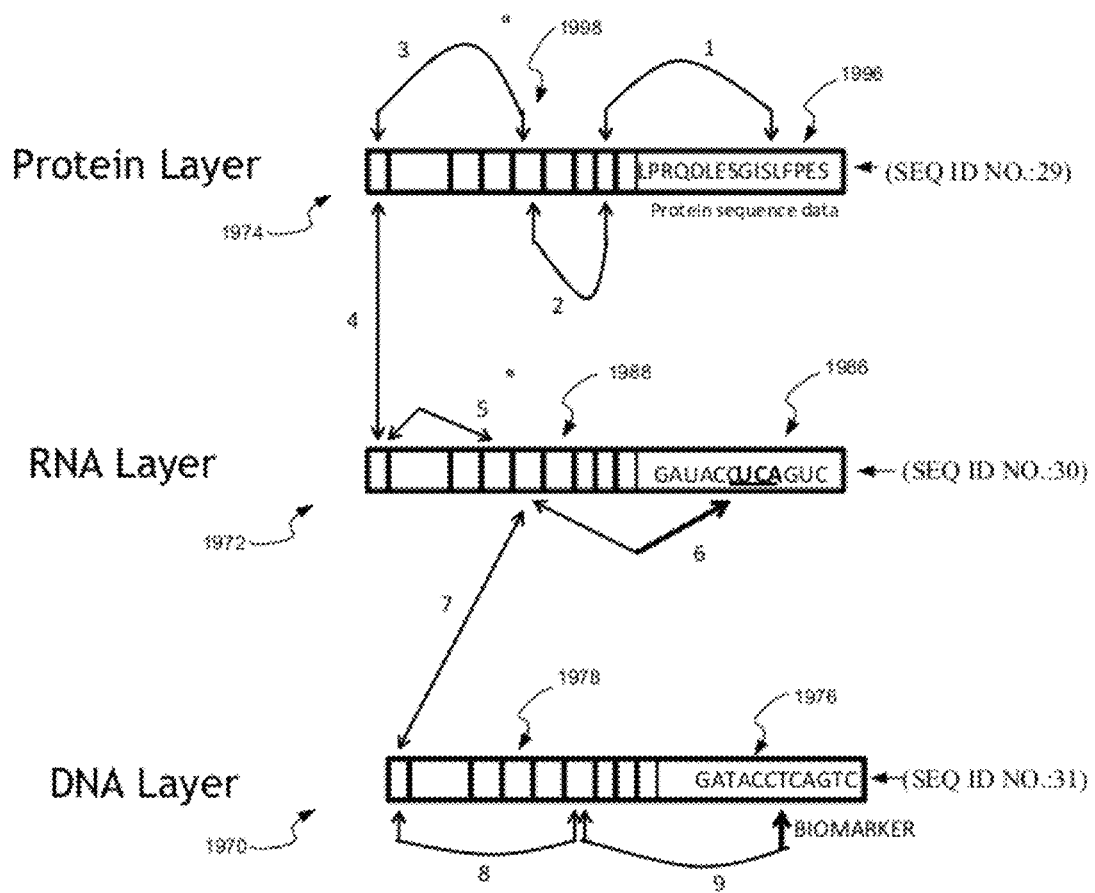
Figure 19D:
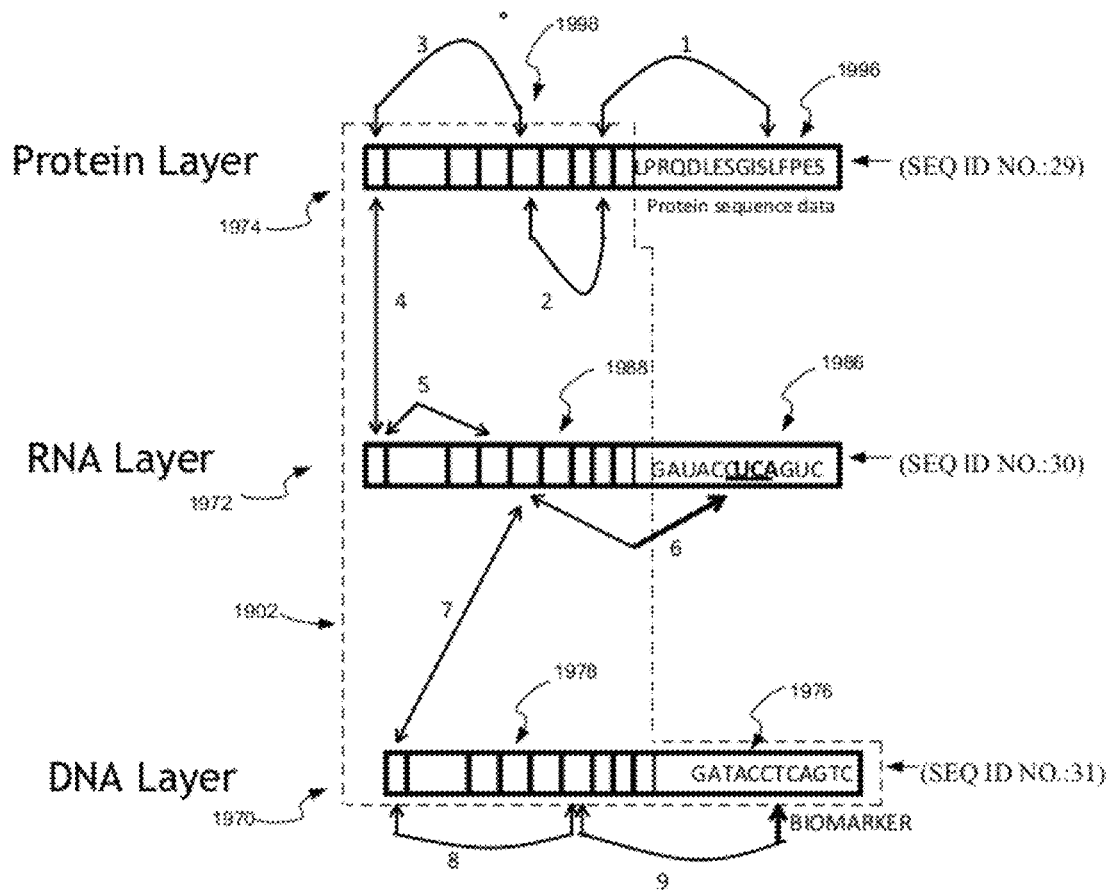

Attention is now directed to FIG. 19C, which illustratively represents relationships within and between a set of three related biological data units associated with a protein affected by a post-translational modification. As shown, FIG. 19C depicts a DNA protocol data unit (DPDU) 1970, an RNA protocol data unit (RPDU) 1972, and a protein protocol data unit (PPDU) 1974. In particular, FIG. 19C illustrates various relationships between the headers and payloads within each of the PPDU 1974, RPDU 1972, and DPDU 1970, as well between the header and payloads of different ones of the PPDU 1974, RPDU 1972, and DPDU 1970.

Relationship 1:
As shown in FIG. 19C, information within a first position of the header of the PPDU 1974 relates to the specific amino acid in the protein affected by the post-translational modification. See reference numeral 1.

Relationship 2:
BioIntelligent™ biologically-relevant information that relates to the modification is associated with the location of the specific amino acid in the protein. See reference numeral 2.

Relationship 3:
Such information is defined by the logical position of the amino acid. In the example of FIG. 19C, the specific modification is phosphorylation and relates to a second position in the header of the PPDU 1974, which points to a header of the RPDU 1972. See reference numeral 3.

Relationship 4:
Certain information contained in the header of the PPDU 1974 is defined by querying the header of the RPDU 1972, which allows data from the protein and RNA layers to interrelate. See reference numeral 4.

Relationship 5:
The header of the RPDU 1972 also illustrates a dynamic definition and BioIntelligent™ biologically-relevant relationship. For example, the header of the RPDU 1972 may contain information on splice site junctions, reading frame and other relevant data from pre-mRNA processing. See reference numeral 5.

Relationship 6:
This shows the specific codon within the payload of the RPDU 1972 for the serine amino acid that is phosphorylated to activate the protein. See reference numeral 6.

Relationship 7:
As shown, information in the header of the RPDU 1972 that is associated with the specific codon reference above also relates to first information in the header of the DPDU 1970. Since introns are processed out of the pre-mRNA, they will relate to the coding regions of the applicable gene in the DNA layer. See reference numeral 7.

Relationship 8:
The first information within the header of the DPDU 1970 may directly relate to other information within the header defining various characteristics or features of the gene represented by the DNA sequence information within the payload of the DPDU 1970. These features or sequence elements associated with the gene may be located in or near the DNA sequence contained in the payload. For example, being a part of a regulatory element such as transcription factor binding site or CpG island. See reference numeral 8.

Relationship 9:
The other information within the header of the DPDU 1970 is shown to be associated with the specific single nucleotide polymorphism (SNP) that may be used to clinically define the diagnosis or pre-diagnosis of the disease condition being investigated in the present example. This SNP may then be defined as a "biomarker" of the disease condition. See reference numeral 9.

FIGS. 19D through 19G show how various different groups of headers from the PPDU 1974, RPDU 1972, and DPDU 1970 may each be associated with ones of the payloads of the PPDU 1974, RPDU 1972, and DPDU 1970 to define other biological data units. For example, in FIG. 19D a biological data unit 1902 comprised of the DNA sequence payload 1978, DNA header 1978, RNA header 1988 and protein header 1998 may be defined. The biological data unit 1902 may be described as an encapsulated biological data unit in the sense that the RNA header 1988 encapsulates the DNA header 1978, and is itself encapsulated by the protein header 1998.

Figure 19E:
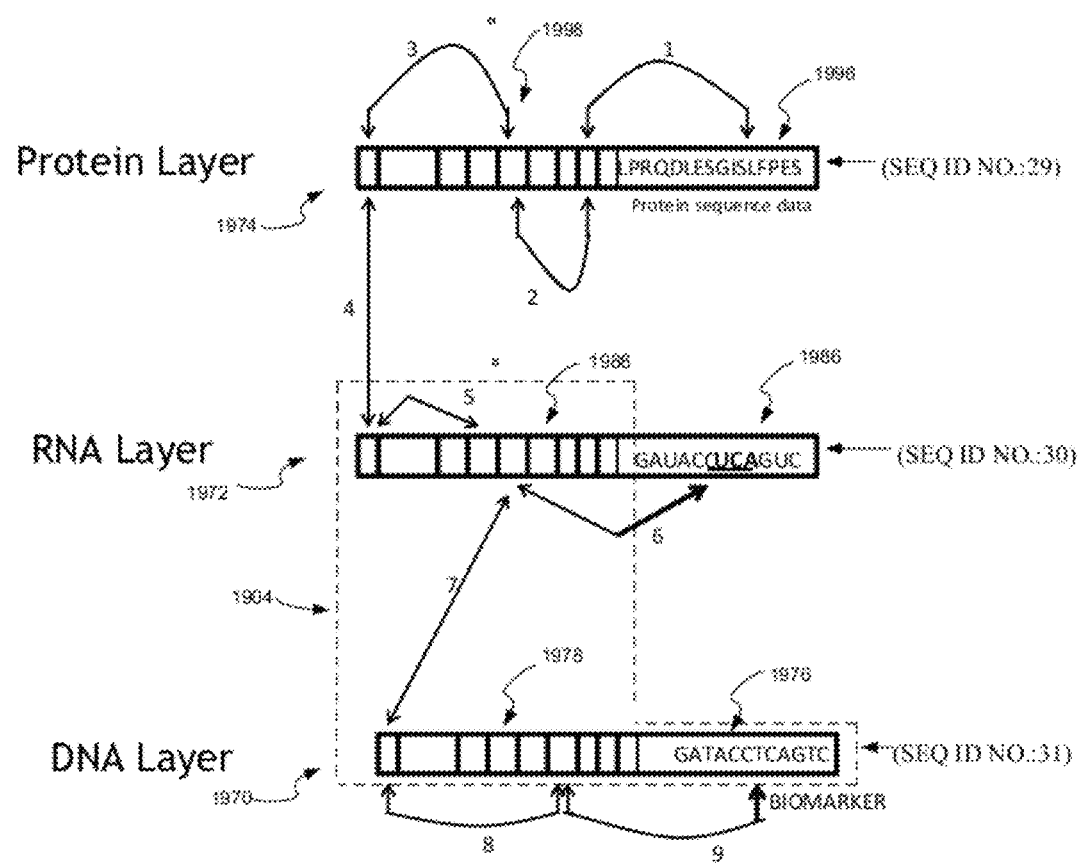
Figure 19F:
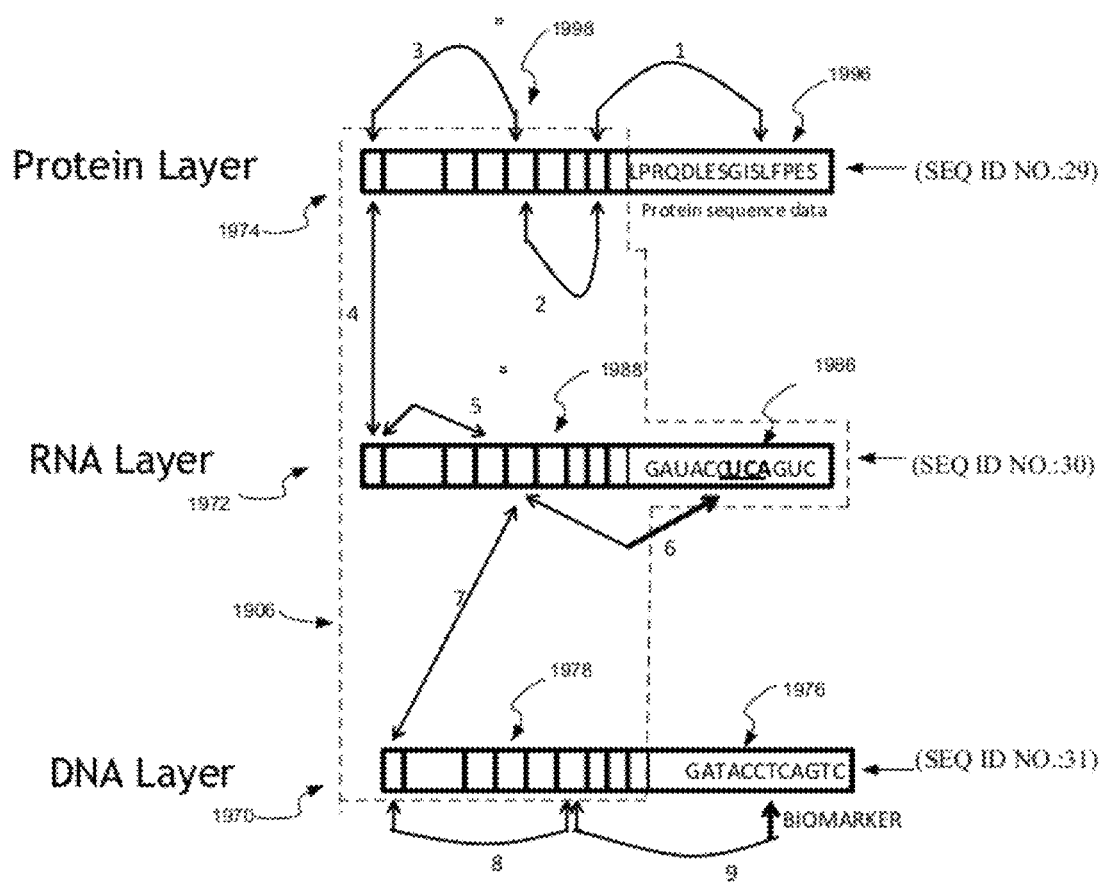
Figure 19G:
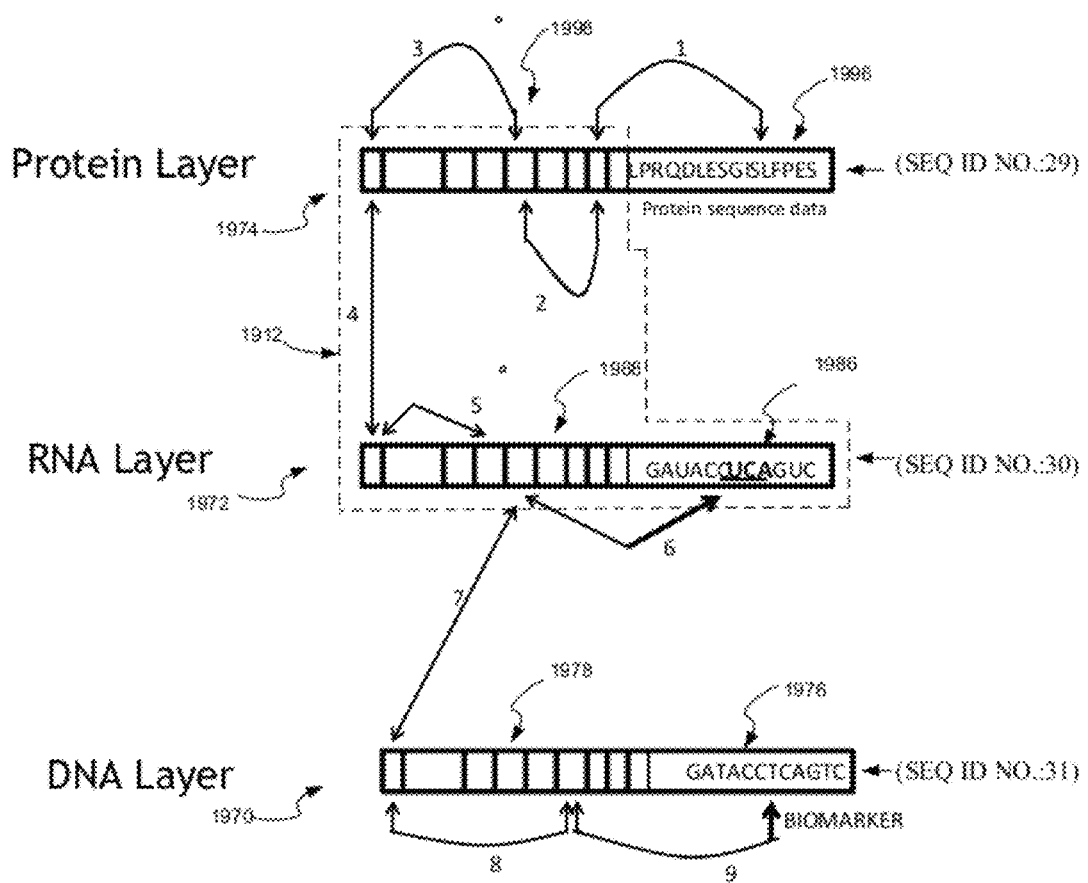

Turning now to FIG. 19E, there is shown an encapsulated biological data unit 1904 comprised of the DNA payload 1978, DNA header 1978 and RNA header 1988. Another example of an encapsulated biological data unit is provided by FIG. 19F, which depicts an encapsulated biological data unit 1906 comprised of the RNA payload 1986, DNA header 1978, RNA header 1988 and protein header 1998. Finally, FIG. 19G illustrates an encapsulated biological data unit 1912 comprised of the RNA payload 1986, RNA header 1988 and protein header 1998.

Figure 20A:
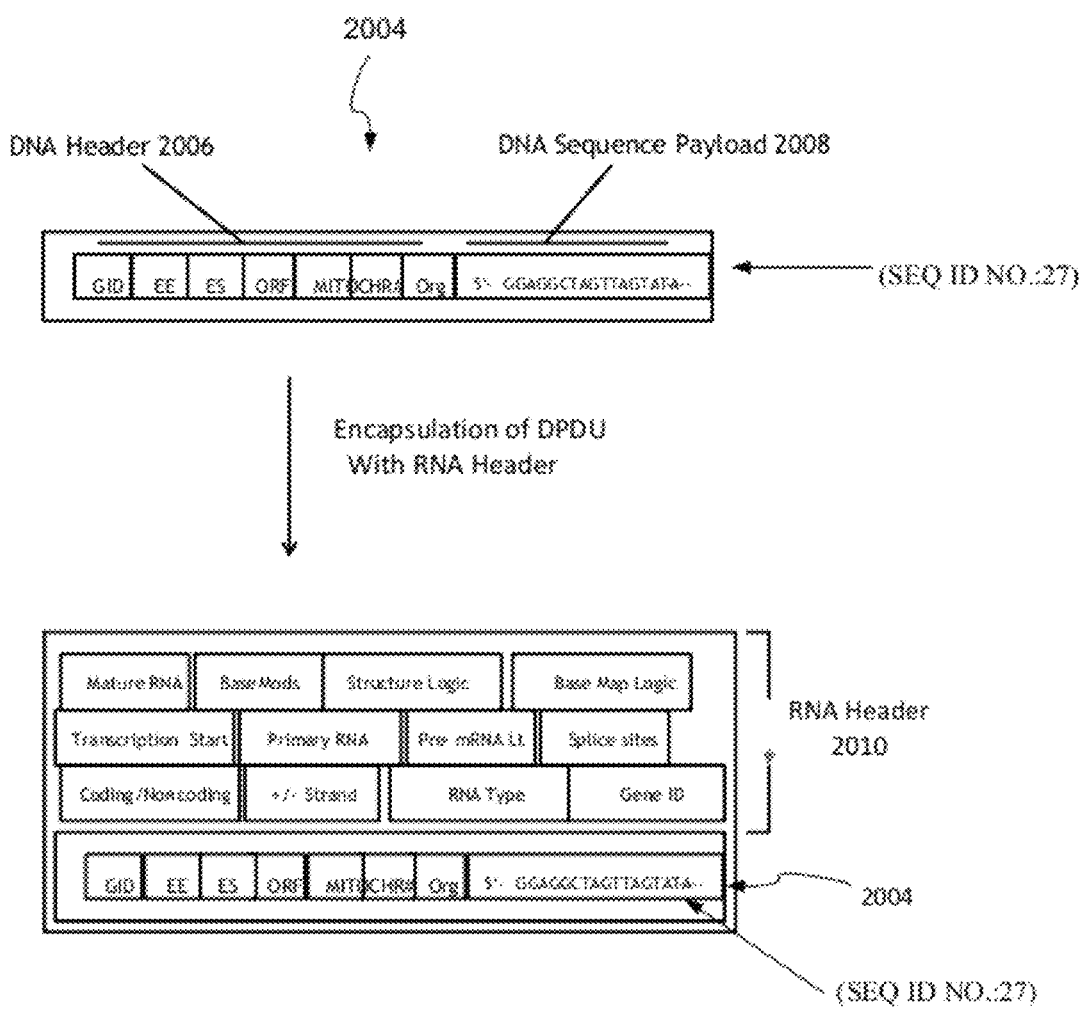
FIG. 20 illustratively represents various types of encapsulated biological data units. (SEQ ID NO.: 27), (SEQ ID NO.: 32)

Attention is now directed to FIG. 20, which illustratively represents other encapsulated biological data units. For example, FIG. 20A depicts a first encapsulated biological data unit 2002 comprised of the encapsulation of a DPDU 2004 with an RNA header 2010. As shown, the DPDU 2004 is comprised of a DNA header 2006 and a DNA sequence payload 2008. It should be appreciated that the type of information represented within the DNA header 2006 and the RNA header 2010 is exemplary and in other embodiments may comprise information of different types. In addition, the selection of the types of information contained within the headers associated with different layers of the data model 1900 influences the extent of interoperability between such different layers (via the headers associated with each layer). Note, for example, that the information included within the encapsulated DNA header 2006 of FIG. 20A differs from the information included within the DNA header 1510 of FIG. 15.

In the embodiment of FIG. 20A, the various types of information contained within the exemplary DNA header 2006 includes the following:

Org—The organism of origin of the DNA sequence in the payload
   CHR#—Chromosome number
   MITO—Mitochondrial DNA sequence
   ORF—Open reading frame
   ES—Exon start position
   EE—Exon end position
   GID—Gene name(s) in publications The various types of information contained within the exemplary RNA header 2010 include the following:
   Coding/non-coding—Refers to whether the transcript of the DNA sequence is coding or non-coding RNA
   +/−Strand—Indicates whether the gene is transcribed from the + or − strand of the DNA
   RNA Type—Indicates a type of RNA; mRNA, tRNA, rRNA, snRNA (involved in splicing and telomerase activity), microRNA (involved in post transcriptional gene regulation.
   Gene ID—Name of gene that gives rise to the RNA transcript
   Transcription start—The position of the first base transcribed
   Primary RNA—Initial transcription product of non-coding RNA
   Pre-mRNA Lt—The length of the initial transcription product of RNA coding for protein
   Splice sites—Base position of splice junctions
   Mature RNA—Final transcription product of coding and non-coding RNAs
   Base mods—Modified based in the mature RNA including base analogs
   Structure Logic—Information on the logic of the secondary structure and/or other higher-order structure interactions involving a particular base
   Base map logic—Information contained on the logical description of how the base positions in the DNA and RNA layers interrelate Within the DNA sequence payload 2008, the letters G, A, T and C represent the four nucleotide bases defining the base sequence of the segment of DNA represented within such payload 2008.

Figure 20B:
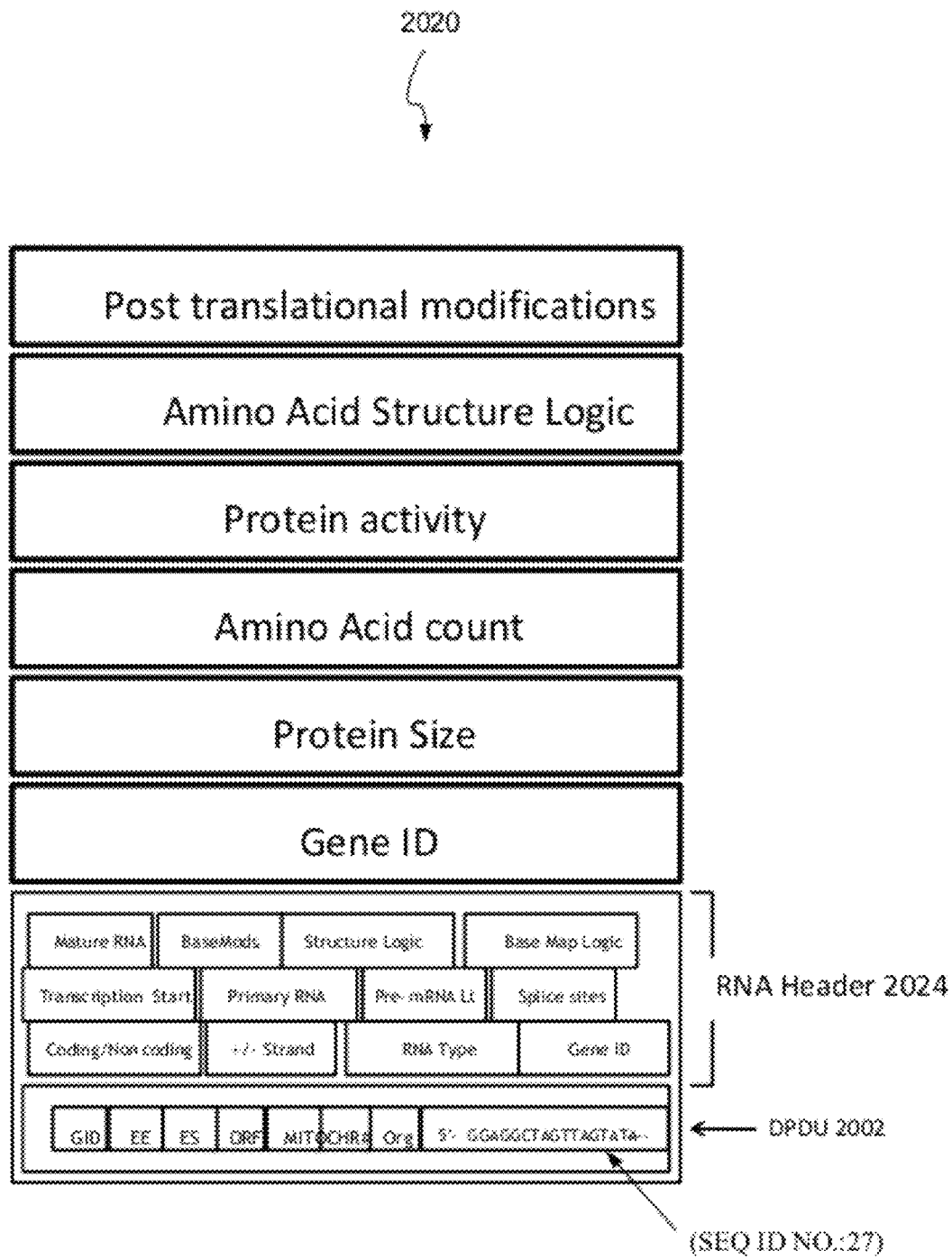

Attention is now directed to FIG. 20B, which illustrates a second encapsulated biological data unit 2020 comprised of the encapsulation of the first encapsulated biological data unit 2002 with a protein header 2024.
   Gene ID—The name or accession number as well as any other identification tag that may exist for the gene that encodes this protein. This bit of the header shares a direct relationship in each of the layers of the data model.
   Protein size—This section provides information on the protein sequence data relating to the molecular weight of the polypeptide in the data unit. For example, this may provide an identification feature in the header of the protein data packet which may interact with splice site and other processing information in RNA headers and also relate back to exon information in the DNA layer.
   Amino Acid Count—This header information gives a count of the number of amino acid residues are present in the product that is encoded by the data unit.
   Protein Activity—This would include any information on the activity of the protein product relating to the data unit data if the encoded protein is an enzymatic activity that can be assayed.
   Amino Acid Structure Logic—The amino acid structure logic of the protein header provides, based on bit assignment of each amino acid, information relating to which particular amino acid is involved in various structural elements of protein. For example, a specific amino acid or group of amino acids might be participants in a certain structural features such as, for example, an alpha helix, beta pleated sheet, flexible loop, zinc finger, helix-turn-helix, and other such protein features.
   Post Translational Modifications—The information contained here is based on type and amino acid position of modifications made to proteins following polypeptide synthesis. These modifications are a key aspect of the biological structure and function of a protein.

Figure 20C:
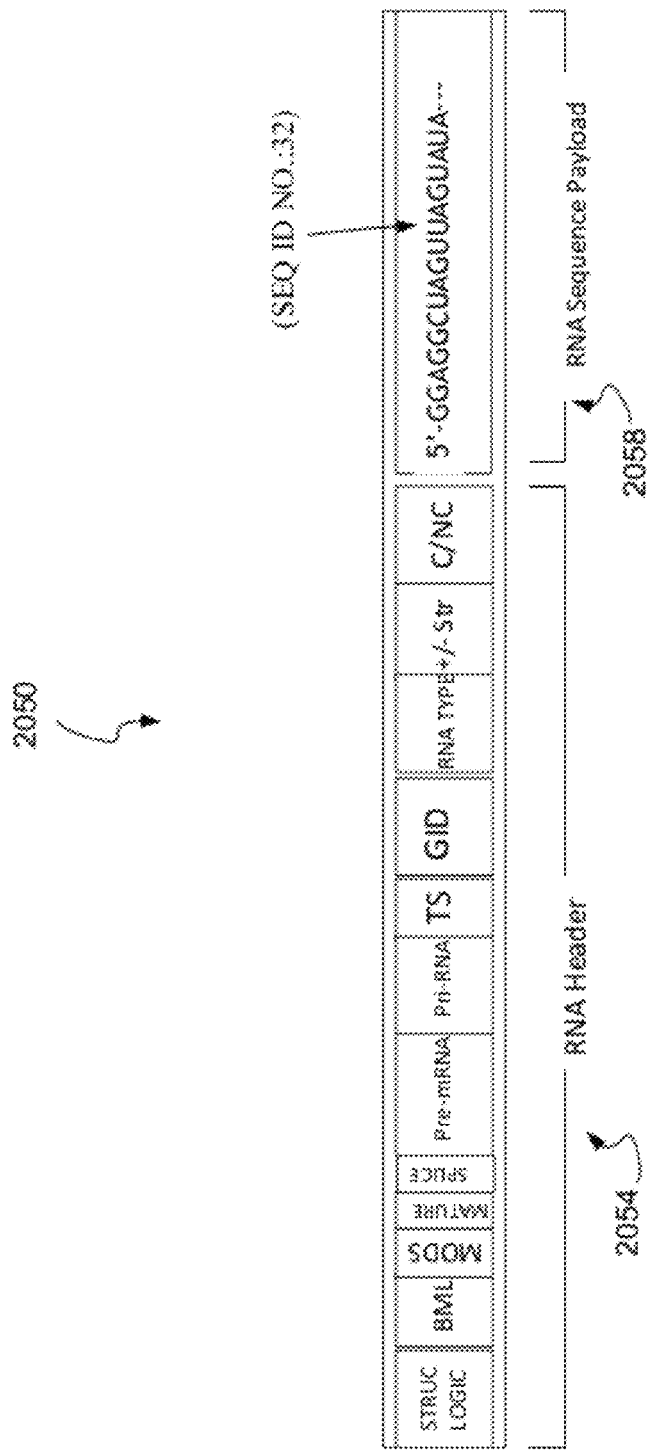

FIG. 20C illustratively represents a biological data 2050 unit predicated upon RNA sequence data. In particular, biological data unit 2050 is comprised of an RNA header 2054 and an RNA sequence data payload 2058.

High-Speed Sequence Processing, Analysis and Classification

Figure 21:
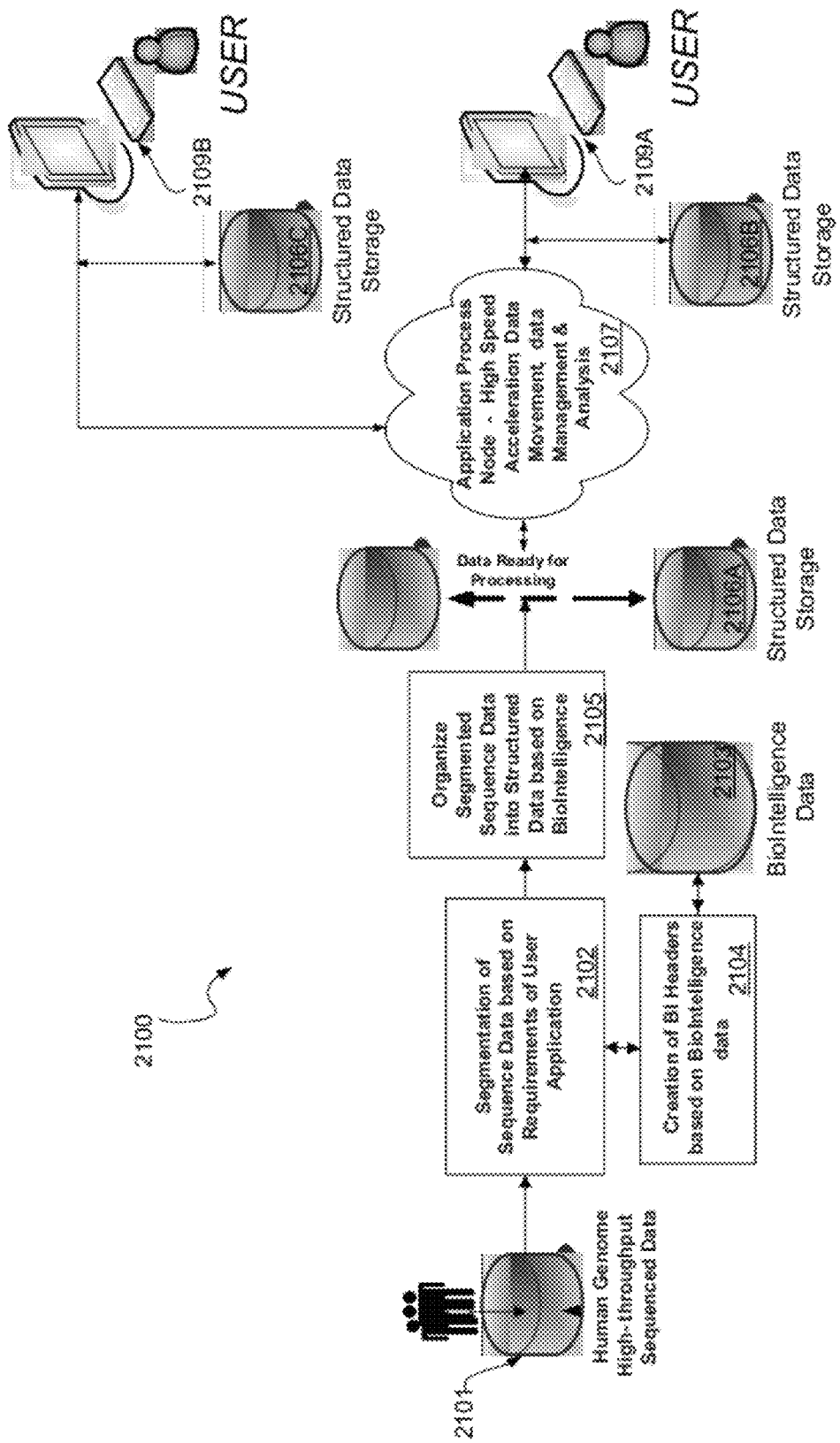
FIG. 21 provides a block diagram of a high-speed sequence data analysis system.

Attention is now directed to FIG. 21, which provides a block diagram of a high-speed sequence data analysis system 2100. The analysis system 2100 may, for example, be utilized in personalized medicine applications in which genomic-based diagnosis, treatment or other services are offered. As is discussed below, the system 2100 operates to organize and represent genomic sequence data in a structured format in association with BioIntelligent™ biologically-relevant information in the manner described above. The structured data may then be further processed and delivered to end users 2106 to facilitate analysis, research and personalized medical applications. For example, the system 2100 may be configured to establish a networked arrangement among participating medical clinics in a manner enabling the provision of genomic-based diagnosis, treatment and other services.

Turning to FIG. 21, genomic data repository 2101 is representative of genomic sequence data that has been normalized in accordance with standard protocols. Substantially all publicly available genomic sequence data which is currently available is provided by commonly-used genomics databases such as GenBank, TCGA (The Cancer Genome Atlas), EMBL-Bank, DDBJ or other databases containing biological sequence information. Other sources of information represented by genomic data repository 2101 may include, for example, various sources of microarray data, gene expression data, next-generation deep sequencing data, copy number variation data, and SNP analysis data.

In a stage 2102, the normalized data sequences from repository 2101 are segmented into multiple fragments of data sequences based upon user or application requirements. As a result, fragments or data units of DNA sequence information may be generated arbitrarily. Such fragments may include genes, introns and/or exons, regions of the genome currently referred to as "non-coding regions", or any other sequence segment relevant to a particular application. In a stage 2104, a header comprised of BioIntelligent™ biologically-relevant data provided by storage device 2103 is assigned, associated, related or embedded with each segment of DNA sequence data, thereby forming a biological data unit. This enables the selective processing and analysis of genomic information in accordance with application requirements. For example, in the case in which a system user 2106 is an oncologist, only biological data units containing information from those genes associated or otherwise correlated with a particular cancer of interest (whether human, canine or other) are selected for processing, thereby obviating the need for inefficient processing of all of the information within data repository 2101. This selective processing is facilitated by the layered architecture of the biological data model 1900 and its implementation using BioIntelligent™ biologically-relevant headers, as discussed previously. Similarly, if the user 2109 is a virologist, only biological data units having BioIntelligent™ biologically-relevant headers indicative of an association with viral genomic information, or with human genes or gene fragments relating to a specific viral infection, would be selected and processed.

The BioIntelligent™ biologically-relevant data within storage device 2103 may comprise any or all of the information and knowledge known to be of relevance to a particular gene. In addition, such data may also include information related to processing genes which have been fragmented into segments, and may be incorporated within headers designed to scale to accommodate future information not yet discovered or known about the particular gene or gene product or expression of that gene.

In stage 2104, the segmented genomic data is encapsulated, embedded or associated with appropriate BioIntelligent™ biologically-relevant headers to form biological data units. Further, certain fields of such BioIntelligent™ biologically-relevant headers may be further dynamically modified based upon application requirements. This may occur, for example, when genomic data is further segmented pursuant to stage 2102, which may essentially result in the generation of new BioIntelligent™ biologically-relevant headers for the associated gene. The segmented genomics data unit may then be further normalized (stage 2105) consistent with the layered data structure described herein in view of user application processing requirements. Storage devices 2106 are generally configured for storage of normalized segmented BioIntelligent™ biologically-relevant sequence data as biological data units in such a layered structure, thereby facilitating easy access based upon application requirements.

In response to requests from user applications, the BioIntelligent™ biologically-relevant data associated with biological data units stored within the devices 2106 may be processed, moved, analyzed or accelerated by one or more application processing nodes 2107 to provide services such as, for example, genomic-based diagnoses, visual exploitation of genomic studies, or research and drug discovery and development.

The user or client application desktop unit 2109 provides a mechanism to run user applications, which generate user request messages received by application processing nodes 2107 and display the data or results returned by such nodes 2107. The unit 2109 may be connected to localized ones of the processing nodes 2107 and storage elements 2106 through a local area network or the equivalent, and to remote processing and storage elements through a wide area network and/or the Internet.

Figure 22:
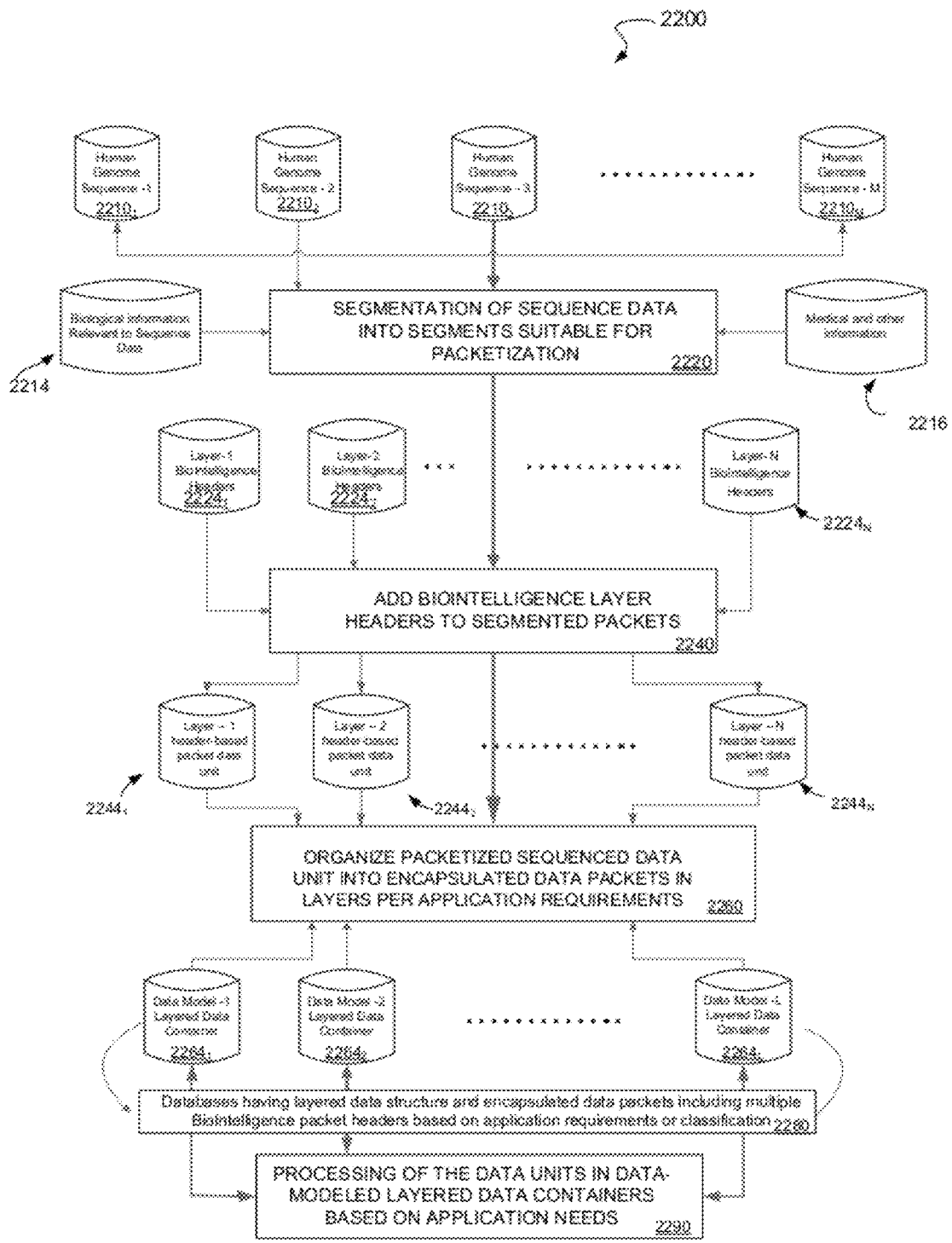
FIG. 22 provides a logical flow diagram of a process for segmentation of biological sequence data into data units encapsulated with BioIntelligent™ biologically-relevant headers.

Attention is now directed to FIG. 22, which provides a logical flow diagram of a process 2200 for segmentation of biological sequence data into data units encapsulated with BioIntelligent™ biologically-relevant headers. The process 2200 provides one example of a way in which source DNA sequence data may be fragmented to generate biological data units containing DNA sequence segments and associated BioIntelligent™ biologically-relevant header information in accordance with a layered data model such as the biological data model 1600. In one embodiment the process 2200 utilizes sequence feature information of the type annotated in well-established nucleotide databases 2210 such as, for example, NCBI, EMBL and DDBJ. By mapping the biological information within these databases into various layers of BioIntelligent™ biologically-relevant header information, a layered data model can be constructed.

Referring to FIG. 22, human genomic DNA data is shown to be accessible from different storage elements 2210. In this regard, the DNA sequence data can be stored as sequences of chromosomes or partial chromosomes or as individual genes, and may comprise all or part of a genome. In addition, the DNA sequence data could be generated from a sequencing machine and the results made accessible to a networked computer. Further, genomic sequence data might be represented in several formats including, for example, as a partial dipolar charge and phosphorescence sequence profile indicative of the sequence data.

In a stage 2220, the sequence data obtained from storage elements 2210 is mapped and aligned with the reference genomic sequence data. The DNA sequence is associated with a set of relevant molecular features using, for example, biological data 2214 deemed valid by the scientific community. This data 2214 is mapped to specific regions of a sequence entry. In addition, clinical and pharmacological data 2216 demonstrated to be associated with any coding or non-coding regions of a sequence entry is also mapped.

In one embodiment, the genomic sequence data is fragmented during stage 2220 on a per gene basis, thereby yielding a plurality of sequence entries. Gene elements contained in a sequence entry on the plus (+) strand and on the minus (−) strand are identified and marked as a unit containing the 5' upstream-CDS-3' downstream of gene. The sequence entry is segmented into data units, each of which is associated or tagged with appropriate BioIntelligent™ biologically-relevant header information in the manner discussed previously (stage 2240). The resulting biological data units 2244 comprised of, for example, segmented DNA sequence data encapsulated by one or more BioIntelligent™ biologically-relevant headers 2224 form the basis of the layered data model 1900. In one embodiment layer-1 biological data units 2244$_1$ include a payload comprised of segmented DNA sequence data and a DNA layer header. Similarly, layer-2 biological data units 2244$_2$ may include a payload comprised of segmented DNA sequence data, a DNA layer header and an RNA layer header. A layer-N biological data unit 2244$_N$ may include a payload comprised of segmented DNA sequence data, a DNA layer header, an RNA layer header, and other headers associated with higher layers of the relevant data model. Alternatively, in one embodiment layer-1 biological data units 2244$_1$ may include a payload comprised of segmented DNA sequence data and a DNA layer header, layer-2 biological data units 2244$_2$ may include a payload comprised of segmented RNA sequence data and an RNA layer header, and so on. In one embodiment a base unit may be prepended to or otherwise associated with each biological data unit in order to identify the specific headers included within the data unit and/or the number thereof.

In one embodiment BioIntelligent™ biologically-relevant headers 2224 may include physical, chemical, or biological knowledge or findings, or any related molecular data that has been peer reviewed, published and accepted as valid. BioIntelligent™ biologically-relevant headers 2224 may also include clinical, pharmacological and environmental data, as well as data from gene expression and regulation. In certain embodiments BioIntelligent™ biologically-relevant headers 2224 may further include information relating to gene and gene product interaction with other components of a pathway or related pathways. The information within BioIntelligent™ biologically-relevant headers 2224 may also be obtained form, for example, microarray studies, copy number variation data, SNP data, complete genome hybridization, PCR and other related techniques, data types and studies.

The scientific knowledge and information associated with a specific sequence and included within a BioIntelligent™ biologically-relevant header 2224 may be of several different types including, for example, molecular biological, clinical, medical and pharmacological information. In this regard such molecular and biological information could be separated and layered based on data from, for example, genomics, exomics, epigenomics, transcriptomics, proteomics, and metabolomics in order to yield BioIntelligent™ biologically-relevant data. The BioIntelligent™ biologically-relevant data may also include DNA mutation data, splicing and alternative splicing data, as well as data relating to post-transcriptional control (including microRNA and other non-coding silencing RNA and other nuclease degradation pathways). Mass spectrometric data on protein structure and function, mutant protein products with reduced or null function, as well as toxic products could also be utilized as BioIntelligent™ biologically-relevant data.

In addition, pharmacological and clinical data relating to specific gene or gene regions disposed to exert effects through interaction with gene products or other components of a pathway could be considered as a class of BioIntelligent™ biologically-relevant header information. Finally, BioIntelligent™ biologically-relevant header information could also include environmental conditions or effects correlated with certain gene or gene products believed to be related to a certain phenotypic effect or disease onset.

As mentioned above, during stage 2240 BioIntelligent™ biologically-relevant headers 2224 are associated with segmented DNA sequence data form biological data units comprised of a BioIntelligent™ biologically-relevant header 2224 encapsulating a payload containing the segmented DNA sequence data. In this process the association of a BioIntelligent™ biologically-relevant header 2224 to payload containing segmented DNA sequence data may be carried out in any of a number of ways including. For example, such association may be effected using a pointer table, tag, dictionary structure, or by embedding header information directly into the segmented sequence data.

In a stage 2260, the biological data units 2244 may be organized into encapsulated data units in accordance with the requirements of particular applications. For example, in certain cases it may be desired to create encapsulated biological data units including only a subset of the headers which would otherwise be included in the biological data units associated with a particular layer of the data model. For example, a certain application may require encapsulated biological data units having headers associated with only layers 1, 2 and 5 of a data model. Another application may require, for example, encapsulated biological data units having headers associated with only layer 2, 3 and 4 of the data model. Similarly, other applications may require that the headers of the encapsulated biological data units be arranged in a particular order, e.g., the header for layer 4, followed by the header for layer 1, followed by the header for layer 2.

In a stage 2280, the encapsulated biological data units created in stage 2280 are stored within one or more multi-layered, multi-dimensional data containers 2264. In an exemplary embodiment each data container 2264 comprises a logical structure implemented using one or multiple databases or physical memories (e.g., one database including header data and one database including sequence data).

The content of the headers of the encapsulated biological data units is chosen to promote optimal interoperability among and between layers. For example, in one simplified case each biological data unit included within the data container 2264$_1$ may include at least a DNA layer header, an RNA layer header, and a protein layer header. It is a feature of the present system that information within higher-layer headers (e.g., RNA layer headers or protein layer headers) may be "mapped back" to lower-layer headers and/or sequence information in such as way as to establish a relationship between information within various layers. For example, data concerning a particular protein product that is expressed in a certain tissue type (i.e., protein layer information) may also provide information relating to splicing (i.e., RNA layer information) or to a SNP at the genomic level (i.e., DNA layer information) resulting in a premature termination codon. In another case, the diagnosis of a certain disease in a certain patient or, for example, results from a mammogram screen or prostate-specific antigen results, may provide data directly related to hypermethylation of certain regions of the DNA sequence segment included within a DNA layer biological data unit. These epigenetic markers, along with the methylation profile at CpG islands associated with certain genes, could provide crucial BioIntelligent™ biologically-relevant information to relate and correlate with appropriate gene and disease conditions.

One advantage of the layered architecture of the data containers 2264 is that modification or updating of the data content associated with a given layer has minimal or no effect on the processing of data in the remaining layers. In one embodiment layers are advantageously designed to be operated on independently while retaining the capability to integrate, and interoperate with, data and knowledge of other layers. In addition, data can be organized within each data container 2264 in accordance with the requirements of specific applications. For example, a data model designed for oncology studies would include "hooks" to facilitate interaction directly with certain clinical data types and would enable mapping to occur directly between genomic, transcriptomic and proteomic data. As a consequence, the information contained within BioIntelligent™ biologically-relevant headers may be specific to certain applications. For example, the BioIntelligent™ biologically-relevant headers associated with the layered database model developed for a particular application could include an application interface for data types such as, for example, images obtained from X-ray, mammography, computed tomography, ultrasound and MRI imaging processes. All or part of this data may be mapped, via relationships between information within BioIntelligent™ biologically-relevant headers associated with different layers of a data model, to a disease condition capable of being associated with a region of segmented DNA sequence data contained within a biological data unit. This enables biological data units to be grouped and analyzed based upon the classification schema required by a particular application.

In a stage 2290, biological data units encapsulated with BioIntelligent™ biologically-relevant headers and stored with the data containers 2264 may subsequently be filtered, sorted or operated upon based on information included within such headers. The layered structure of biological data units comprised of biological data units including encapsulated BioIntelligent™ biologically-relevant headers enables querying of the information included within one or more such headers to be performed and results returned based upon a set of rules specified by, for example, the application issuing the query.

Figure 23:
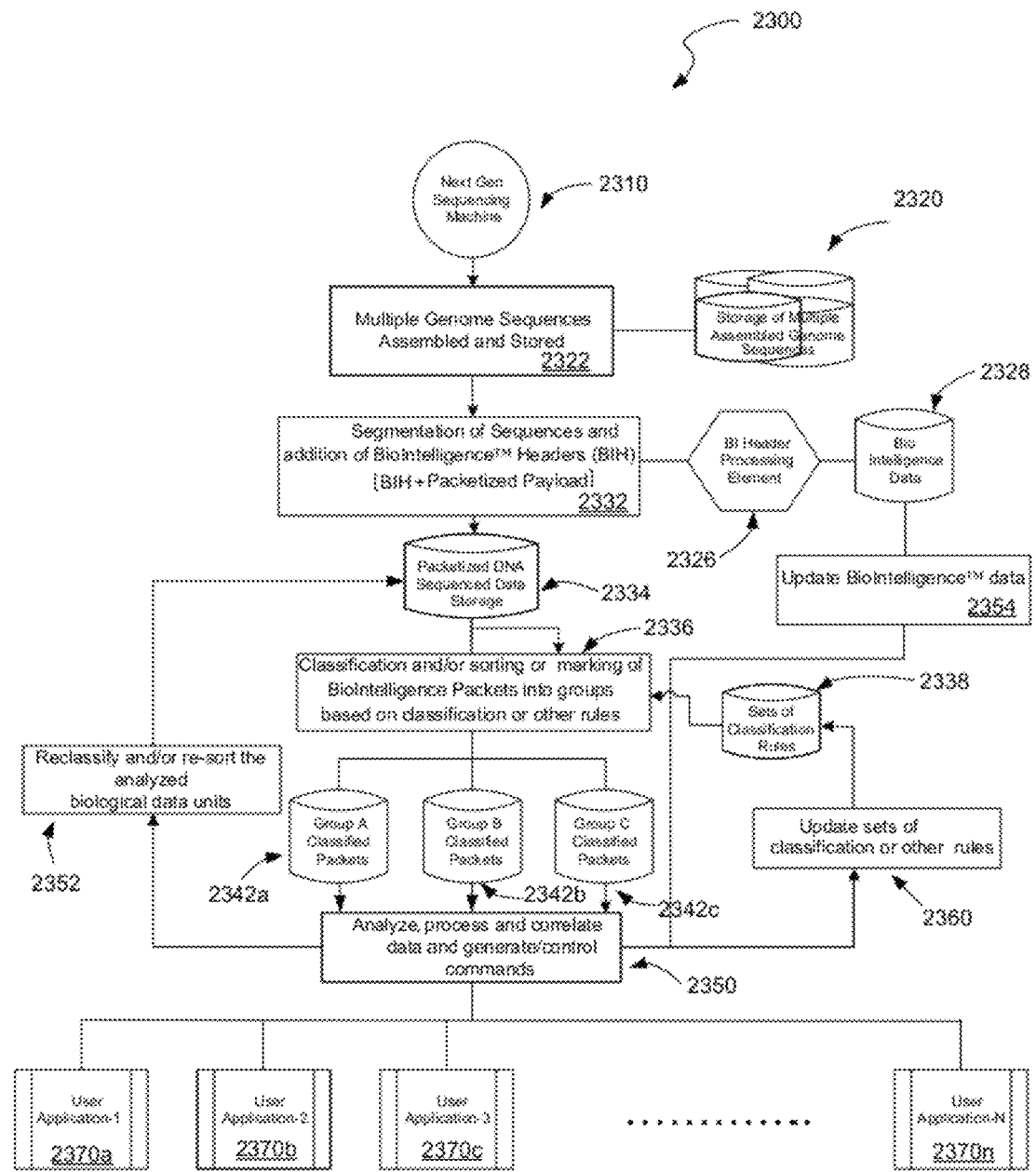
FIG. 23 illustrates an exemplary process for grouping and classification of biological data units having BioIntelligent™ biologically-relevant headers.

Attention is now directed to FIG. 23, which illustrates an exemplary process 2300 for grouping and classification of biological data units having BioIntelligent™ biologically-relevant headers. In a stage 2310, DNA sequence data from multiple individuals or specimens is generated using, for example, a high-speed sequencing machine and assembled within storage 2320 into multiple assembled genome sequences. These sequences then undergo an alignment process pursuant to which they aligned with other genome sequences from same species. The correctly aligned sequence data is then stored in a separate storage repository 2322.

In a stage 2326, BioIntelligent™ biologically-relevant data stored within a storage unit 2328 is mapped into BioIntelligent™ biologically-relevant headers containing information specific to ones of the particular DNA sequences or other segment within storage repository 2322. In a stage 2332, the aligned genome sequences are accessed from storage repository 2322 and segmented and the sequence segments encapsulated with such BioIntelligent™ biologically-relevant headers in the manner described with respect FIG. 22 and elsewhere herein. The resulting biological data units are then stored within storage 2334. The biological data units stored within storage 2334 are suited for BioIntelligent™ biologically-relevant-based processing, analysis and transmission between networked processing nodes. Such processing and analysis may include, for example, sorting and grouping ones of the biological data units based upon the information contained within the BioIntelligent™ biologically-relevant headers thereof In a stage 2336, the biological data units within storage 2334 are classified, organized or grouped based on a given set of classification rules 2338. For example, in the embodiment of FIG. 23 the biological data units within storage 2334 are grouped into a plurality of groups, i.e., Group A, Group B and Group C, and stored within corresponding storage containers 2342. Classification of these biological data units is facilitated by the association of sequence segments with headers containing information from the scientific community that has, for example, been demonstrated to be directly or indirectly related to that specific DNA sequence represented in the payload sections encapsulated by such headers.

Biological data units may be grouped or classified using several different schemas. For example, data units may be grouped based on whether on not genes contained within their respective payloads have any association with a disease such as a neurological disorder or a particular cancer. Since this type of information may be included within a BioIntelligent™ biologically-relevant header, it is possible to classify data units based on disease association and then to apply certain additional rules to further classify and group the data units. As a specific example, all data units containing fragments of genes associated with cancer which have a minimum of three introns and show at least one alternative splicing event in the cancerous tissue or cell type could be grouped together. Alternatively, classification could based upon one or more rules specifying the grouping of data units containing fragments of cancer-associated genes including a given number of SNPs and a premature termination codon. It is observed that either of the above two classification schemes could identify truncated gene products having reduced or null activity or a negative toxic effect which are intimately involved in disease onset. However, only the SNP classification scheme might identify mutations that alter microRNA target sites and affect microRNA activity in a manner consistent with disease onset and/or progression. However, neither of the above schemes would yield information relating to hypermethylation involved in cancer causation, and obtaining such information would require use of an alternative classification criteria.

In a stage 2350, the data units stored within the containers 2342 may be accessed, processed and analyzed in accordance with instructions provided by an application 2370. Based upon the results of this analysis, the data units may be updated and reclassified 2352 for improved resolution of analysis. In addition, as new BioIntelligent™ biologically-relevant data becomes available (stage 2354), either as a result of the analysis occurring during stage 2350 or otherwise, the sets of classification rules 2338 may also be updated (stage 2360) to improve aspects of the processing and analysis.

In one embodiment a determination may be made as to the appropriateness and validity of the results of the processing occurring during stage 2350 based upon quality criteria established by one or more of the specific application 2370 and user definitions. In particular, once the biological data units have been classified and grouped, certain post-processing operations may be performed in order to determine the need or benefit of reclassification and/or updating of intelligence data. The decision of whether to reclassify, update or change classification rules, or update the BioIntelligent™ biologically-relevant data, will typically be made based on the quality of results obtained. For example, the classification rules that are used in the above example would not intentionally select biological data units containing portions of a cancer gene involved in a translocation event arising from a chromosomal rearrangement. Accordingly, a translocation event resulting in a premature termination codon, or a deletion producing a truncated protein product, would not be included in the preceding classification directed to cancer-associated genes. As a consequence, a user or application would likely opt to have the biological data units under evaluation reclassified based upon updated classification rule sets.

Summary of Certain Features of the Disclosed Embodiments

In one aspect the BioIntelligent™ biologically-relevant included within the headers of biological data units may include knowledge and information pertaining to DNA, RNA, protein and other biological polymers and systems including, without limitation, data collected from microarray studies, high-throughput DNA sequencing data (including deep sequencing data), and mass spectrometry data.

In another aspect, disclosed is a method to characterize data from different areas of molecular biology including, without limitation, knowledge, information fields or any data type organized within a biological data model such as that depicted in FIG. 16.

In another aspect, disclosed is a method of using BioIntelligent™ biologically-relevant headers in the design and development of a normalized data structure or data model in a multi-layered and multi-dimensional format.

Also disclosed is a BioClassifier™ classification scheme for classifying BioIntelligent™ biologically-relevant headers based on a set of rules defined by a user and/or an application in a manner consistent with current and future application usage. In this regard user-defined classification groups may be employed to classify BioIntelligent™ biologically-relevant headers for optimal performance. Further, the classification can be performed based on set rules to filter biological data units including BioIntelligent™ biologically-relevant headers in view of application requirements. In one embodiment the set rules utilized for classification purposes may comprise, for example, access control lists used in filtering of BioIntelligent™ biologically-relevant headers.

In another aspect, disclosed is the use of the BioClassifier™ classification scheme to design and manage a group of biological data units through marking (whether policy-based or otherwise) and policing of the content of such data units. Such marking and policing of biological data units may enhance the efficiency with which BioIntelligent™ biologically-relevant may be used to extract new research and clinical data of relevance from existing as well as future data pools.

In another aspect, disclosed is the placement and ordering of BioIntelligent™ biologically-relevant-based biological data units into a single or multiple queues for processing based on, for example, the available bandwidth per processing data path element. This approach may be employed when, for example, multiple applications are engaged in processing the biological data units within a data container accessible through only a single data path. Such a queued structure above may be rate limited, scheduled, managed, controlled and/or dropped based upon the quality of services demanded by the applications operating upon the biological data sequences included within the data container.

Also disclosed is the embedding as BioIntelligent™ biologically-relevant data any type of information, knowledge, intelligence, related or arbitrary sequences or any other data including, for example, images/scans, clinical, medical, gene expression, financial, environmental or research data into a representation of molecular sequence data relating to, for example, RNA, DNA, protein, polysaccharides, lipid chains or any other biological polymer or combination of polymers. As described herein, such embedding may enable high-speed, high-performance processing, analysis and management of such sequence data.

In another aspect, disclosed herein is the use of BioIntelligent™ biologically-relevant headers embedded in a biological sequence to, for example, find, align, reveal or lookup related, unrelated and correlated relevant data for biological, genetic, epigenetic, expression, medical, behavioral, psychological, social or other applications. Such BioIntelligent™ biologically-relevant headers or tags may, for example, be embedded within a biological sequence or, alternatively, be related or associated with such sequences in the same or a different format. Such an association or relationship may be defined using, for example, a pointer (e.g., in the form of a pointer mechanism, look up table, or other associated construct). The embedded or associated BioIntelligent™ biologically-relevant headers may facilitate the implementation of any method, procedure or application disposed to process, sort, filter, route, manage or analyze biological or other sequence data.

In another aspect, disclosed is the use of BI headers as an innovative component part of a data set utilized in database representations to enhance the speed and efficiency by which large quantities of genetic and other biological sequence data produced by current and next-generation sequencing apparatus are transported, analyzed, processed, managed and translated. Such data may include, for example, microarray gene expression data, deep sequencing data, mass spectrometry data, copy-number variation data, alternative splicing data and SNP data relate to disease conditions and other aspects of molecular biology.

Also disclosed is the association of BioIntelligent™ biologically-relevant headers, tags or any other information with either an entire biological sequence or segments thereof in order to create a layered architecture capable of facilitating a layered approach to biological data processing. Such a layered architecture may be used to systematically create a database or tables in an ordered or structured format, or in connection with any other hierarchical or non hierarchical format for processing biological sequence data for data analysis, processing, management, transportation and storage.

In yet another aspect, disclosed herein is the use of BioIntelligent™ biologically-relevant headers or any other type or form of headers or tags for the creation of biological process layers in a multi-dimensional data format. Also disclosed is a method in which a structured or multi-dimensional architecture, platform or system model which may be used for, without limitation, bioinformatics or medical informatics processing or analysis. Such a layered architecture, platform or system model may scale to accommodate current and future improvement, discoveries or technology-advancements by enabling changes to be made to certain layers without requiring that corresponding modifications be made to content within other layers. That is, the layers may be defined such that each independent layer can be modified independently, rendering the making such changes transparent to other layers. Of course, the information within various layers may be linked or otherwise mutually associated in the manner described herein, thereby enabling those layers linked or otherwise associated with a layer which has been modified to be beneficially informed by such modification. This approach enables ongoing enhancement of the information within each individual layer without necessarily affecting the content of other layers.

In another aspect, disclosed is a header design which may be used in a multi-plane and multi-dimensional layered architecture (see, e.g. FIG. 16). This will enable easy and highly-interactive access to data types associated with, for example, "gene-level" model layers to higher-level layers containing environmentally-relevant data. The following describes a set of relationships which could exist among and between data model layers in an exemplary embodiment:

a) The BioIntelligent™ information at the DNA layer associated with all genes is able to functionally interact with all higher-layer BioIntelligent™ information relating to transcription and regulation of any specific gene.

b) All of the functionally interactive information in (a) can be processed along with any protein-layer data for any gene.

c) Data from (a) and (b) may be processed by a function associated with a given layer in order to enable definition of genes and gene products involved in molecular pathways and any molecular interdependent relations between pathways. Related data on SNPs, alternative splicing and other mutational events as they relate to certain diseases may, in this specific example, be processed in a control plane for complete interoperability and user definition. In addition, metabolomics data might be accessed at this layer.

d) Since (c) provides access to data at the level of organs, image data generated from mammograms, MRI procedures, x-rays, CT scans and related scans and images may be integrated into such data. These images may provide important information relative to disease diagnosis, prognosis and disease progression, and may now relate and be processed directly with data associated with the DNA layer in a fully interactive approach.

e) A complete systems biology profile may now be determined. This enables data from systems and organs to be processed and analyzed in combination with related data in the DNA layer. In addition, this allows for data collected at the organism level to be integrated into the DNA sequence data. Such organism-layer data could include, for example, data included within all types of records pertaining to individuals such as health history and medical records. In various embodiments social, physical, mental, emotional and environmental data could also be included within the organism-layer data.

f) The data associated with layers described in (a) through (e) may be recorded in a multidimensional format, interact, and be processed as a single pool of data in the manner described herein. This facilitates, for example, the processing of data concerning the expression level of a certain gene along with data relating to the environmental exposure of the subject organism.

In yet another aspect, disclosed an apparatus configured for sorting and filtering packetized DNA sequence data. The apparatus includes:

a non-volatile storage element containing biological data units, each of which includes header information that has been marked and classified and a payload comprised of DNA sequence data;

a volatile storage element;

a fast plane storage element for framing the marked and classified biological data units;

a first controller element including a first tier storage element, a first tier processor element and a first tier switching element;

a second controller element including a second tier storage element, a second tier processor element and a second tier switching element;

a general purpose processing element;

an FPGA or ASIC unit for processing the marked and classified biological data units, such unit including a content-addressable memory element, a bioinformatics-specific processing element, a switching element and a micro processor element;

a data manager unit; and a general purpose data switching element.

In one aspect the present disclosure has described, inter alia, a system and method for classifying biological data units through the evaluation of the BioIntelligent™ biologically-relevant headers of such data units in accordance with rules and criteria defined by a user and/or application. It will be appreciated that such classification may be performed by filtering biological data units in accordance with a set of rules developed consistently with requirements of particular applications. For example, such a set of rules may be in the form of one or more access control lists used to filter biological data units for further required processing.

It will be further appreciated that the classification techniques described herein may facilitate policy-based or other marking of biological data units to improve processing efficiency and enable the extraction of relevant clinical and other data from existing and future pools of data represented using such biological data units.

The biological data units described herein may also be ordered within single and/or multiple queues to be processed based upon the available processing bandwidth in one or more data paths. For example, such ordered queuing may be appropriate when multiple applications require access over a single data path to the biological data units recorded within one or more data containers. Such queuing may be shaped (rate limited), scheduled, managed, controlled and/or dropped based on quality of services demanded by the applications operating on the biological data units recorded in the one or more containers.

The word "exemplary" is used herein to mean "serving as an example, instance, or illustration." Any embodiment described herein as "exemplary" is not necessarily to be construed as preferred or advantageous over other embodiments.

In one or more exemplary embodiments, the functions, methods and processes described may be implemented in hardware, software, firmware, or any combination thereof. If implemented in software, the functions may be stored on or encoded as one or more instructions or code on a computer-readable medium. Computer-readable media includes computer storage media. Storage media may be any available media that can be accessed by a computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer. Disk and disc, as used herein, includes compact disc (CD), laser disc, optical disc, digital versatile disc (DVD), floppy disk and blu-ray disc where disks usually reproduce data magnetically, while discs reproduce data optically with lasers. Combinations of the above should also be included within the scope of computer-readable media.

It is understood that the specific order or hierarchy of steps or stages in the processes and methods disclosed are examples of exemplary approaches. Based upon design preferences, it is understood that the specific order or hierarchy of steps in the processes may be rearranged while remaining within the scope of the present disclosure. The accompanying method claims present elements of the various steps in a sample order, and are not meant to be limited to the specific order or hierarchy presented.

Those of skill in the art would understand that information and signals may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof Those of skill would further appreciate that the various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present disclosure.

The various illustrative logical blocks, modules, and circuits described in connection with the embodiments disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

The steps or stages of a method, process or algorithm described in connection with the embodiments disclosed herein may be embodied directly in hardware, in a software module executed by a processor, or in a combination of the two. A software module may reside in RAM memory, flash memory, ROM memory, EPROM memory, EEPROM memory, registers, hard disk, a removable disk, a CD-ROM, or any other form of storage medium known in the art. An exemplary storage medium is coupled to the processor such the processor can read information from, and write information to, the storage medium. In the alternative, the storage medium may be integral to the processor. The processor and the storage medium may reside in an ASIC. The ASIC may reside in a user terminal. In the alternative, the processor and the storage medium may reside as discrete components in a user terminal.

The previous description of the disclosed embodiments is provided to enable any person skilled in the art to make or use the present disclosure. Various modifications to these embodiments will be readily apparent to those skilled in the art, and the generic principles defined herein may be applied to other embodiments without departing from the spirit or scope of the disclosure. Thus, the present disclosure is not intended to be limited to the embodiments shown herein but is to be accorded the widest scope consistent with the principles and novel features disclosed herein. It is intended that the following claims and their equivalents define the scope of the disclosure.

---

We claim:

1. A biological sequence processing system, comprising:
a network interface configured to receive a query;
a data container having a data structure which facilitates processing of biological sequence data in the biological sequence processing system, the data container including a plurality of biological data units associated with the data container, each of the plurality of biological data units being packetized and used within the processing system and including:
a payload containing segmented biological sequence data,
a first BioIntelligent™ header associated with biological information relating to the segmented biological sequence data wherein the first BioIntelligent™ header identifies a first biological characteristic associated with a first subset of the segmented biological sequence data, and
a second BioIntelligent™ header identifying a second biological characteristic associated with a second subset of the segmented biological sequence data; and
a processor for executing codes of a computer program to:
process the query by querying at least one of the first BioIntelligent™ header and the second BioIntelligent™ header of at least one of the plurality of biological data units without examining the payload of the at least one of the plurality of biological data units, thereby improving computational efficiency; and generate a response to the query using at least one of the first BioIntelligent™ header of the at least one of the plurality of biological data units and the second BioIntelligent™ header of the at least one of the plurality of biological data units;
wherein the network interface at least one of transmits and receives a signal containing a data packet including the response to the query.

2. The biological sequence processing system of claim 1 wherein the segmented biological sequence data comprises segmented genomic sequence data.

3. The biological sequence processing system of claim 1 wherein the at least one header is linked to the segmented biological sequence data.

4. The biological sequence processing system of claim 1 wherein the biological information identifies one or more portions of the segmented biological sequence data associated with a disease condition.

5. The biological sequence processing system of claim 1 wherein the biological information comprises one or more characteristics of the segmented biological sequence data.

6. The biological sequence processing system of claim 5 wherein the segmented biological sequence data comprises a segment of DNA sequence data.

7. The biological sequence processing system of claim 6 wherein the one or more characteristics relate to a property of the segment of DNA sequence data.

8. The biological sequence processing system of claim 7 wherein the property comprises a number of exons included within the segment of DNA sequence data.

9. The biological sequence processing system of claim 7 wherein the property comprises locations of exons included within the segment of DNA sequence data.

10. The biological sequence processing system of claim 7 wherein the property relates to an extent of methylation within the segment of DNA sequence data.

11. The biological sequence processing system of claim 7 wherein the property comprises one or more molecular pathways associated with the segment of DNA sequence data.

12. The biological sequence processing system of claim 7 wherein the property relates to one or more gene mutations within the segment of DNA sequence data.

13. The biological sequence processing system of claim 7 wherein the property relates to an association of a disease condition with the one or more gene mutations.

14. The biological sequence processing system of claim 13 wherein the first header includes first biological information relating to a property of the first segment of biological sequence data.

15. The biological sequence processing system of claim 14 wherein the first header includes second biological information relating to a property of the second segment of biological sequence data.

16. The biological sequence processing system of claim 1 wherein:
a first of the plurality of biological data units includes a first segment of biological sequence data and a first header;
a second of the plurality of biological data units includes a second segment of biological sequence data and a second header; and
wherein the first header includes first biological information relating to a property of the second segment of biological sequence data.

17. The biological sequence processing system of claim 16 wherein the first segment of biological sequence data comprises a first segment of DNA sequence data.

18. The biological sequence processing system of claim 17 wherein the property corresponds to a mutation of a gene included within the second segment of biological sequence data.

19. The biological sequence processing system of claim 18 wherein the mutation has an effect upon expression of a gene product associated with the first segment of DNA sequence data.

20. The biological sequence processing system of claim 19 wherein the second segment of biological sequence data comprises a segment of microRNA sequence data.

21. The biological sequence processing system of claim 16 wherein the second segment of biological sequence data comprises a second segment of DNA sequence data.

22. The biological sequence processing system of claim 21 wherein the second segment of biological sequence data comprises a first segment of RNA sequence data.

23. The biological sequence processing system of claim 16 wherein a third of the plurality of biological data units includes a third segment of biological sequence data and a third header wherein the first header points to the third header.

24. The biological sequence processing system of claim 1 wherein:
a first of the plurality of biological data units includes a first segment of biological sequence data and a first header;
a second of the plurality of biological data units includes a second segment of biological sequence data and a second header; and
a third of the plurality of biological data units includes a third segment of biological sequence data and a third header;
wherein the first header points to the second header and the second header points to the third header.

25. The biological sequence processing system of claim 24 wherein the first header also points to the third header.

26. The biological sequence processing system of claim 1 wherein the segmented biological sequence data within at least one of the plurality of biological data units comprises synthetic biological sequence data.

27. A polymeric sequence processing system, comprising:
a network interface configured to receive a query;
a data container having a data structure which facilitates processing of polymeric sequence data in the polymeric sequence processing system, the data container including a plurality of polymeric data units associated with the data container, each of the plurality of polymeric data units being packetized for and used within the processing system and including:
a payload containing segmented polymeric sequence data,
a first BioIntelligent™ header associated with information relating to the segmented polymeric sequence data wherein the first BioIntelligent™ header identifies a first biological characteristic associated with a first subset of the segmented polymeric sequence data, and
a second BioIntelligent™ header identifying a second biological characteristic associated with a second subset of the segmented polymeric sequence data;
a processor for executing codes of a computer program to:
process the query by querying at least one of the first BioIntelligent™ header and the second BioIntelligent™ header of at least one of the plurality of polymeric data units and without examining the payload of the at least one of the plurality of polymeric data units, thereby improving computational efficiency; and generate a response to the query using at least one of the first BioIntelligent™ header of the at least one of the plurality of polymeric data units and the second BioIntelligent™ header of the at least one of the plurality of polymeric data units;

wherein the network interface at least one of transmits and receives a signal containing a data packet including the response to the query.

28. The polymeric sequence processing system of claim 27 wherein the segmented polymeric sequence data comprises segmented biopolymeric sequence data.

29. The polymeric sequence processing system of claim 27 wherein the at least one header is linked to the segmented polymeric sequence data.

30. A biological sequence processing system, comprising:
a network interface;
a data container having a data structure which facilitates processing of biological sequence data within the biological sequence processing system, the data container including:
a plurality of biological data units associated with the data container, each of the plurality of biological data units being packetized and used within the processing system and including:
a payload containing segmented biological sequence data, and
a set of BioIntelligent™ headers associated with information relating to the segmented biological sequence data wherein a first BioIntelligent™ header within the set of BioIntelligent™ headers identifies a first biological characteristic associated with a first subset of the segmented biological sequence data and a second BioIntelligent™ header within the set of BioIntelligent™ headers identifies a second biological characteristic associated with a second subset of the segmented biological sequence data; and
a processor for executing codes of a computer program to:
process the query by querying at least one of the first BioIntelligent™ header and the second BioIntelligent™ header of at least one of the plurality of biological data units without examining the payload of the at least one of the plurality of biological data units, thereby improving computational efficiency; and
generate a response to the query using at least one of the first BioIntelligent™ header of the at least one of the plurality of biological data units and the second BioIntelligent™ header of the at least one of the plurality of biological data units;
wherein the network interface at least one of transmits and receives a signal containing a data packet including the response to the query.

31. The biological sequence processing system of claim 30 wherein the segmented biological sequence data comprises segmented genomic sequence data.

32. The biological sequence processing system of claim 31 wherein at least a portion of the information comprises gene expression data.

33. The biological sequence processing system of claim 31 wherein at least a portion of the information comprises microarray data.

34. The biological sequence processing system of claim 30 wherein the set of headers for each one of the biological data units is linked to the segmented biological sequence data for each said one of the biological data units.

35. The biological sequence processing system of claim 30 wherein each header included within each set of headers is associated with one of a plurality of layers of a biological data model.

36. The biological sequence processing system of claim 35 wherein a first of the plurality of layers comprises a DNA layer.

37. The biological sequence processing system of claim 35 wherein a second of the plurality of layers comprises an RNA layer.

38. The biological sequence processing system of claim 37 wherein a third of the plurality of layers comprises a peptide layer.

39. The biological sequence processing system of claim 35 wherein one of the plurality of layers comprises a DNA layer.

40. The biological sequence processing system of claim 35 wherein one of the plurality of layers comprises an RNA layer.

41. The biological sequence processing system of claim 35 wherein one of the plurality of layers comprises a peptide layer.

42. The biological sequence processing system of claim 35 wherein one of the plurality of layers comprises a field-specific layer.

43. The biological sequence processing system of claim 35 wherein one of the plurality of layers comprises an application layer.

44. The biological sequence processing system of claim 35 wherein one of the plurality of layers comprises a user-specific layer.

45. The biological sequence processing system of claim 35 wherein a first of the plurality of layers comprises a DNA layer.

46. The biological sequence processing system of claim 45 wherein the information associated with one header of the set of headers relating to the DNA layer comprises methylation pattern information.

47. The biological sequence processing system of claim 45 wherein the information associated with one header of the set of headers relating to the DNA layer comprises chromosomal rearrangement information.

48. The biological sequence processing system of claim 45 wherein the information associated with one header of the set of headers relating to the DNA layer comprises at least one of an exon starting location and an exon ending location within the segmented biological sequence data.

49. The biological sequence processing system of claim 45 wherein the information associated with one header of the set of headers relating to the DNA layer comprises a number of exons included within the segmented biological sequence data.

50. The biological sequence processing system of claim 45 wherein the information associated with one header of the set of headers relating to the DNA layer represents at least one gene mutation in the segmented biological sequence data associated with a disease.

51. The biological sequence processing system of claim 45 wherein the information associated with one header of the set of headers relating to the DNA layer identifies at least one gene within the segmented biological sequence data.

52. The biological sequence processing system of claim 45 wherein the information associated with one header of the set of headers relating to the DNA layer identifies at least one of a tissue type and a cell type.

53. The biological sequence processing system of claim 45 wherein the information associated with one header of the set of headers relating to the DNA layer identifies one or more open reading frames within the segmented biological sequence data.

54. The biological sequence processing system of claim 45 wherein the information associated with one header of the set of headers relating to the DNA layer identifies at least one of a start position and an end position of the segmented biological sequence data.

55. The biological sequence processing system of claim 45 wherein the information associated with one header of the set of headers relating to the DNA layer identifies the segmented biological sequence data as being one of chromosomal and mitochondrial.

56. The biological sequence processing system of claim 45 wherein the information associated with one header of the set of headers relating to the DNA layer identifies at least one of a genus and a species of an organism from which the segmented biological sequence data originated.

57. The biological sequence processing system of claim 30 wherein a first of the plurality of biological data units includes a first set of headers wherein a first header of the first set of headers contains information relating to an alternative splicing event associated with one of a disease and a phenotype.

58. The biological sequence processing system of claim 30 wherein:
a first of the plurality of biological data units includes a first segment of biological sequence data and a first set of headers;
a second of the plurality of biological data units includes a second segment of biological sequence data and a second set of headers; and
wherein at least one of the first set of headers includes first biological information relating to at least one property of the second segment of biological sequence data.

59. The biological sequence processing system of claim 58 wherein a fourth of the plurality of layers comprises a field-specific layer.

60. The biological sequence processing system of claim 59 wherein a fifth of the plurality of layers comprises an application layer.

61. The biological sequence processing system of claim 30 wherein at least a portion of the information comprises medical records data.

62. The biological sequence processing system of claim 30 wherein at least a portion of the information comprises molecular pathways information.

63. The biological sequence processing system of claim 30 wherein the information is contained within each said set of headers.

64. The biological sequence processing system of claim 30 wherein a header included within at least one said set of headers includes a pointer to a location in a memory storing at least a part of the information.

65. The biological sequence processing system of claim 30 wherein the segmented biological sequence data for each of the biological data units is stored within a first memory element and the set of headers for each of the biological data units is stored within a second memory element.

66. The biological sequence processing system of claim 30 wherein the segmented biological sequence data comprises a sequence of nucleotide bases wherein each of the nucleotide bases is represented in a two-bit format.

67. The biological sequence processing system of claim 30 wherein the information comprises one or more of medical, clinical, pharmaceutical, environmental and experimental data.

68. The biological sequence processing system of claim 67 wherein the information further includes test results.

69. The biological sequence processing system of claim 30 wherein the segmented biological sequence data within at least one of the plurality of biological data units comprises synthetic biological sequence data.

70. A sequence processing system, comprising:
a network interface;
a data container having a data structure which facilitates processing of monomer sequence data within the sequence processing system, the data container including:
a plurality of polymeric data units associated with the data container, each of the plurality of polymeric data units being packetized and used within the processing system and including:
a payload containing a representation of at least a portion of a monomer sequence of a polymeric molecule, and
a set of BioIntelligent™ headers associated with information relating to the at least a portion of the monomer sequence wherein a first BioIntelligent™ header within the set of BioIntelligent™ headers identifies a first biological characteristic associated with a first subset of the monomer sequence and a second BioIntelligent™ header within the set of BioIntelligent™ headers identifies a second biological characteristic associated with a second subset of the monomer sequence; and
a processor for executing codes of a computer program to:
process the query by querying at least one of the first BioIntelligent™ header and the second BioIntelligent™ header of at least one of the plurality of polymeric data units without examining the payload of the at least one of the plurality of polymeric data units, thereby improving computational efficiency; and
generate a response to the query using at least one of the first BioIntelligent™ header of the at least one of the plurality of polymeric data units and the second BioIntelligent™ header of the at least one of the plurality of polymeric data units;
wherein the network interface at least one of transmits and receives a signal containing a data packet including the response to the query.

71. The sequence processing system of claim 70 wherein a header included within at least one said set of headers includes a pointer to a location in a memory storing at least a part of the information.

72. A biological sequence processing system, comprising:
a network interface;
a data container having a data structure which facilitates processing of biological sequence data within the biological sequence processing system, the data container including:
a first biological data unit associated with the data container wherein the first biological data unit includes first segmented biological sequence data and a first BioIntelligent™ header identifying a first biological characteristic associated with a first subset of the first segmented biological sequence data and a second BioIntelligent™ header identifying a second biological characteristic associated with a second subset of the first segmented biological sequence data, the first BioIntelligent™ header being different from the first segmented biological sequence data and identifying a first type of organism associated with the first biological sequence data; and a second biological data unit associated with the data container wherein the second biological data unit includes second segmented biological sequence data and a third BioIntelligent™ header identifying a third biological characteristic associated with a first subset of the second segmented biological sequence data and a fourth BioIntelligent™ header identifying a fourth biological characteristic associated with a second subset of the second segmented biological sequence data, the third BioIntelligent™ header being different from the second segmented biological sequence data and identifying a second type of organism associated with the second biological sequence data wherein the first type of organism is different from the second type of organism; and a processor for executing codes of a computer program to:
process the query by querying at least one of the first BioIntelligent™ header and the second BioIntelligent™ header without examining the first segmented biological sequence data, thereby improving computational efficiency; and
generate a response to the query using at least one of the first BioIntelligent™ header and the second BioIntelligent™ header;
wherein the network interface at least one of transmits and receives a signal containing a data packet including the response to the query.

73. The biological sequence processing system of claim 72 wherein the first type of organism comprises *homo sapiens*.

74. The biological sequence processing system of claim 73 wherein the second type of organism comprises bacteria.

75. The biological sequence processing system of claim 72 wherein the first biological data unit further includes a first plurality of headers, each of the first plurality of headers being associated with information relating to the first biological sequence data.

76. The biological sequence processing system of claim 75 wherein each header included within the first plurality of headers is associated with one of a plurality of layers of a biological data model.

77. The biological sequence processing system of claim 72 wherein the first biological sequence data comprises genomic sequence data.

78. A sequence data processing system including a data container having a data structure which accommodates polymeric sequence data, the sequence data processing system comprising:
a network interface;
a computer program product comprising a computer-readable medium including codes for causing the processor to:
receive, from a network-connected source of polymeric sequence data, segmented polymeric sequence data;
generate a plurality of polymeric data units, each of the plurality of polymeric data units including:
a payload containing segmented polymeric sequence data,
a first BioIntelligent™ header identifying a first biological characteristic associated with a first subset of the segmented polymeric sequence data and a second BioIntelligent™ header identifying a second biological characteristic associated with a second subset of the segmented polymeric sequence data;
store the plurality of polymeric data units within the data container; and
a processor for executing codes of a computer program to:
process the query by querying at least one of the first BioIntelligent™ header and the second BioIntelligent™ header of at least one of the plurality of polymeric data units without examining the payload of the at least one of the plurality of polymeric data units, thereby improving computational efficiency; and
generate a response to the query using at least one of the first BioIntelligent™ header of the at least one of the plurality of polymeric data units and the second BioIntelligent™ header of the at least one of the plurality of polymeric data units;
wherein the information is different from the segmented polymeric sequence and wherein the network interface at least one of transmits and receives a signal containing a data packet including the response to the query.

* * * * *

SEQUENCE LISTING

```
<160> NUMBER OF SEQ ID NOS: 32

<210> SEQ ID NO 1
<211> LENGTH: 20
<212> TYPE: DNA
<213> ORGANISM: Unknown
<220> FEATURE:
<223> OTHER INFORMATION: Example sequence fragment

<400> SEQUENCE: 1
acgccgtaac gggtaattca                                              20

<210> SEQ ID NO 2
<211> LENGTH: 30
<212> TYPE: DNA
<213> ORGANISM: Unknown
<220> FEATURE:
<223> OTHER INFORMATION: Example nucleotide sequence

<400> SEQUENCE: 2
ccggtccagg ggacgcgacc aaaaagccca                                   30

<210> SEQ ID NO 3
<211> LENGTH: 30
<212> TYPE: DNA
<213> ORGANISM: Unknown
<220> FEATURE:
<223> OTHER INFORMATION: Example nucleotide sequence

<400> SEQUENCE: 3
ccagtccagg aaaaacgacg cgaccgccca                                   30

<210> SEQ ID NO 4
<211> LENGTH: 20
<212> TYPE: DNA
```

```
<213> ORGANISM: Unknown
<220> FEATURE:
<223> OTHER INFORMATION: Example nucleotide sequence

<400> SEQUENCE: 4
aagccgtaac gggtaattcg                                               20

<210> SEQ ID NO 5
<211> LENGTH: 20
<212> TYPE: DNA
<213> ORGANISM: Unknown
<220> FEATURE:
<223> OTHER INFORMATION: Example nucleotide sequence

<400> SEQUENCE: 5
acgacgtaac gggtaattcg                                               20

<210> SEQ ID NO 6
<211> LENGTH: 20
<212> TYPE: DNA
<213> ORGANISM: Unknown
<220> FEATURE:
<223> OTHER INFORMATION: Example nucleotide sequence

<400> SEQUENCE: 6
acgacgtatc gggtaattca                                               20

<210> SEQ ID NO 7
<211> LENGTH: 20
<212> TYPE: DNA
<213> ORGANISM: Unknown
<220> FEATURE:
<223> OTHER INFORMATION: Example nucleotide sequence

<400> SEQUENCE: 7
acgacgtatc gggtaataca                                               20

<210> SEQ ID NO 8
<211> LENGTH: 20
<212> TYPE: DNA
<213> ORGANISM: Unknown
<220> FEATURE:
<223> OTHER INFORMATION: Example nucleotide sequence

<400> SEQUENCE: 8
acgacgtaac gggtaattca                                               20

<210> SEQ ID NO 9
<211> LENGTH: 30
<212> TYPE: DNA
<213> ORGANISM: Unknown
<220> FEATURE:
<223> OTHER INFORMATION: Example nucleotide sequence

<400> SEQUENCE: 9
gggggggggg gggggggggg gggggggggg                                    30

<210> SEQ ID NO 10
<211> LENGTH: 30
<212> TYPE: DNA
<213> ORGANISM: Unknown
<220> FEATURE:
<223> OTHER INFORMATION: Example nucleotide sequence

<400> SEQUENCE: 10
gggggggggg gggtgggggg gggggggggg                                    30
```

<210> SEQ ID NO 11
<211> LENGTH: 3000
<212> TYPE: DNA
<213> ORGANISM: Unknown
<220> FEATURE:
<223> OTHER INFORMATION: Example nucleotide sequence
<220> FEATURE:
<221> NAME/KEY: misc_feature
<222> LOCATION: (21)..(2990)
<223> OTHER INFORMATION: May be a known sequence from a particular
      strain of influenza virus

<400> SEQUENCE: 11

```
gggggggggg ggggtggggg nnnnnnnnnn nnnnnnnnnn nnnnnnnnnn nnnnnnnnnn    60
nnnnnnnnnn nnnnnnnnnn nnnnnnnnnn nnnnnnnnnn nnnnnnnnnn nnnnnnnnnn   120
nnnnnnnnnn nnnnnnnnnn nnnnnnnnnn nnnnnnnnnn nnnnnnnnnn nnnnnnnnnn   180
nnnnnnnnnn nnnnnnnnnn nnnnnnnnnn nnnnnnnnnn nnnnnnnnnn nnnnnnnnnn   240
nnnnnnnnnn nnnnnnnnnn nnnnnnnnnn nnnnnnnnnn nnnnnnnnnn nnnnnnnnnn   300
nnnnnnnnnn nnnnnnnnnn nnnnnnnnnn nnnnnnnnnn nnnnnnnnnn nnnnnnnnnn   360
nnnnnnnnnn nnnnnnnnnn nnnnnnnnnn nnnnnnnnnn nnnnnnnnnn nnnnnnnnnn   420
nnnnnnnnnn nnnnnnnnnn nnnnnnnnnn nnnnnnnnnn nnnnnnnnnn nnnnnnnnnn   480
nnnnnnnnnn nnnnnnnnnn nnnnnnnnnn nnnnnnnnnn nnnnnnnnnn nnnnnnnnnn   540
nnnnnnnnnn nnnnnnnnnn nnnnnnnnnn nnnnnnnnnn nnnnnnnnnn nnnnnnnnnn   600
nnnnnnnnnn nnnnnnnnnn nnnnnnnnnn nnnnnnnnnn nnnnnnnnnn nnnnnnnnnn   660
nnnnnnnnnn nnnnnnnnnn nnnnnnnnnn nnnnnnnnnn nnnnnnnnnn nnnnnnnnnn   720
nnnnnnnnnn nnnnnnnnnn nnnnnnnnnn nnnnnnnnnn nnnnnnnnnn nnnnnnnnnn   780
nnnnnnnnnn nnnnnnnnnn nnnnnnnnnn nnnnnnnnnn nnnnnnnnnn nnnnnnnnnn   840
nnnnnnnnnn nnnnnnnnnn nnnnnnnnnn nnnnnnnnnn nnnnnnnnnn nnnnnnnnnn   900
nnnnnnnnnn nnnnnnnnnn nnnnnnnnnn nnnnnnnnnn nnnnnnnnnn nnnnnnnnnn   960
nnnnnnnnnn nnnnnnnnnn nnnnnnnnnn nnnnnnnnnn nnnnnnnnnn nnnnnnnnnn  1020
nnnnnnnnnn nnnnnnnnnn nnnnnnnnnn nnnnnnnnnn nnnnnnnnnn nnnnnnnnnn  1080
nnnnnnnnnn nnnnnnnnnn nnnnnnnnnn nnnnnnnnnn nnnnnnnnnn nnnnnnnnnn  1140
nnnnnnnnnn nnnnnnnnnn nnnnnnnnnn nnnnnnnnnn nnnnnnnnnn nnnnnnnnnn  1200
nnnnnnnnnn nnnnnnnnnn nnnnnnnnnn nnnnnnnnnn nnnnnnnnnn nnnnnnnnnn  1260
nnnnnnnnnn nnnnnnnnnn nnnnnnnnnn nnnnnnnnnn nnnnnnnnnn nnnnnnnnnn  1320
nnnnnnnnnn nnnnnnnnnn nnnnnnnnnn nnnnnnnnnn nnnnnnnnnn nnnnnnnnnn  1380
nnnnnnnnnn nnnnnnnnnn nnnnnnnnnn nnnnnnnnnn nnnnnnnnnn nnnnnnnnnn  1440
nnnnnnnnnn nnnnnnnnnn nnnnnnnnnn nnnnnnnnnn nnnnnnnnnn nnnnnnnnnn  1500
nnnnnnnnnn nnnnnnnnnn nnnnnnnnnn nnnnnnnnnn nnnnnnnnnn nnnnnnnnnn  1560
nnnnnnnnnn nnnnnnnnnn nnnnnnnnnn nnnnnnnnnn nnnnnnnnnn nnnnnnnnnn  1620
nnnnnnnnnn nnnnnnnnnn nnnnnnnnnn nnnnnnnnnn nnnnnnnnnn nnnnnnnnnn  1680
nnnnnnnnnn nnnnnnnnnn nnnnnnnnnn nnnnnnnnnn nnnnnnnnnn nnnnnnnnnn  1740
nnnnnnnnnn nnnnnnnnnn nnnnnnnnnn nnnnnnnnnn nnnnnnnnnn nnnnnnnnnn  1800
nnnnnnnnnn nnnnnnnnnn nnnnnnnnnn nnnnnnnnnn nnnnnnnnnn nnnnnnnnnn  1860
nnnnnnnnnn nnnnnnnnnn nnnnnnnnnn nnnnnnnnnn nnnnnnnnnn nnnnnnnnnn  1920
```

```
nnnnnnnnnn nnnnnnnnnn nnnnnnnnnn nnnnnnnnnn nnnnnnnnnn nnnnnnnnnn    1980
nnnnnnnnnn nnnnnnnnnn nnnnnnnnnn nnnnnnnnnn nnnnnnnnnn nnnnnnnnnn    2040
nnnnnnnnnn nnnnnnnnnn nnnnnnnnnn nnnnnnnnnn nnnnnnnnnn nnnnnnnnnn    2100
nnnnnnnnnn nnnnnnnnnn nnnnnnnnnn nnnnnnnnnn nnnnnnnnnn nnnnnnnnnn    2160
nnnnnnnnnn nnnnnnnnnn nnnnnnnnnn nnnnnnnnnn nnnnnnnnnn nnnnnnnnnn    2220
nnnnnnnnnn nnnnnnnnnn nnnnnnnnnn nnnnnnnnnn nnnnnnnnnn nnnnnnnnnn    2280
nnnnnnnnnn nnnnnnnnnn nnnnnnnnnn nnnnnnnnnn nnnnnnnnnn nnnnnnnnnn    2340
nnnnnnnnnn nnnnnnnnnn nnnnnnnnnn nnnnnnnnnn nnnnnnnnnn nnnnnnnnnn    2400
nnnnnnnnnn nnnnnnnnnn nnnnnnnnnn nnnnnnnnnn nnnnnnnnnn nnnnnnnnnn    2460
nnnnnnnnnn nnnnnnnnnn nnnnnnnnnn nnnnnnnnnn nnnnnnnnnn nnnnnnnnnn    2520
nnnnnnnnnn nnnnnnnnnn nnnnnnnnnn nnnnnnnnnn nnnnnnnnnn nnnnnnnnnn    2580
nnnnnnnnnn nnnnnnnnnn nnnnnnnnnn nnnnnnnnnn nnnnnnnnnn nnnnnnnnnn    2640
nnnnnnnnnn nnnnnnnnnn nnnnnnnnnn nnnnnnnnnn nnnnnnnnnn nnnnnnnnnn    2700
nnnnnnnnnn nnnnnnnnnn nnnnnnnnnn nnnnnnnnnn nnnnnnnnnn nnnnnnnnnn    2760
nnnnnnnnnn nnnnnnnnnn nnnnnnnnnn nnnnnnnnnn nnnnnnnnnn nnnnnnnnnn    2820
nnnnnnnnnn nnnnnnnnnn nnnnnnnnnn nnnnnnnnnn nnnnnnnnnn nnnnnnnnnn    2880
nnnnnnnnnn nnnnnnnnnn nnnnnnnnnn nnnnnnnnnn nnnnnnnnnn nnnnnnnnnn    2940
nnnnnnnnnn nnnnnnnnnn nnnnnnnnnn nnnnnnnnnn nnnnnnnnnn gggggggggg    3000

<210> SEQ ID NO 12
<211> LENGTH: 612
<212> TYPE: DNA
<213> ORGANISM: Homo sapiens

<400> SEQUENCE: 12
cggcggcggc ggcggcggcg gcggcggcgg cggcggcggc ggcggcggcg gcggcggcgg      60
cggcggcggc ggcggcggcg gcggcggcgg cggcggcggc ggcggcggcg gcggcggcgg     120
cggcggcggc ggcggcggcg gcggcggcgg cggcggcggc ggcggcggcg gcggcggcgg     180
cggcggcggc ggcggcggcg gcggcggcgg cggcggcggc ggcggcggcg gcggcggcgg     240
cggcggcggc ggcggcggcg gcggcggcgg cggcggcggc ggcggcggcg gcggcggcgg     300
cggcggcggc ggcggcggcg gcggcggcgg cggcggcggc ggcggcggcg gcggcggcgg     360
cggcggcggc ggcggcggcg gcggcggcgg cggcggcggc ggcggcggcg gcggcggcgg     420
cggcggcggc ggcggcggcg gcggcggcgg cggcggcggc ggcggcggcg gcggcggcgg     480
cggcggcggc ggcggcggcg gcggcggcgg cggcggcggc ggcggcggcg gcggcggcgg     540
cggcggcggc ggcggcggcg gcggcggcgg cggcggcggc ggcggcggcg gcggcggcgg     600
cggcggcggc gg                                                         612

<210> SEQ ID NO 13
<211> LENGTH: 15
<212> TYPE: DNA
<213> ORGANISM: Unknown
<220> FEATURE:
<223> OTHER INFORMATION: Example nucleotide sequence

<400> SEQUENCE: 13
acgtagggca ttgca                                                       15
```

```
<210> SEQ ID NO 14
<211> LENGTH: 14
<212> TYPE: DNA
<213> ORGANISM: Unknown
<220> FEATURE:
<223> OTHER INFORMATION: Example nucleotide sequence

<400> SEQUENCE: 14
acctaggcat tgca                                                       14

<210> SEQ ID NO 15
<211> LENGTH: 231
<212> TYPE: PRT
<213> ORGANISM: Homo sapiens

<400> SEQUENCE: 15
```

Met Glu Pro Gln Val Thr Leu Asn Val Thr Phe Lys Asn Glu Ile Gln
1               5                   10                  15

Ser Phe Leu Val Ser Asp Pro Glu Asn Thr Thr Trp Ala Asp Ile Glu
            20                  25                  30

Ala Met Val Lys Val Ser Phe Asp Leu Asn Thr Ile Gln Ile Lys Tyr
        35                  40                  45

Leu Asp Glu Glu Asn Glu Glu Val Ser Ile Asn Ser Gln Gly Glu Tyr
    50                  55                  60

Glu Glu Ala Leu Lys Met Ala Val Lys Gln Gly Asn Gln Leu Gln Met
65                  70                  75                  80

Gln Val His Glu Gly His His Val Val Asp Glu Ala Pro Pro Pro Val
                85                  90                  95

Val Gly Ala Lys Arg Leu Ala Ala Arg Ala Gly Lys Lys Pro Leu Ala
            100                 105                 110

His Tyr Ser Ser Leu Val Arg Val Leu Gly Ser Asp Met Lys Thr Pro
        115                 120                 125

Glu Asp Pro Ala Val Gln Ser Phe Pro Leu Val Pro Cys Asp Thr Asp
    130                 135                 140

Gln Pro Gln Asp Lys Pro Pro Asp Trp Phe Thr Ser Tyr Leu Glu Thr
145                 150                 155                 160

Phe Arg Glu Gln Val Val Asn Glu Thr Val Glu Lys Leu Glu Gln Lys
                165                 170                 175

Leu His Gly Lys Leu Val Leu Gln Asn Pro Ser Leu Gly Ser Cys Pro
            180                 185                 190

Ser Glu Val Ser Met Pro Thr Ser Glu Glu Thr Leu Phe Leu Pro Glu
        195                 200                 205

Asn Gln Phe Ser Trp His Ile Ala Cys Asn Asn Cys Gln Arg Arg Ile
    210                 215                 220

Val Gly Val Arg Tyr Gln Cys
225                 230

```
<210> SEQ ID NO 16
<211> LENGTH: 112
<212> TYPE: PRT
<213> ORGANISM: Homo sapiens

<400> SEQUENCE: 16
```

Met Trp Lys Gly Gly Arg Ser His Pro Phe Leu Pro Cys Ser Ser Arg
1               5                   10                  15

Arg Ala Gly Ser Gly Gly Gln Leu Asp Ser Ile Leu Pro His Gln Ser
            20                  25                  30

```
Pro Ala Trp Gly Pro Trp Gly Cys Lys Asp Leu Ser Ser Gly Val Pro
            35                  40                  45

Ser Phe Leu Thr Ser Ser Ile Leu Trp Lys Ser Ala Val Phe Ala Glu
 50                  55                  60

Asp Asn Gly Leu Lys Ile His Leu Cys Ser Tyr Lys Arg Asp Asp Leu
 65                  70                  75                  80

Val Leu Phe Tyr Asp Cys Thr Ser Phe Val Leu Thr Phe Gly Pro Ser
                 85                  90                  95

Pro Trp Phe Leu Thr Gln Gly Phe Leu Asn Pro Leu Glu Phe Ser Ala
            100                 105                 110

<210> SEQ ID NO 17
<211> LENGTH: 160
<212> TYPE: PRT
<213> ORGANISM: Homo sapiens

<400> SEQUENCE: 17

Met Asp Leu Ser Ala Leu Arg Val Glu Glu Val Gln Asn Val Ile Asn
 1               5                  10                  15

Ala Met Gln Lys Ile Leu Glu Cys Pro Ile Cys Leu Glu Leu Ile Lys
             20                  25                  30

Glu Pro Val Ser Thr Lys Cys Asp His Ile Phe Cys Lys Phe Cys Met
         35                  40                  45

Leu Lys Leu Leu Asn Gln Lys Lys Gly Pro Ser Gln Cys Pro Leu Cys
 50                  55                  60

Lys Asn Asp Ile Thr Lys Arg Ser Leu Gln Glu Ser Thr Arg Phe Ser
 65                  70                  75                  80

Gln Leu Val Glu Glu Leu Leu Lys Ile Ile Cys Ala Phe Gln Leu Asp
                 85                  90                  95

Thr Gly Leu Glu Tyr Ala Asn Ser Tyr Asn Phe Ala Lys Lys Glu Asn
            100                 105                 110

Asn Ser Pro Glu His Leu Lys Asp Glu Val Ser Ile Ile Gln Ser Met
        115                 120                 125

Gly Tyr Arg Asn Arg Ala Lys Arg Leu Leu Gln Ser Glu Pro Glu Asn
    130                 135                 140

Pro Ser Leu Gln Glu Thr Ser Leu Ser Val Gln Leu Ser Asn Leu Gly
145                 150                 155                 160

<210> SEQ ID NO 18
<211> LENGTH: 311
<212> TYPE: PRT
<213> ORGANISM: Homo sapiens

<400> SEQUENCE: 18

Leu Pro Arg Gln Asp Leu Glu Gly Thr Pro Tyr Leu Glu Ser Gly Ile
 1               5                  10                  15

Ser Leu Phe Ser Asp Asp Pro Glu Ser Asp Pro Ser Glu Asp Arg Ala
             20                  25                  30

Pro Glu Ser Ala Arg Val Gly Asn Ile Pro Ser Ser Thr Ser Ala Leu
         35                  40                  45

Lys Val Pro Gln Leu Lys Val Ala Glu Ser Ala Gln Ser Pro Ala Ala
 50                  55                  60

Ala His Thr Thr Asp Thr Ala Gly Tyr Asn Ala Met Glu Glu Ser Val
 65                  70                  75                  80

Ser Arg Glu Lys Pro Glu Leu Thr Ala Ser Thr Glu Arg Val Asn Lys
                 85                  90                  95
```

```
Arg Met Ser Met Val Val Ser Gly Leu Thr Pro Glu Glu Phe Met Leu
            100                 105                 110

Val Tyr Lys Phe Ala Arg Lys His His Ile Thr Leu Thr Asn Leu Ile
        115                 120                 125

Thr Glu Glu Thr Thr His Val Val Met Lys Thr Asp Ala Glu Phe Val
    130                 135                 140

Cys Glu Arg Thr Leu Lys Tyr Phe Leu Gly Ile Ala Gly Lys Trp
145                 150                 155                 160

Val Val Ser Tyr Phe Trp Val Thr Gln Ser Ile Lys Glu Arg Lys Met
                165                 170                 175

Leu Asn Glu His Asp Phe Glu Val Arg Gly Asp Val Val Asn Gly Arg
            180                 185                 190

Asn His Gln Gly Pro Lys Arg Ala Arg Glu Ser Gln Asp Arg Lys Ile
        195                 200                 205

Phe Arg Gly Leu Glu Ile Cys Cys Tyr Gly Pro Phe Thr Asn Met Pro
    210                 215                 220

Thr Asp Gln Leu Glu Trp Met Val Gln Leu Cys Gly Ala Ser Val Val
225                 230                 235                 240

Lys Glu Leu Ser Ser Phe Thr Leu Gly Thr Gly Val His Pro Ile Val
                245                 250                 255

Val Val Gln Pro Asp Ala Trp Thr Glu Asp Asn Gly Phe His Ala Ile
            260                 265                 270

Gly Gln Met Cys Glu Ala Pro Val Val Thr Arg Glu Trp Val Leu Asp
        275                 280                 285

Ser Val Ala Leu Tyr Gln Cys Gln Glu Leu Asp Thr Tyr Leu Ile Pro
    290                 295                 300

Gln Ile Pro His Ser His Tyr
305                 310

<210> SEQ ID NO 19
<211> LENGTH: 120
<212> TYPE: DNA
<213> ORGANISM: Homo sapiens

<400> SEQUENCE: 19
gatctaattt tgtccgttca ggggaacata attttgcctg gctttgctaa tccaaatgca      60
catttgaaca caacaatctg aatagttaca acatacaaag catgtgggtg aagagtagct     120

<210> SEQ ID NO 20
<211> LENGTH: 162
<212> TYPE: DNA
<213> ORGANISM: Homo sapiens

<400> SEQUENCE: 20
tacatatctc tgacccttg tccccatcca atctccccag accttccatc ccaagcccaa      60
acacaacctt acctgctgct ccttttcagg caccctggcc accaaatata ggaacccata    120
aattttgctc atactctatg ttctactagg caagtcctga tc                        162

<210> SEQ ID NO 21
<211> LENGTH: 195
<212> TYPE: DNA
<213> ORGANISM: Unknown
<220> FEATURE:
<223> OTHER INFORMATION: Example nucleotide sequence

<400> SEQUENCE: 21
gacttacggc aaatgtgtgc caaagaggcg gcacataagg attttaaaaa ggcagttggt      60
```

```
gcctttctg taacttatga tccagaaaat tatcagcttg tcattttgtc catcaatgaa      120
gtcacctcaa agcgagcaca tatgctgatt gacatccact ttcggagtct gcgcactaag    180
ttgtctctga taatg                                                      195

<210> SEQ ID NO 22
<211> LENGTH: 34
<212> TYPE: DNA
<213> ORGANISM: Unknown
<220> FEATURE:
<223> OTHER INFORMATION: Example nucleotide sequence

<400> SEQUENCE: 22
acgggagcat catcatcctt acttacttcc aagg                                 34

<210> SEQ ID NO 23
<211> LENGTH: 32
<212> TYPE: DNA
<213> ORGANISM: Unknown
<220> FEATURE:
<223> OTHER INFORMATION: Example nucleotide sequence

<400> SEQUENCE: 23
acgggcgcat catcacctta cttacttcca ag                                   32

<210> SEQ ID NO 24
<211> LENGTH: 33
<212> TYPE: DNA
<213> ORGANISM: Unknown
<220> FEATURE:
<223> OTHER INFORMATION: Example nucleotide sequence

<400> SEQUENCE: 24
acgggcgcat catcatcctt acttacttcc aag                                  33

<210> SEQ ID NO 25
<211> LENGTH: 35
<212> TYPE: DNA
<213> ORGANISM: Unknown
<220> FEATURE:
<223> OTHER INFORMATION: Example nucleotide sequence

<400> SEQUENCE: 25
acgggcgcat catcatcctt acccttactt ccaag                                35

<210> SEQ ID NO 26
<211> LENGTH: 33
<212> TYPE: DNA
<213> ORGANISM: Unknown
<220> FEATURE:
<223> OTHER INFORMATION: Example nucleotide sequence

<400> SEQUENCE: 26
acgggcgcat catcatcctt cttccaagac tta                                  33

<210> SEQ ID NO 27
<211> LENGTH: 17
<212> TYPE: DNA
<213> ORGANISM: Unknown
<220> FEATURE:
<223> OTHER INFORMATION: Example nucleotide sequence

<400> SEQUENCE: 27
ggaggctagt tagtata                                                    17
```

```
<210> SEQ ID NO 28
<211> LENGTH: 14
<212> TYPE: PRT
<213> ORGANISM: Unknown
<220> FEATURE:
<223> OTHER INFORMATION: Example amino acid sequence

<400> SEQUENCE: 28

Met Asp Leu Ser Ala Leu Arg Val Glu Val Ala Met Gln Glu
1               5                   10

<210> SEQ ID NO 29
<211> LENGTH: 16
<212> TYPE: PRT
<213> ORGANISM: Unknown
<220> FEATURE:
<223> OTHER INFORMATION: Example amino acid sequence

<400> SEQUENCE: 29

Leu Pro Arg Gln Asp Leu Glu Ser Gly Ile Ser Leu Phe Pro Glu Ser
1               5                   10                  15

<210> SEQ ID NO 30
<211> LENGTH: 12
<212> TYPE: RNA
<213> ORGANISM: Unknown
<220> FEATURE:
<223> OTHER INFORMATION: Example ribonucleotide sequence

<400> SEQUENCE: 30
gauaccucag uc                                                         12

<210> SEQ ID NO 31
<211> LENGTH: 12
<212> TYPE: DNA
<213> ORGANISM: Unknown
<220> FEATURE:
<223> OTHER INFORMATION: Example nucleotide sequence

<400> SEQUENCE: 31
gatacctcag tc                                                         12

<210> SEQ ID NO 32
<211> LENGTH: 17
<212> TYPE: RNA
<213> ORGANISM: Unknown
<220> FEATURE:
<223> OTHER INFORMATION: Example ribonucleotide sequence

<400> SEQUENCE: 32
ggaggcuagu uaguaua                                                    17
```